us 009994555B2

United States Patent
Bannister et al.

(10) Patent No.: US 9,994,555 B2
(45) Date of Patent: Jun. 12, 2018

(54) CHROMENONE INHIBITORS OF MONOCARBOXYLATE TRANSPORTERS

(71) Applicant: THE SCRIPPS RESEARCH INSTITUTE, La Jolla, CA (US)

(72) Inventors: Thomas D. Bannister, Palm Beach Gardens, FL (US); Hui Wang, Jupiter, FL (US); Chao Wang, Palm Beach Gardens, FL (US); John L. Cleveland, Land O'Lakes, FL (US)

(73) Assignee: The Scripps Research Institute, La Jolla, CA (US)

(*) Notice: Subject to any disclaimer, the term of this patent is extended or adjusted under 35 U.S.C. 154(b) by 0 days. days.

(21) Appl. No.: 15/545,117

(22) PCT Filed: Jan. 22, 2016

(86) PCT No.: PCT/US2016/014455
§ 371 (c)(1),
(2) Date: Jul. 20, 2017

(87) PCT Pub. No.: WO2016/118822
PCT Pub. Date: Jul. 28, 2016

(65) Prior Publication Data
US 2018/0009792 A1 Jan. 11, 2018

Related U.S. Application Data

(60) Provisional application No. 62/106,465, filed on Jan. 22, 2015.

(51) Int. Cl.
| | | |
|---|---|---|
| A61K 31/352 | (2006.01) | |
| C07D 405/12 | (2006.01) | |
| A61K 31/4709 | (2006.01) | |
| C07D 311/22 | (2006.01) | |
| A61K 31/353 | (2006.01) | |
| A61K 31/4433 | (2006.01) | |
| A61K 31/155 | (2006.01) | |
| A61K 31/427 | (2006.01) | |
| A61K 31/4725 | (2006.01) | |
| A61K 31/506 | (2006.01) | |
| A61K 31/453 | (2006.01) | |
| C07D 417/12 | (2006.01) | |

(52) U.S. Cl.
CPC .......... *C07D 405/12* (2013.01); *A61K 31/155* (2013.01); *A61K 31/353* (2013.01); *A61K 31/427* (2013.01); *A61K 31/4433* (2013.01); *A61K 31/453* (2013.01); *A61K 31/4709* (2013.01); *A61K 31/4725* (2013.01); *A61K 31/506* (2013.01); *C07D 311/22* (2013.01); *C07D 417/12* (2013.01)

(58) Field of Classification Search
CPC .................................. A61K 31/352
See application file for complete search history.

(56) References Cited

FOREIGN PATENT DOCUMENTS

WO WO2014195507 * 12/2014

OTHER PUBLICATIONS

Passamonti, 2009, Current Drug Metabolism, vol. 10, p. 369-394. (Year: 2009).*

* cited by examiner

*Primary Examiner* — Rebecca L Anderson
*Assistant Examiner* — Karen Cheng
(74) *Attorney, Agent, or Firm* — Geoffrey K. Cooper; Thomas Fitting

(57) ABSTRACT

The invention provides compounds effective as inhibitors of monocarboxylate transporters such as MCT1 and MCT4, which can be used for treatment of medical conditions wherein treatment of the condition with a compound having an inhibitor effect on MCT1, MCT4, or both is medically indicated. Compounds of the invention can have antitumor, antidiabetes, anti-inflammatory, or immunosuppressive pharmacological effects, and can be effective for treatment of cancer and of type II diabetes.

11 Claims, No Drawings

CHROMENONE INHIBITORS OF MONOCARBOXYLATE TRANSPORTERS

CROSS-REFERENCE TO RELATED APPLICATION

This application claims the priority of U.S. Provisional Application Ser. No. 62/106,465, filed Jan. 22, 2015, the disclosure of which is incorporated herein by reference in its entirety.

STATEMENT OF GOVERNMENT SUPPORT

This invention was made with government support under R01 CA154739 awarded by the National Institutes of Health. The government has certain rights in the invention.

BACKGROUND

In the 1920s the German biochemist Otto Warburg described metabolic differences between cancerous and normal cells, where he noted that tumor cells rely upon a high rate of aerobic glycolysis rather than oxidative phosphorylation to produce energy for maintenance of cellular functions.[1,2] Indeed, cancer cells have up to a 60-fold enhanced rate of glycolysis relative to normal cells, even with sufficient oxygen.[1] This dependence upon glycolysis, and its consequences, is termed "the Warburg effect".[2]

Malignant cells are highly anabolic and require and require very high levels nutrients, ATP and building blocks to synthesize components needed for their growth and survival. Use of the glycolytic pathway provides ATP but also drives production of lactate, which is produced from pyruvate at the end of the glycolytic pathway. Massive lactate production by the tumor cell requires an efficient means for its consumption or elimination, to prevent intracellular acidification of the cancer cell.

Two mechanisms for handling excess lactate have been described. First, in some rare tumor types lactate is converted to pyruvate for entry into the TCA cycle. More commonly, lactate homeostasis is maintained via a family of twelve-membrane pass cell surface proteins known as the monocarboxylate transporters (MCTs; also known as the SLC16a transporter family). Fourteen MCTs are known, but only MCT1, MCT2, MCT3 and MCT4 transport small monocarboxylates such as lactate, pyruvate and ketone bodies (acetoacetate and β-hydroxybutyrate) across plasma membranes in a proton-linked exchange.[3] Expression profiling studies have established that most aggressive tumor types express markedly elevated levels of MCT1, MCT4 or both.[4] The chaperone protein CD147, which contains immunoglobulin-like domains, is required for MCT1 and MCT4 cell surface expression and is co-localized with the transporters. MCT1, MCT4 and CD147 are now high priority targets for cancer therapeutics.[4]

The expression of MCT1 and MCT4 is regulated by two major oncogenic transcription factors, MYC and hypoxia inducible factor-1α (HIF-1α), respectively,[4,5] that direct marked increases in the production of key proteins that support aerobic glycolysis, including amino acid transporters and enzymes involved in the catabolism of glutamine and glucose.[6] Malignancies having MYC involvement and hypoxic tumors are generally resistant to current frontline therapies, with high rates of treatment failure, relapse and high patient mortality.[7,8] Importantly, inhibition of MCT1 or MCT4 can kill tumor cells ex vivo and provoke tumor regression in vivo,[4,9] and their potency is augmented by agents such as metformin that force a glycolytic phenotype upon the cancer cell.[4]

Many weak MCT inhibitors (i.e., those effective at high micromolar levels) have been described, including α-cyano-4-hydroxycinnamate[10,11] stilbene disulfonates,[12] phloretin[13] and related flavonoids.[14] Coumarin-derived covalent MCT inhibitors have also recently been disclosed,[15,16] as have pteridinones.[17]

The most advanced MCT1 inhibitors are related pyrrolopyrimidine diones, pyrrolopyridazinones, and thienopyrimidine diones,[18-23] including a compound that has advanced into clinical trials for treating some human malignancies.[24,25] These compounds, and to our knowledge all MCT1 inhibitors yet described, are dual MCT1/MCT2 inhibitors. MCT2 has very high sequence homology with MCT1, yet it likely has a lesser role than MCT1 and MCT4 for monocarboxylate transport in human cancers based upon expression studies. However, MCT2 inhibition may play a role in potential off-target effects of current agents that could arise from blocking lactate transport in normal cells.

The first highly potent MCT inhibitor was initially identified via a cell-based assay seeking immunosuppressive agents that inhibit NFAT1-directed IL-2 transcription.[26] MCT1 inhibition as its mechanism of action was described a full decade later.[18] Several subsequently published analogs are also potent MCT1 inhibitors, with low nanomolar Ki values for MCT1 inhibition and low nanomolar $EC_{50}$ values inn MTT assays for growth of MCT1-expressing tumors.

In many human tumors MCT1 and MCT4 are inversely expressed. Small molecule MCT1 inhibitors are now known to disable tumor cell metabolism, proliferation and survival, and impair tumorigenic potential in vivo in tumors highly expressing MCT1.[4] MCT4 inhibitors are likely to be similarly effective for tumors highly expressing MCT4. Antitumor effects of MCT1 inhibitors are augmented by co-administration of the biguanide metformin, which is thought to further augment reliance by tumor cells upon aerobic glycolysis and thus increase the demand to MCT1-mediated efflux of lactate.[4]

In addition to antitumor effects, inhibitors of MCT1 and/or MCT4 may have other important biological effects, such as immune suppression,[18] anti-inflammatory,[26] and antidiabetic effects.[27-32] MCT1 is normally expressed at very low levels in pancreatic islets and in beta-cells in particular.[27-28] This scenario explains the very slow uptake of lactate in these cells.[29] A hallmark of exercise-induced hyperinsulinism (EIHI) is inappropriate insulin secretion following vigorous physical activity, which leads to hypoglycemia.[30] In a 2012 study, Rutter and co-workers established that EIHI is associated with elevated expression of MCT1 in beta-cells and that transgenic mice engineered to overexpress MCT1 in part displayed many of the hallmarks of EIHI6.[31] While the link between lactate and insulin secretion has been suggested since the late 1980s[32] these more recent studies clarify the central role of MCT1 (and perhaps of the related lactate transporters MCT2 and MCT4).

SUMMARY

The invention provides, in various embodiments, a compound of formula (IA)

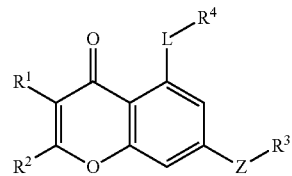

(IA)

wherein

R$^1$ is H, straight chain (C$_1$-C$_6$)alkyl, branched chain (C$_3$-C$_6$)alkyl, (C$_3$-C$_7$)cycloalkyl, or (C$_1$-C$_6$)fluoroalkyl;

R$^2$ is H, straight chain (C$_1$-C$_6$)alkyl, branched chain (C$_3$-C$_6$)alkyl, (C$_3$-C$_7$)cycloalkyl, or (C$_1$-C$_6$)fluoroalkyl, a (C$_6$-C$_{10}$)aryl ring system, a 5- to 9-membered heteroaryl ring system, a (C$_1$-C$_6$)alkyl-(C$_6$-C$_{10}$)aryl ring system, or a (C$_1$-C$_6$)alkyl-(5- to 9-membered)heteroaryl ring system;

provided that when R$^2$ comprises an aryl or heteroaryl ring system, the ring system bears 0-2 independently selected substituents from the group consisting of fluoro, chloro, trifluoromethyl, (C$_1$-C$_6$)alkoxy, and (C$_1$-C$_6$)fluoroalkyl;

Z is O, CH$_2$, CH(CH$_3$), S, NH, N((C$_1$-C$_6$)alkyl), OCH$_2$, OCH(CH$_3$), CH$_2$S, CH(CH$_3$)S, CH$_2$NH, CH(CH$_3$)NH, CH$_2$N(CH$_3$), or CH(CH$_3$)N(CH$_3$);

R$^3$ is a monocyclic or bicyclic (C6-C10)aryl or a monocyclic or bicyclic (5- to 10-membered)heteroaryl, wherein the aryl or heteroaryl can be substituted or unsubstituted;

L is O, (CH$_2$)$_m$ wherein m=1 or 2, CH((C$_1$-C$_6$)alkyl), CH((C$_3$-C$_7$)cycloalkyl), CH((C$_1$-C$_6$)alkyl)CH$_2$, S, NH, N((C$_1$-C$_6$)alkyl), OCH$_2$, OCH((C$_1$-C$_6$)alkyl), SCH$_2$, SCH ((C$_1$-C$_6$)alkyl), CH$_2$NH, CH$_2$N((C$_1$-C$_6$)alkyl), CH(CH$_3$) NH, CH(CH$_3$)N((C$_1$-C$_6$)alkyl), or a bond;

R$^4$ is a group of formula (IIA)

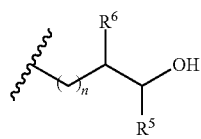

(IIA)

wherein a wavy line indicates a point of bonding, n=0, 1, or 2; R$^5$ is H, straight chain (C$_1$-C$_6$)alkyl, branched chain (C$_3$-C$_6$)alkyl, (C$_3$-C$_7$)cycloalkyl, or (C$_1$-C$_6$)fluoroalkyl; R$^6$ is H, methyl, or OH;

or, R$^4$ is a group of formula (IIB)

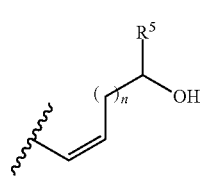

(IIB)

wherein a wavy line indicates a point of bonding, n=0, 1, or 2; R$^5$ is H, straight chain (C$_1$-C$_6$)alkyl, branched chain (C$_3$-C$_6$)alkyl, (C$_3$-C$_7$)cycloalkyl, or (C$_1$-C$_6$)fluoroalkyl;

or, R$^4$ is a group of formula (IIC)

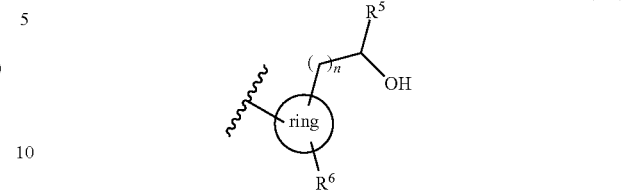

(IIC)

wherein a wavy line indicates a point of bonding, n=0, 1, or 2; R$^5$ is H, straight chain (C$_1$-C$_6$)alkyl, branched chain (C$_3$-C$_6$)alkyl, (C$_3$-C$_7$)cycloalkyl, (C$_1$-C$_6$)fluoroalkyl, (C$_6$-C$_{10}$)aryl, or (4- to 7-membered)heterocyclyl comprising 1 or 2 heteroatoms selected from the group consisting of NH, N(C1-C6)alkyl, O, and S; R$^6$ is halo, (C$_1$-C$_6$)alkyl, (C$_1$-C$_6$) alkoxy, (C$_1$-C$_6$)fluoroalkyl, or (C$_1$-C$_6$)fluoroalkoxy; wherein the ring is a (C$_6$-C$_{10}$)aryl or a (5- to 9-membered) heteroaryl comprising a carbon atom at the position of bonding of group L, and 0-3 independently selected R$^6$ groups are present as substituents on the ring; or, wherein the ring is a non-aromatic cycloalkyl or heterocyclyl ring comprising a carbon atom at the position of bonding of group L, wherein the carbon atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, N(C$_1$-C$_6$)alkyl, or N(C$_1$-C$_6$) fluoroalkyl;

or, R$^4$ is a group of formula (IID)

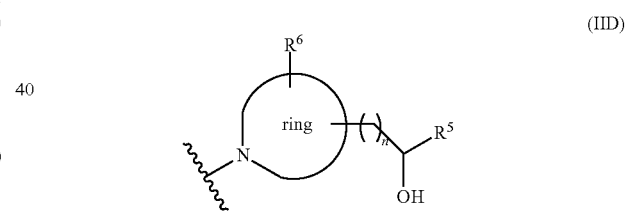

(IID)

wherein a wavy line indicates a point of bonding; n=0, 1, or 2; R$^5$ is H, straight chain (C$_1$-C$_6$)alkyl, branched chain (C$_3$-C$_6$)alkyl, (C$_3$-C$_7$)cycloalkyl, (C$_1$-C$_6$)fluoroalkyl, (C$_6$-C$_{10}$)aryl, or (4- to 7-membered)heterocyclyl comprising 1 or 2 heteroatoms selected from the group consisting of NH, N(C1-C6)alkyl, O, and S; R$^6$ is halo, (C$_1$-C$_6$)alkyl, (C$_1$-C$_6$) alkoxy, (C$_1$-C$_6$)fluoroalkyl, or (C$_1$-C$_6$)fluoroalkoxy; wherein the ring is a (5- to 9-membered)heterocyclyl or a (5- to 9-membered)heteroaryl comprising a nitrogen atom at the position of bonding of group L, wherein the nitrogen atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, N(C$_1$-C$_6$)alkyl, or N(C$_1$-C$_6$)fluoroalkyl; and 0-3 independently selected R$^6$ groups are present as substituents on the ring; or a pharmaceutically acceptable salt thereof. The invention further provides a pharmaceutical composition comprising a compound of any one of the invention and a pharmaceutically acceptable excipient.

The invention further provides, in various embodiments, a method of inhibiting monocarboxylate transporter MCT1, monocarboxylate transporter MCT4, or both, comprising contacting the monocarboxylate transporter with an effective amount or concentration of a compound of the invention. The method can be used for treatment of a condition in a mammal wherein treatment of the condition with a compound having an inhibitor effect on MCT1, MCT4, or both is medically indicated, comprising administering an effective amount of a compound of the invention. For instance, the compound can show an antitumor, antidiabetes, anti-inflammatory, or immunosuppressive pharmacological effect. Compounds of the invention can be used for treatment of cancer or type II diabetes.

COMPOUNDS OF THE INVENTION

The discovery of novel MCT inhibitors is central to this application. We have discovered a number of novel MCT inhibitors of formula (IA)

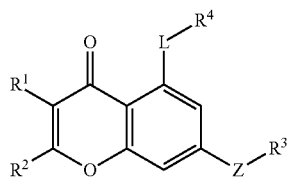

(IA)

wherein $R^1$ is H, straight chain $(C_1-C_6)$alkyl, branched chain $(C_3-C_6)$alkyl, $(C_3-C_7)$cycloalkyl, or $(C_1-C_6)$fluoroalkyl;

$R^2$ is H, straight chain $(C_1-C_6)$alkyl, branched chain $(C_3-C_6)$alkyl, $(C_3-C_7)$cycloalkyl, or $(C_1-C_6)$fluoroalkyl, a $(C_6-C_{10})$aryl ring system, a 5- to 9-membered heteroaryl ring system, a $(C_1-C_6)$alkyl-$(C_6-C_{10})$aryl ring system, or a $(C_1-C_6)$alkyl-(5- to 9-membered)heteroaryl ring system;

provided that when $R^2$ comprises an aryl or heteroaryl ring system, the ring system bears 0-2 independently selected substituents from the group consisting of fluoro, chloro, trifluoromethyl, $(C_1-C_6)$alkoxy, and $(C_1-C_6)$fluoroalkoxy;

Z is O, $CH_2$, $CH(CH_3)$, S, NH, $N((C_1-C_6)$alkyl$)$, $OCH_2$, $OCH(CH_3)$, $CH_2S$, $CH(CH_3)S$, $CH_2NH$, $CH(CH_3)NH$, $CH_2N(CH_3)$, or $CH(CH_3)N(CH_3)$;

$R^3$ is a monocyclic or bicyclic (C6-C10)aryl or a monocyclic or bicyclic (5- to 10-membered)heteroaryl, wherein the aryl or heteroaryl can be substituted or unsubstituted;

L is O, $(CH_2)_m$ wherein m=1 or 2, $CH((C_1-C_6)$alkyl$)$, $CH((C_3-C_7)$cycloalkyl$)$, $CH((C_1-C_6)$alkyl$)CH_2$, S, NH, $N((C_1-C_6)$alkyl$)$, $OCH_2$, $OCH((C_1-C_6)$alkyl$)$, $SCH_2$, $SCH((C_1-C_6)$alkyl$)$, $CH_2NH$, $CH_2N((C_1-C_6)$alkyl$)$, $CH(CH_3)NH$, $CH(CH_3)N((C_1-C_6)$alkyl$)$, or a bond;

$R^4$ is a group of formula (IIA)

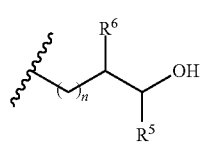

(IIA)

wherein a wavy line indicates a point of bonding, n=0, 1, or 2; $R^5$ is H, straight chain $(C_1-C_6)$alkyl, branched chain $(C_3-C_6)$alkyl, $(C_3-C_7)$cycloalkyl, or $(C_1-C_6)$fluoroalkyl; $R^6$ is H, methyl, or OH;

or, $R^4$ is a group of formula (IIB)

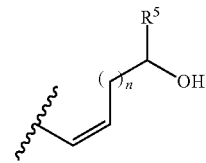

wherein a wavy line indicates a point of bonding, n=0, 1, or 2; $R^5$ is H, straight chain $(C_1-C_6)$alkyl, branched chain $(C_3-C_6)$alkyl, $(C_3-C_7)$cycloalkyl, or $(C_1-C_6)$fluoroalkyl;

or, $R^4$ is a group of formula (IIC)

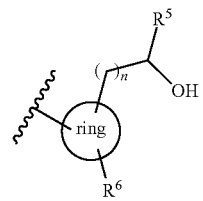

(IIC)

wherein a wavy line indicates a point of bonding, n=0, 1, or 2; $R^5$ is H, straight chain $(C_1-C_6)$alkyl, branched chain $(C_3-C_6)$alkyl, $(C_3-C_7)$cycloalkyl, $(C_1-C_6)$fluoroalkyl, $(C_6-C_{10})$aryl, or (4- to 7-membered)heterocyclyl comprising 1 or 2 heteroatoms selected from the group consisting of NH, N(C1-C6)alkyl, O, and S; $R^6$ is halo, $(C_1-C_6)$alkyl, $(C_1-C_6)$alkoxy, $(C_1-C_6)$fluoroalkyl, or $(C_1-C_6)$fluoroalkoxy; wherein the ring is a $(C_6-C_{10})$aryl or a (5- to 9-membered) heteroaryl comprising a carbon atom at the position of bonding of group L, and 0-3 independently selected $R^6$ groups are present as substituents on the ring; or, wherein the ring is a non-aromatic cycloalkyl or heterocyclyl ring comprising a carbon atom at the position of bonding of group L, wherein the carbon atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, $N(C_1-C_6)$alkyl, or $N(C_1-C_6)$ fluoroalkyl;

or, $R^4$ is a group of formula (IID)

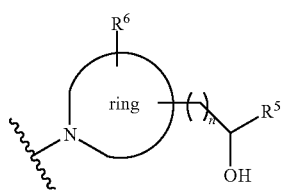

(IID)

wherein a wavy line indicates a point of bonding; n=0, 1, or 2; $R^5$ is H, straight chain $(C_1-C_6)$alkyl, branched chain $(C_3-C_6)$alkyl, $(C_3-C_7)$cycloalkyl, $(C_1-C_6)$fluoroalkyl, $(C_6-C_{10})$aryl, or (4- to 7-membered)heterocyclyl comprising 1 or 2 heteroatoms selected from the group consisting of NH, N(C1-C6)alkyl, O, and S; $R^6$ is halo, $(C_1-C_6)$alkyl, $(C_1-C_6)$alkoxy, $(C_1-C_6)$fluoroalkyl, or $(C_1-C_6)$fluoroalkoxy; wherein the ring is a (5- to 9-membered)heterocyclyl or a (5- to 9-membered)heteroaryl comprising a nitrogen atom at the position of bonding of group L, wherein the nitrogen atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, $N(C_1-C_6)$alkyl, or $N(C_1-C_6)$fluoroalkyl; and 0-3 independently selected $R^6$ groups are present as substituents on the ring;

or a pharmaceutically acceptable salt thereof.

For example, in various embodiments, for a compound of the invention, when the $R^3$ group is monocyclic, the core ring system can consist of 5 or 6 atoms in total, with 1-6 carbon atoms, 0-4 nitrogen atoms, 0-2 oxygen atoms, and 0-1 sulfur atoms. Representative examples can include the following:

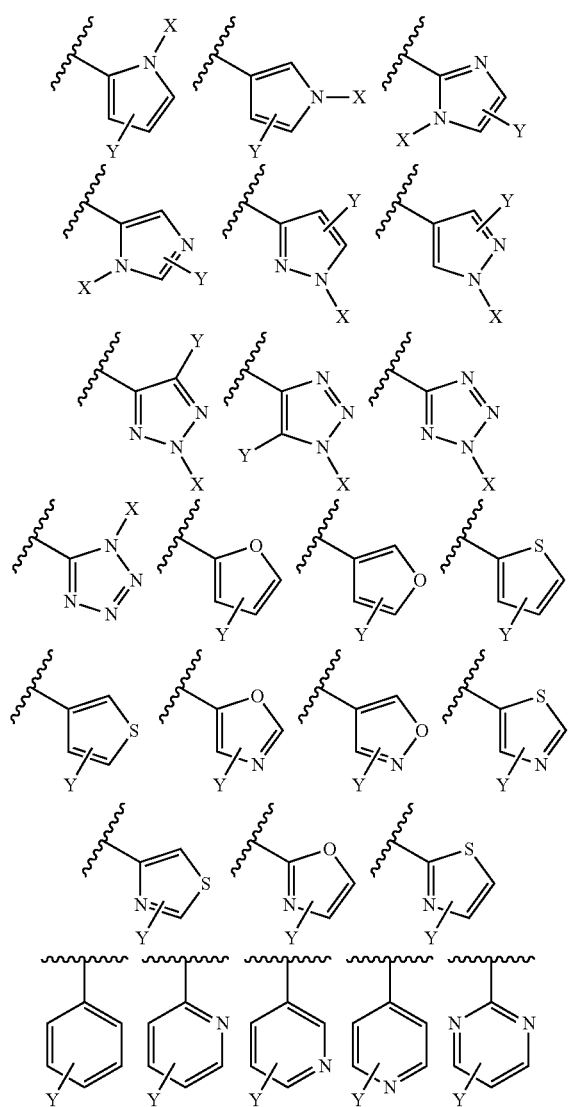

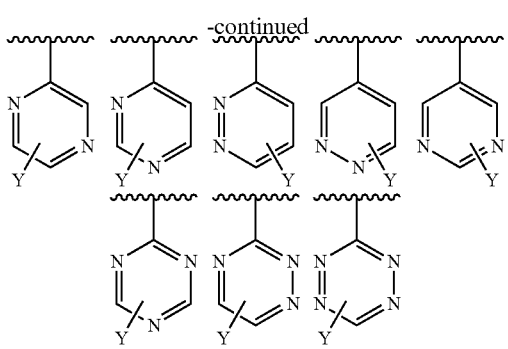

wherein X is H, $(C_1-C_6)$alkyl, or $CF_3$; and

Y is optionally present and, when Y is present, Y is 1-3 instances of a substituent selected from the group consisting of F, Cl, Br, $CF_3$, $(C_1-C_6)$alkyl, $O(C_1-C_6)$alkyl, $NH_2$, $NH(C_1-C_6)$alkyl, $N((C_1-C_6)$alkyl$)_2$, $NH-(CH_2)_j-CH_2$-Q, and

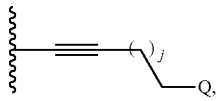

wherein j=2-6, and Q is one of the following groups

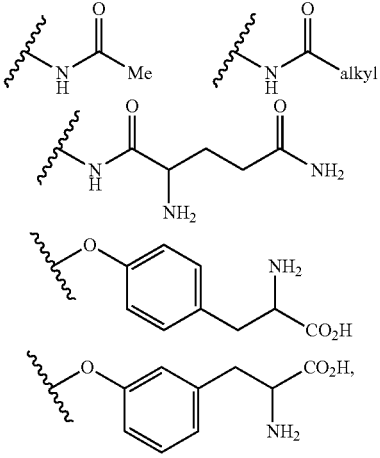

wherein a wavy line indicates a point of bonding.

When the $R^3$ group is bicyclic, the core ring system can consist of 9 or 10 atoms, with 4-10 carbon atoms, 0-6 nitrogen atoms, 0-2 oxygen atoms, and 0-2 sulfur atoms.

Representative examples of 9-atom ring systems are shown below:

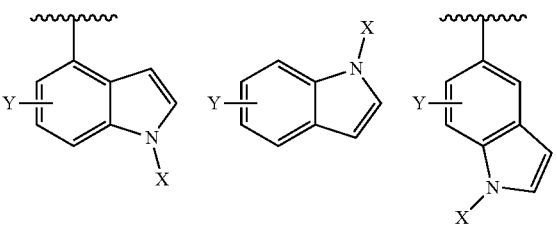

-continued
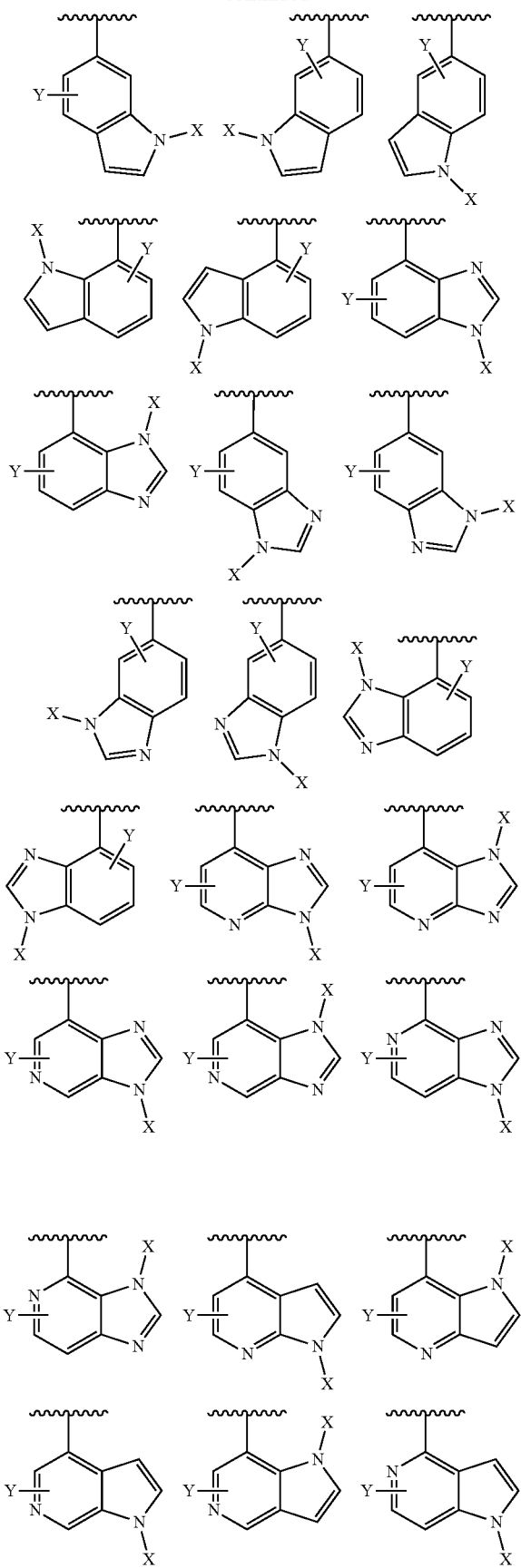
-continued
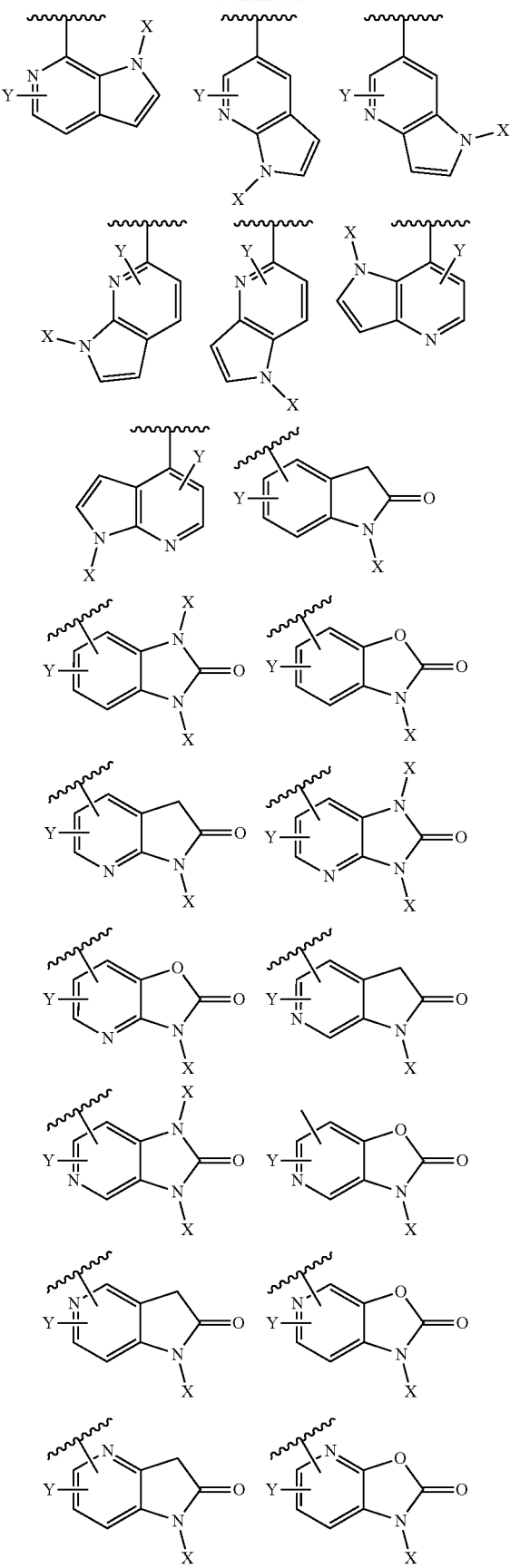

-continued
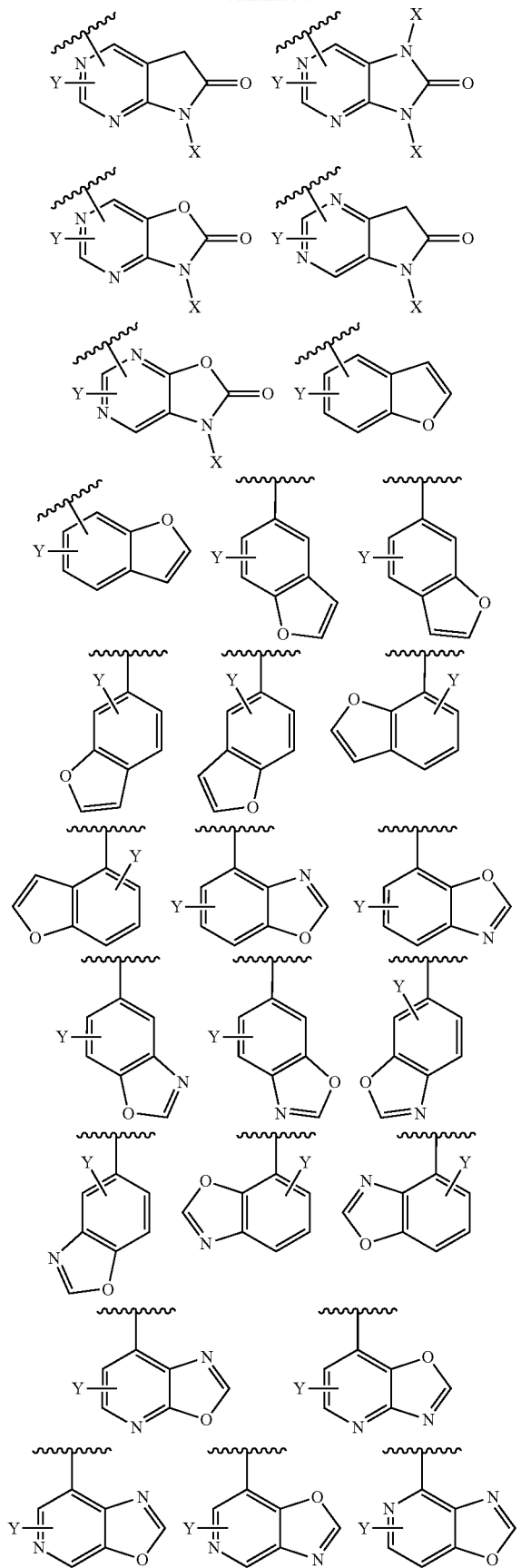
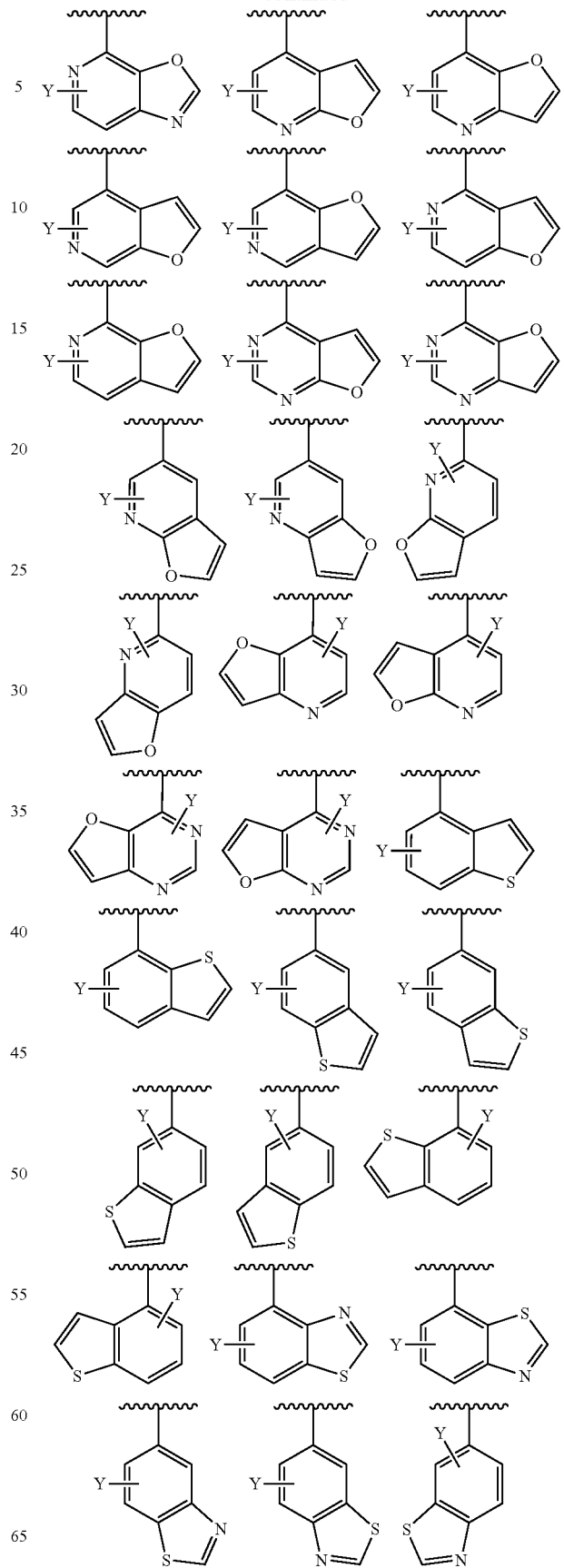

-continued

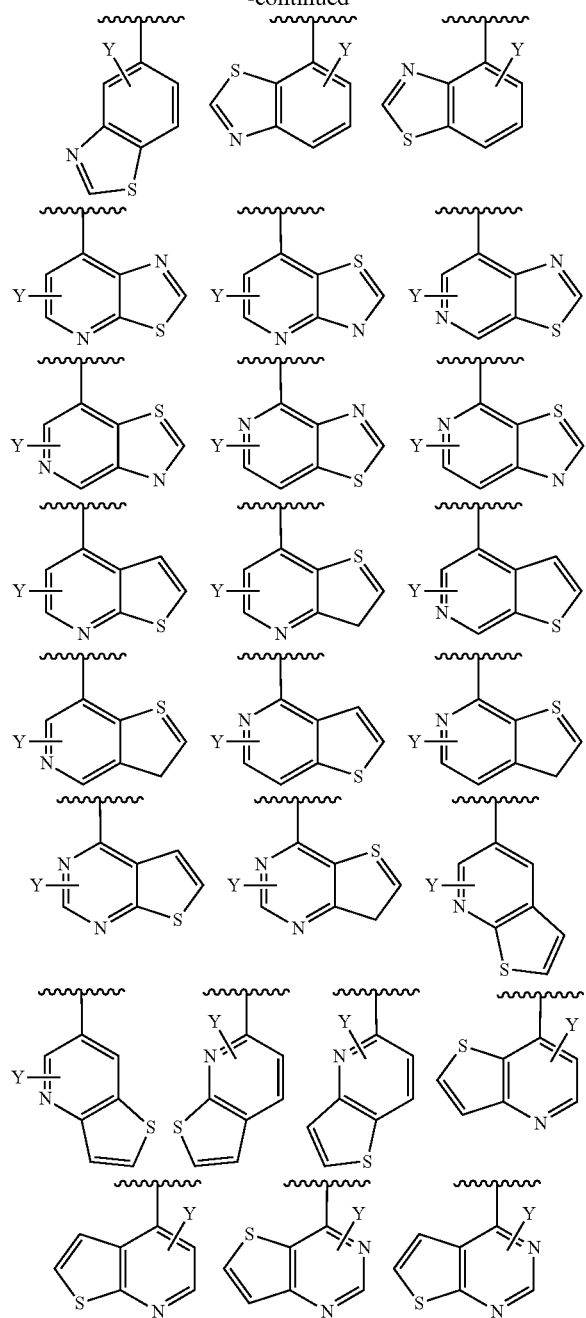

wherein the group X is H, (C$_1$-C$_6$)alkyl, or CF$_3$; and

Y is optionally present and, when Y is present, Y is 1-3 instances of a substituent selected from the group consisting of F, Cl, Br, CF$_3$, (C$_1$-C$_6$)alkyl, O(C$_1$-C$_6$)alkyl, NH$_2$, NH(C$_1$-C$_6$)alkyl, N((C$_1$-C$_6$)alkyl)$_2$, NH—(CH$_2$)$_j$—CH$_2$-Q, and

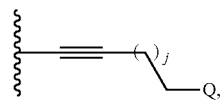

wherein j=2-6 and Q is one of the following groups

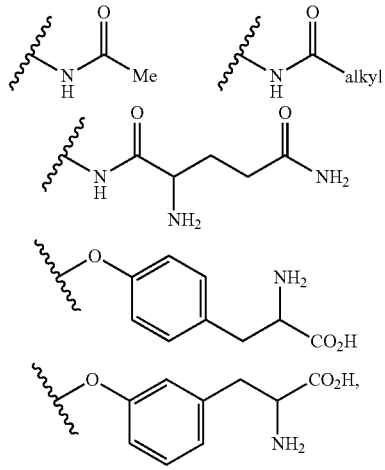

wherein a wavy line indicates a point of bonding, and wherein Y can be disposed on any ring of a multi-ring system.

Representative examples of 10-atom ring systems are shown below:

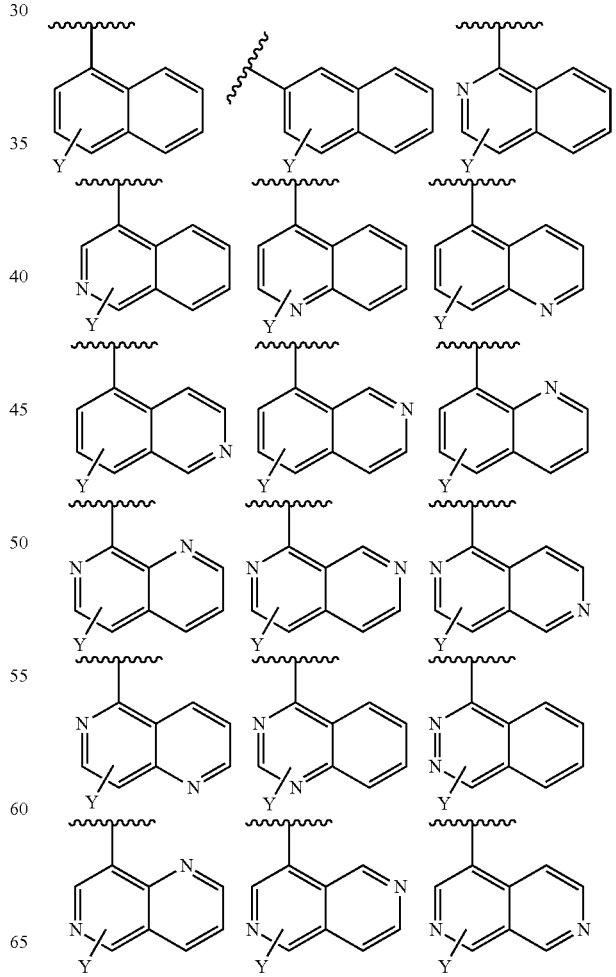

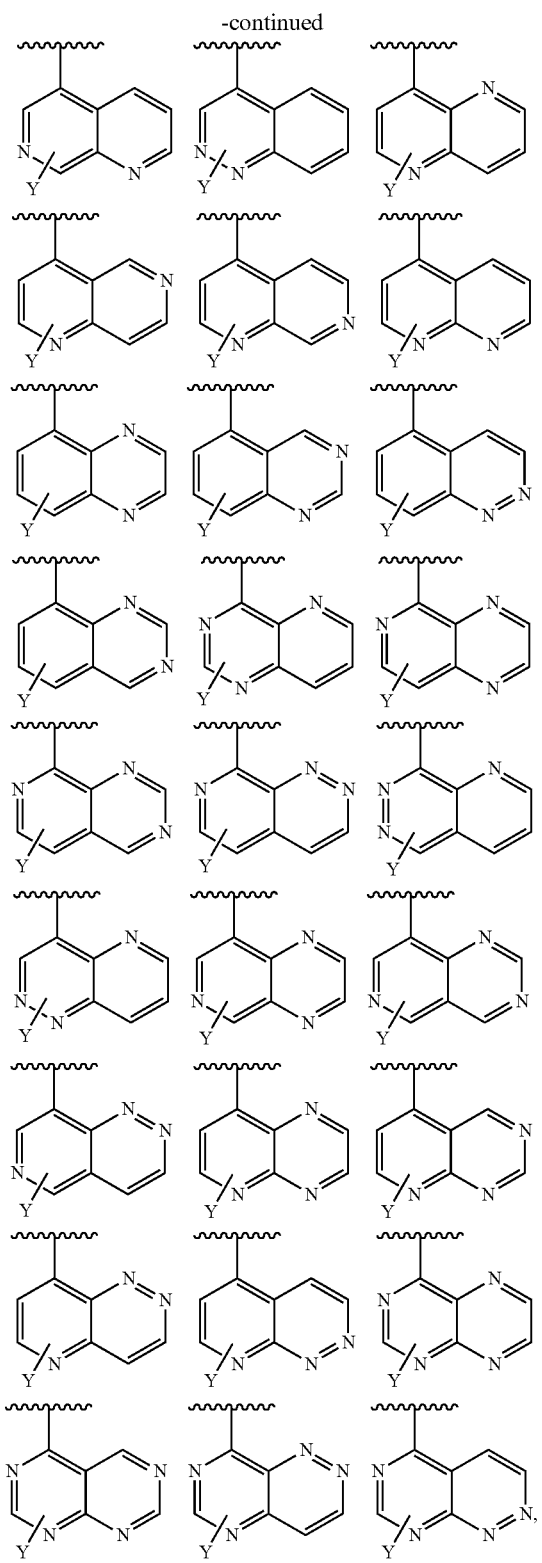

wherein the group X is H, $(C_1-C_6)$alkyl, or $CF_3$; and

Y is optionally present and, when Y is present, Y is 1-3 instances of a substituent selected from the group consisting of F, Cl, Br, $CF_3$, $(C_1-C_6)$alkyl, $O(C_1-C_6)$alkyl, $NH_2$, $NH(C_1-C_6)$alkyl, $N((C_1-C_6)$alkyl$)_2$, $NH-(CH_2)_j-CH_2$-Q, and

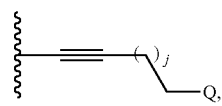

wherein j=2-6 and Q is one of the following groups

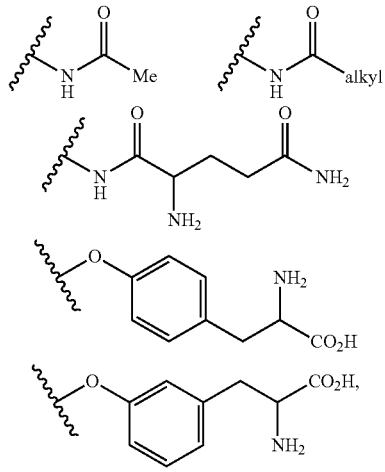

wherein a wavy line indicates a point of bonding, and wherein Y can be disposed on any ring of a multi-ring system.

More specifically, for an $R^4$ group of formula (IIC), the ring is of any one of formulas (IIC1), (IIC2), or (IIC3),

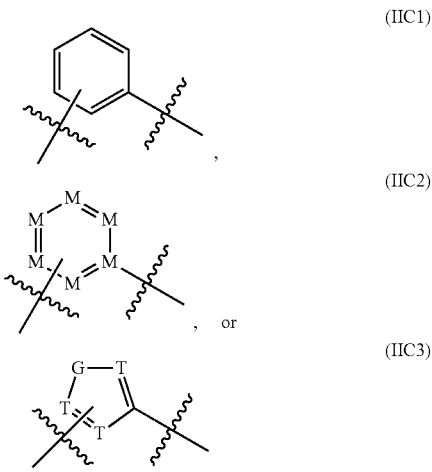

wherein wavy lines indicate points of bonding of the ring within formula (IIC);

each M is independently a carbon atom or a nitrogen atom, wherein M is a nitrogen atom in one or two instances;

G is S, O, NH, $N(C_1-C_6)$alkyl, or $N(CF_3)$;

T is independently at each occurrence a carbon atom or a nitrogen atom;

provided that when M or T is a carbon atom, that carbon atom bears a hydrogen or an $R^6$ group.

In various other embodiments, for an $R^4$ group of formula (IIC), $R^4$ is any one of formulas examples, all either cis or trans:

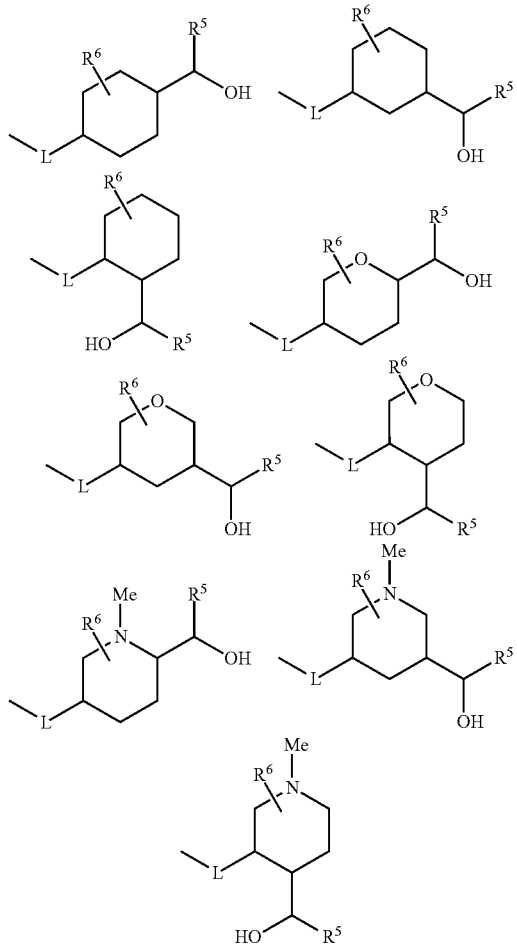

For a compound of formula (IA) of the invention, $R^2$ can be H, straight chain $(C_1-C_6)$alkyl, branched chain $(C_3-C_6)$ alkyl, $(C_3-C_7)$cycloalkyl, or $(C_1-C_6)$fluoroalkyl.

For instance, a compound of the invention can be any of the following compounds of Table 1, including all stereoisomeric forms, all isotopic forms, all crystalline and amorphous forms, and all pharmaceutically acceptable salt forms thereof:

TABLE 1

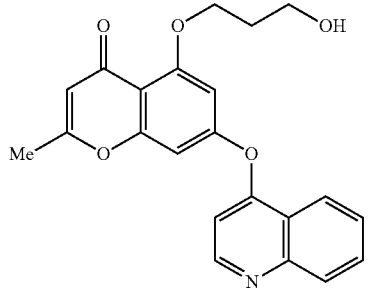 [SMILES: Cc1cc(=O)c2c(OCCCO)cc(Oc3ccnc4ccccc34)cc2o1]

1

TABLE 1-continued

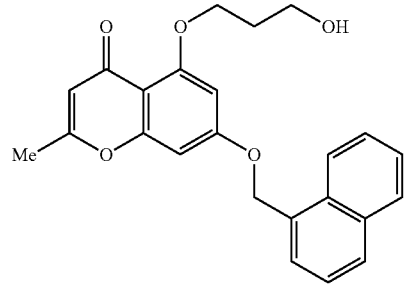 [SMILES: Cc1cc(=O)c2c(OCCCO)cc(OCc3cccc4ccccc34)cc2o1]

2

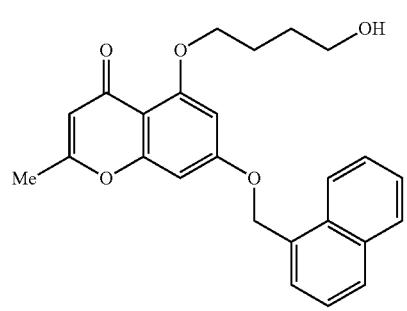 [SMILES: Cc1cc(=O)c2c(OCCCCO)cc(OCc3cccc4ccccc34)cc2o1]

3

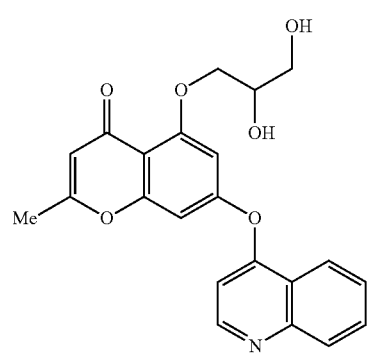 [SMILES: Cc1cc(=O)c2c(OCC(O)CO)cc(Oc3ccnc4ccccc34)cc2o1]

4

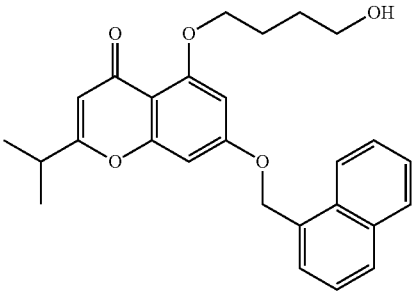 [SMILES: CC(C)c1cc(=O)c2c(OCCCCO)cc(OCc3cccc4ccccc34)cc2o1]

5

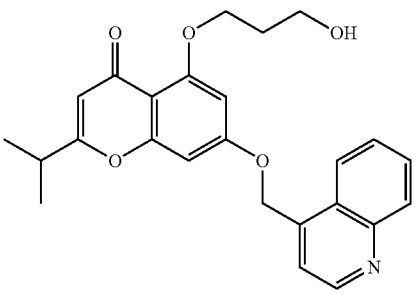

6

TABLE 1-continued
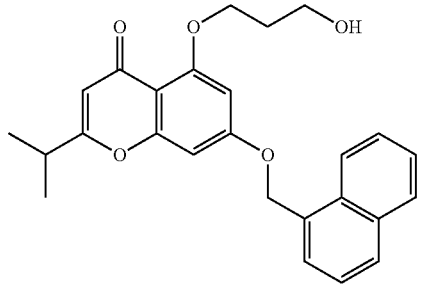 [SMILES: CC(C)c1cc(=O)c2c(OCCCO)cc(OCc3cccc4ccccc34)cc2o1] 7
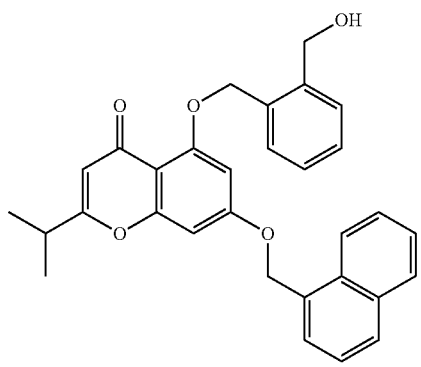 8
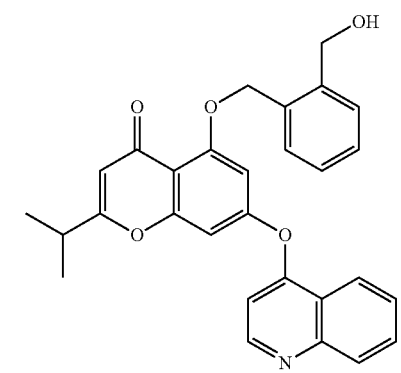 [SMILES: CC(C)c1cc(=O)c2c(OCc3ccccc3CO)cc(Oc3ccnc4ccccc34)cc2o1] 9
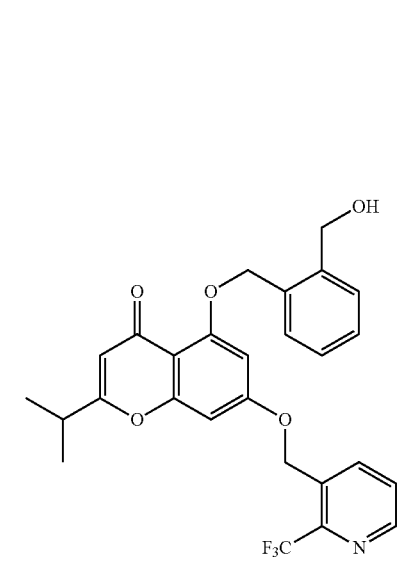 [SMILES: CC(C)c1cc(=O)c2c(OCc3ccccc3CO)cc(OCc3cccnc3C(F)(F)F)cc2o1] 10
TABLE 1-continued
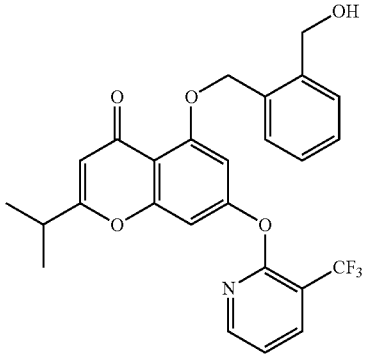 11
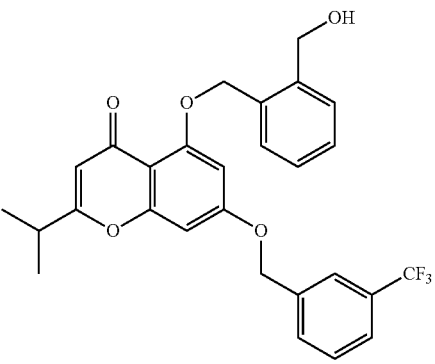 [SMILES: CC(C)c1cc(=O)c2c(OCc3ccccc3CO)cc(OCc3cccc(C(F)(F)F)c3)cc2o1] 12
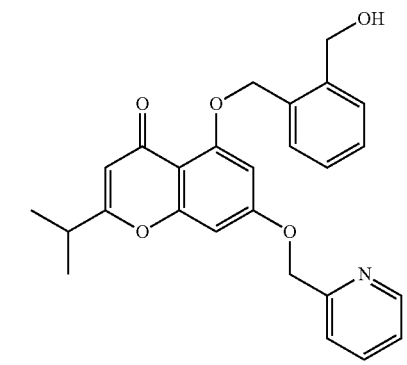 [SMILES: CC(C)c1cc(=O)c2c(OCc3ccccc3CO)cc(OCc3ccccn3)cc2o1] 13
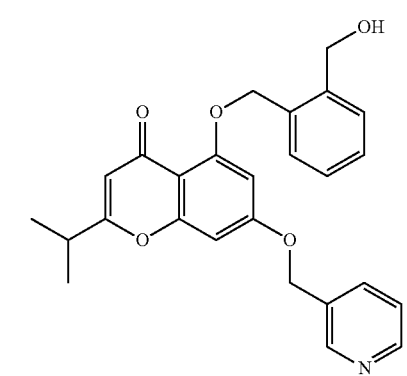 [SMILES: CC(C)c1cc(=O)c2c(OCc3ccccc3CO)cc(OCc3cccnc3)cc2o1] 14

TABLE 1-continued

TABLE 1-continued
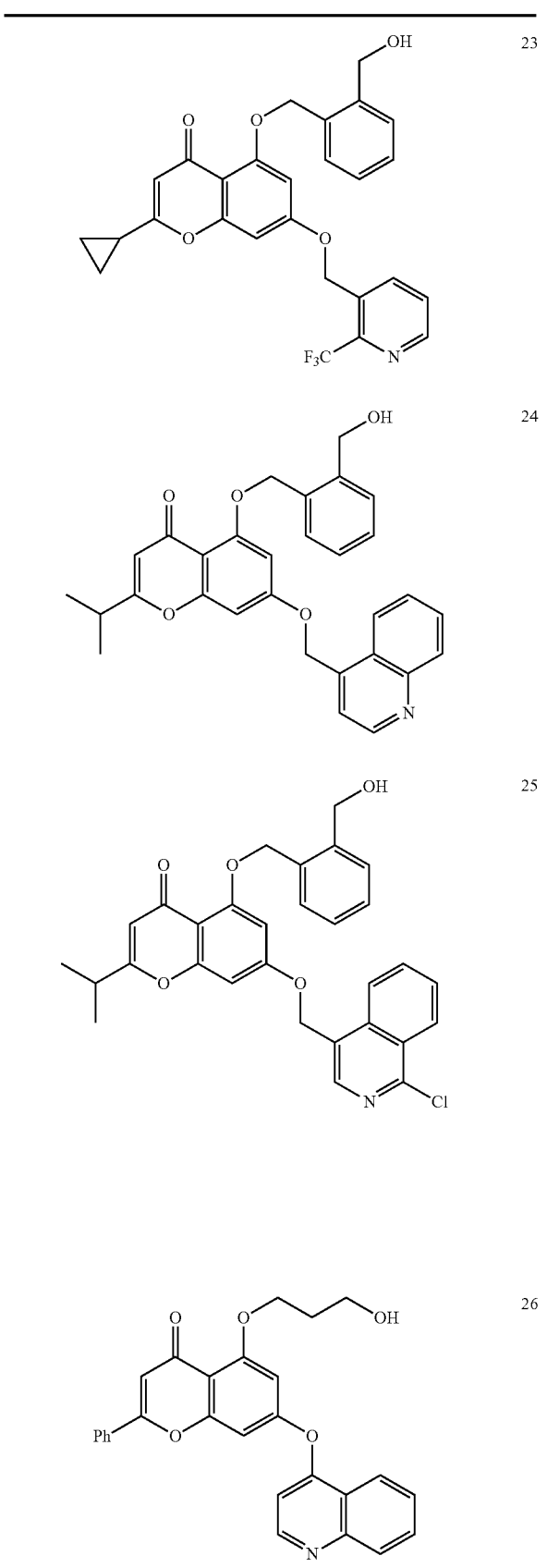
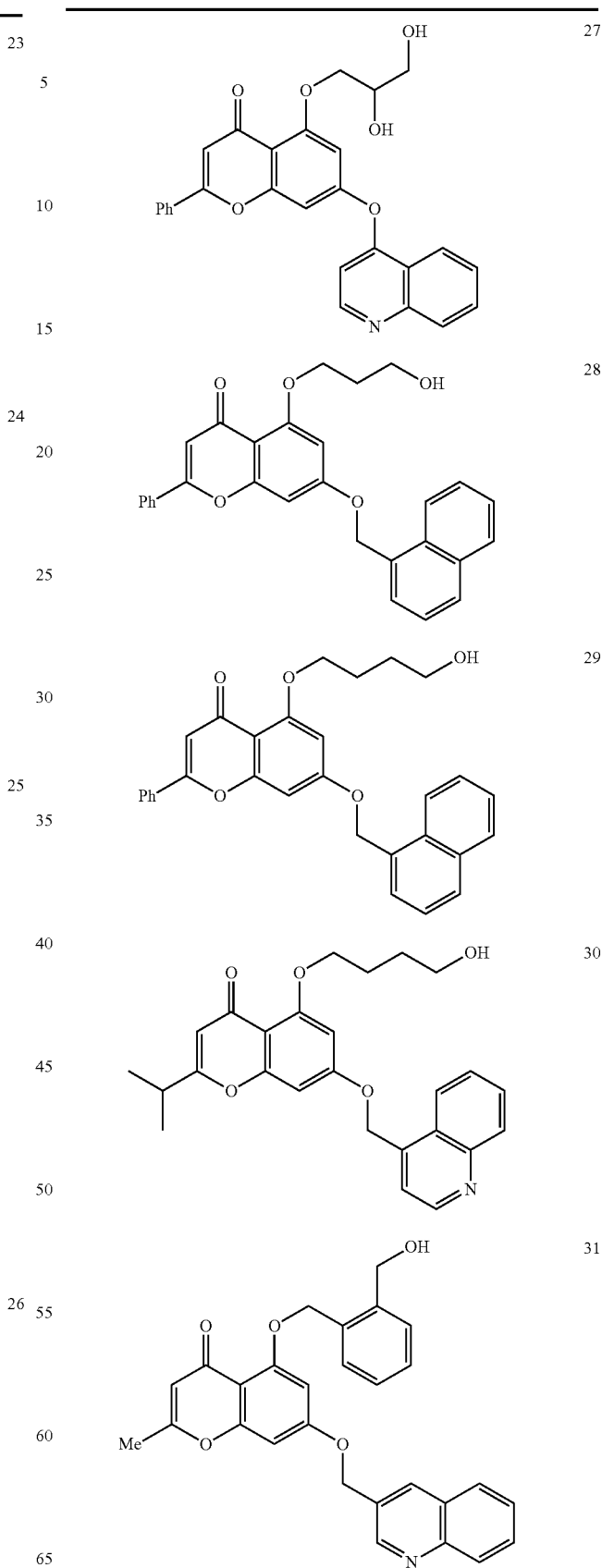

TABLE 1-continued
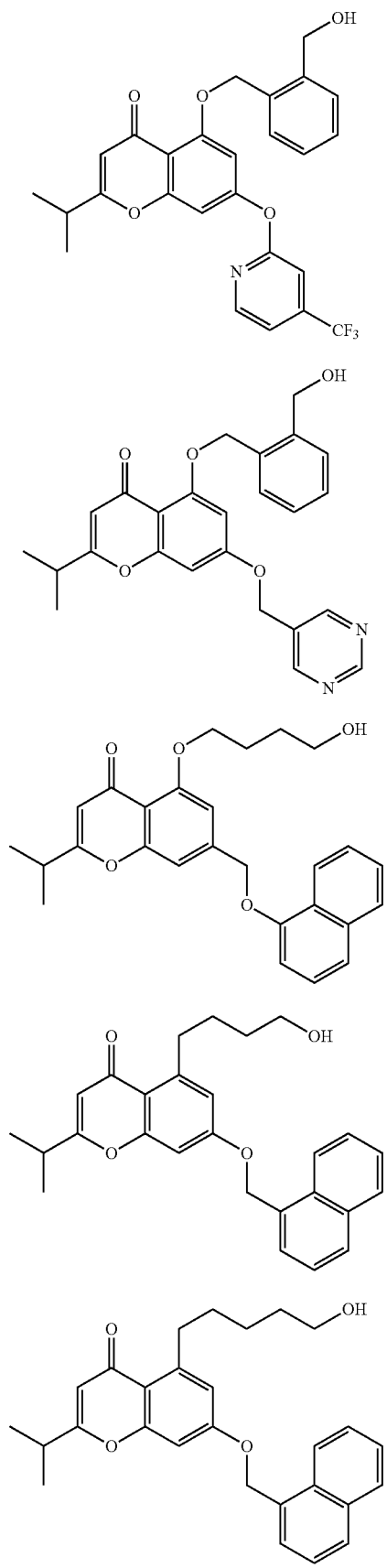
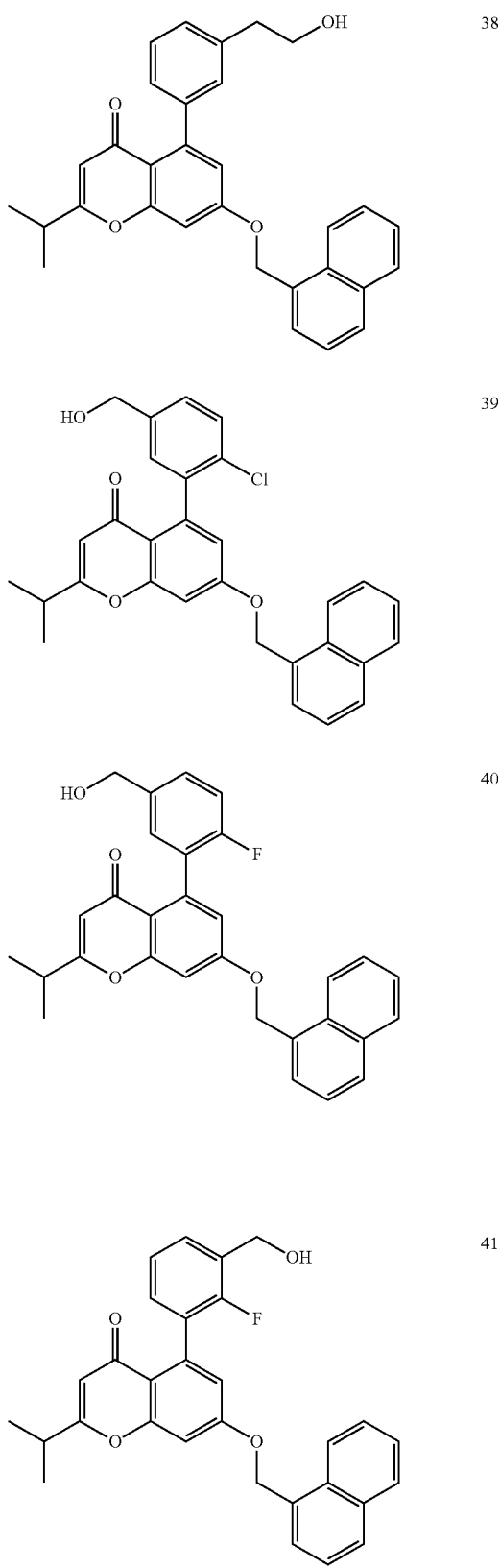

TABLE 1-continued
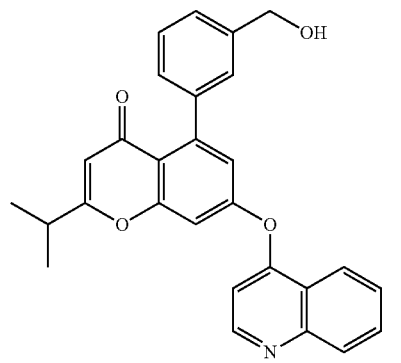 [SMILES: CC(C)c1cc(=O)c2c(-c3cccc(CO)c3)cc(Oc3ccnc4ccccc34)cc2o1] 42
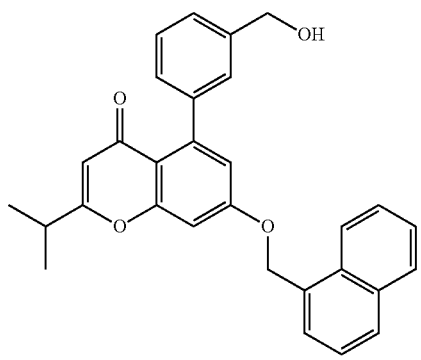 [SMILES: CC(C)c1cc(=O)c2c(-c3cccc(CO)c3)cc(OCc3cccc4ccccc34)cc2o1] 43
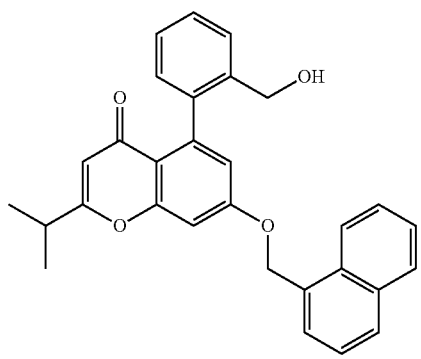 [SMILES: CC(C)c1cc(=O)c2c(-c3ccccc3CO)cc(OCc3cccc4ccccc34)cc2o1] 44
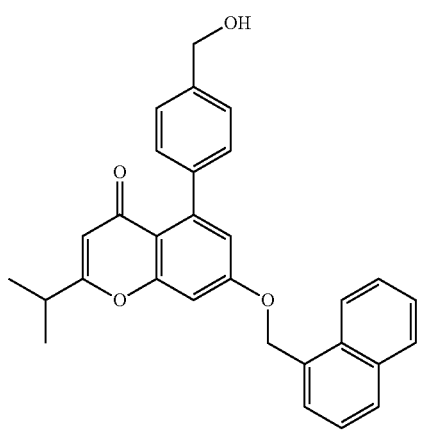 [SMILES: CC(C)c1cc(=O)c2c(-c3ccc(CO)cc3)cc(OCc3cccc4ccccc34)cc2o1] 45
TABLE 1-continued
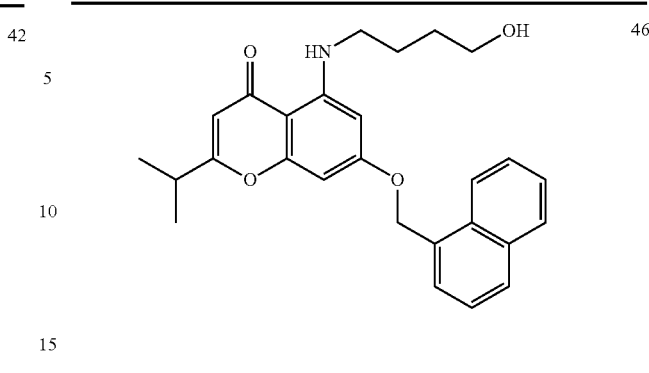 46
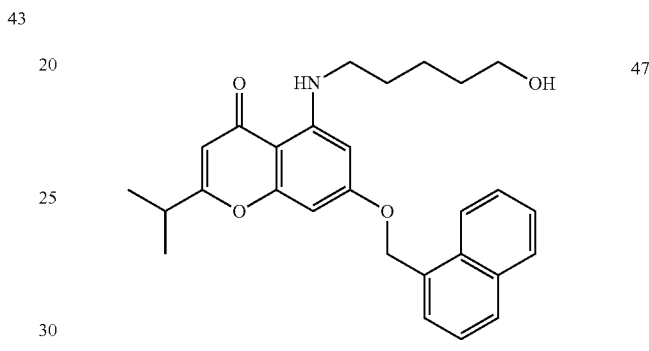 47
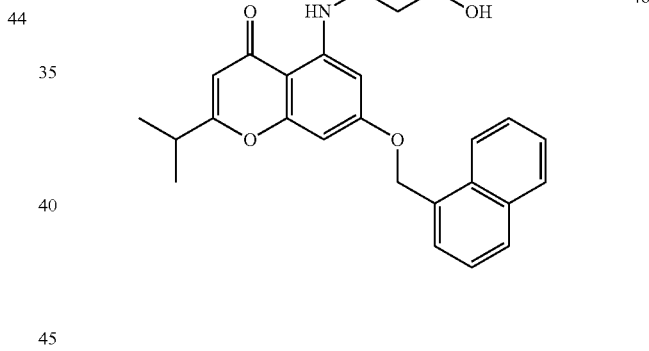 48
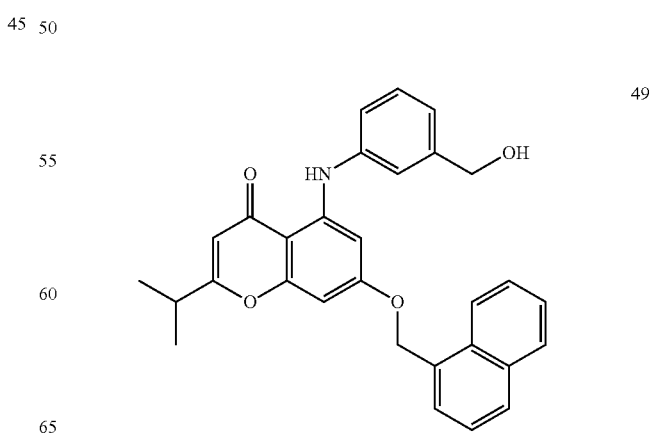 49

TABLE 1-continued

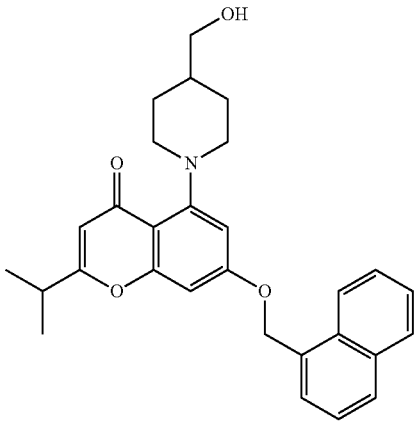 [SMILES: CC(C)c1cc(=O)c2c(N3CCC(CO)CC3)cc(OCc3cccc4ccccc34)cc2o1]

50

The invention further provides a pharmaceutical composition comprising a compound of the invention and a pharmaceutically acceptable excipient.

Nomenclature of the Scaffold, Including Numbering System:

The general scaffold type is termed a "chromenone" or a "4-chromenone" after the parent structure shown in structure 1 (Table 2). The numbering system for the chromenone ring system is indicted in structure 2. The scaffold is structurally related to, but unless $R^2$=Ph it is distinct from, the flavone family of natural products, of which structure 3 is the parent member. All flavones bear a phenyl group at the 2-position of the chromenone ring system, and most members of the family are polyhydroxylated. Appropriately-substituted flavonoids have been reported to be MCT inhibitors,[33,34] including the natural product luteolin (4), but multiple phenol groups are essential for activity, as evidenced by the finding that analogs with O-methylation in the C-2 phenyl ring or with only one hydroxyl group in this ring are significantly less active,[33] Hydroxylated analogs of flavone do not fall within the claims of this invention.

TABLE 2

Chromenone numbering system and relationship to natural flavonoids

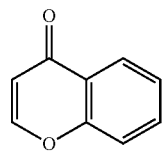

1

4H-chromen-4-one

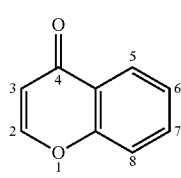

2 scaffold numbering convention

TABLE 2-continued

Chromenone numbering system and relationship to natural flavonoids

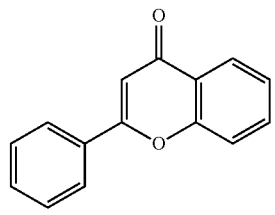

3 flavone

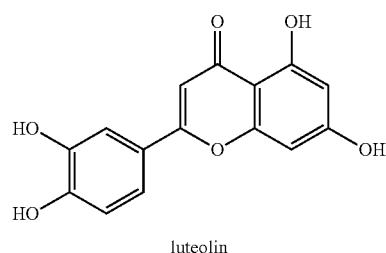 [SMILES: O=c1cc(-c2ccc(O)c(O)c2)oc2cc(O)cc(O)c12]

4 luteolin

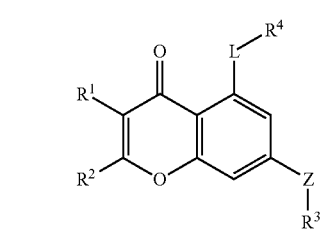

A this invention

CHEMISTRY METHODS

All reactions were performed in flame-dried glassware fitted with rubber septa under positive pressure of nitrogen or argon, unless otherwise noted. Tetrahydrofuran, DMF, acetonitrile, and methylene chloride were purchased from Aldrich and used as received.

Commercially available reagents were used without further purification. Thin layer chromatography (TLC) analyses were performed on pre-coated 250 μM silica 60 F254 glass-backed plates. Flash chromatography was performed on pre-packed columns of silica gel (230-400 mesh, 40-63 μm) by CombiFlash with EA/hexane or MeOH/DCM as eluents. Preparative HPLC was performed on a Shimadzu LC-8A preparative HPLC instrument on SunFire $C_{18}$ OBD 10 μm (30×250 mm) with $CH_3CN$+50% MeOH/$H_2O$+0.1% TFA as eluents to purify the targeted compounds. LC-MS was performed on Agilent Technologies 1200 series analytical HPLC instrument paired with a 6140 quadrupole mass spectrometer or with a Thermo Scientific UltiMate 3000 mass spectrometer. Analytical HPLC was performed on Agilent technologies 1200 series with $CH_3CN$ (Solvent B)/$H_2O$+0.9% $CH_3CN$+0.1% TFA (solvent A) as eluents, and the targeted products were detected by UV in the detection range of 215-310 nm. $^1H$ and $^{13}C$ NMR spectra were recorded on a Bruker NMR spectrometer at 400 MHz ($^1H$) or 100 MHz ($^{13}C$). Unless otherwise specified, $CDCl_3$ was used as the NMR solvent. Resonances were reported in parts per million downfield from TMS standard, and were referenced to either the residual solvent peak (typically $^1H$: $CHCl_3$ δ 7.27; $^{13}C$: $CDCl_3$ δ 77.23).

EXAMPLES

Compounds of the invention can be made by the procedure outlined in General Scheme 1:

Synthetic Scheme 1

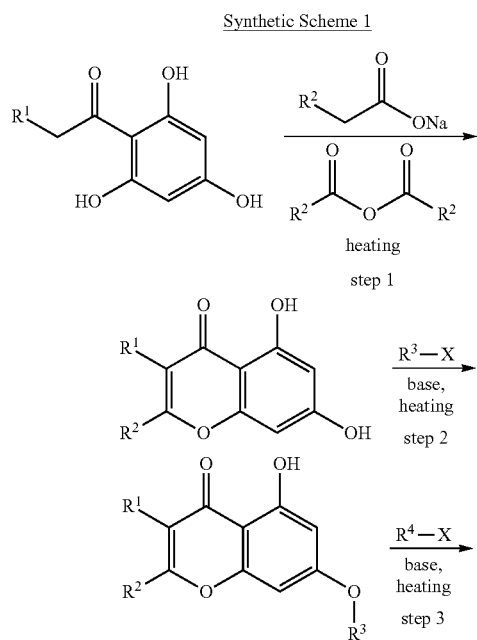

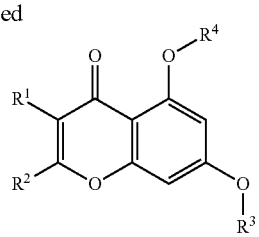

The following compounds of formula IA were made according to the methods of Synthetic Scheme 1:

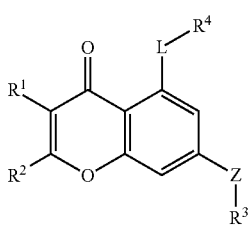

TABLE 3

| example | chemical structure | groups present |
| --- | --- | --- |
| 1 | (2-Me chromone with 5-O-(CH2)3-OH and 7-O-quinolin-4-yl) | $R^1$ = H, $R^2$ = Me, Z = O, L = O, $R^3$ = quinolin-4-yl wherein Y = H, $R^4$ = formula (IIA) wherein $R^5$ = $R^6$ = H, n = 1 |
| 2 | (2-Me chromone with 5-O-(CH2)3-OH and 7-OCH2-naphthalen-1-yl) | $R^1$ = H, $R^2$ = Me, Z = $OCH_2$, L = O, $R^3$ = naphthalen-1-yl wherein Y = H, $R^4$ = formula (IIA) wherein $R^5$ = $R^6$ = H, n = 1 |

TABLE 3-continued

| example | chemical structure | groups present |
|---|---|---|
| 3 | 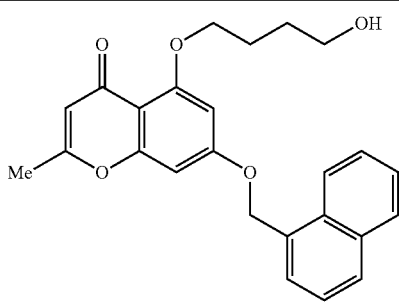 | $R^1$ = H, $R^2$ = Me, Z = $OCH_2$, L = O,<br><br>$R^3$ = 1-naphthyl (Y = H)<br><br>$R^4$ = formula (IIA) wherein $R^5$ = $R^6$ = H, n = 1 |
| 4 | 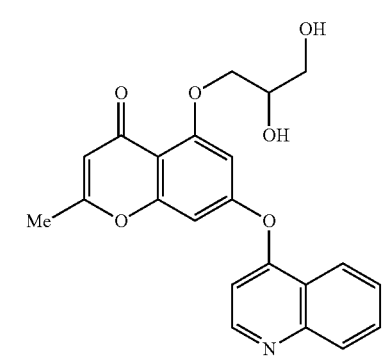 [SMILES: Cc1cc(=O)c2c(OCC(O)CO)cc(Oc3ccnc4ccccc34)cc2o1] | $R^1$ = H, $R^2$ = Me, Z = O, L = O,<br><br>$R^3$ = 4-quinolinyl (Y = H)<br><br>$R^4$ = formula (IIA) wherein $R^5$ = H, $R^6$ = OH, n = 1 |
| 5 | 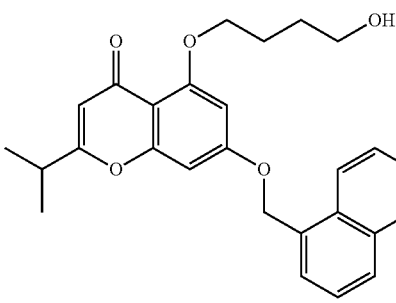 | $R^1$ = H, $R^2$ = i-Pr, Z = $OCH_2$, L = O,<br><br>$R^3$ = 1-naphthyl (Y = H)<br><br>$R^4$ = formula (IIA) wherein $R^5$ = $R^6$ = H, n = 2 |
| 6 | 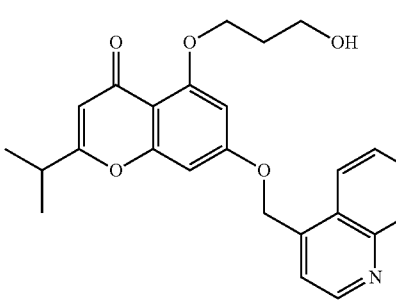 | $R^1$ = H, $R^2$ = i-Pr, Z = $OCH_2$, L = O,<br><br>$R^3$ = 4-quinolinyl (Y = H)<br><br>$R^4$ = formula (IIA) wherein $R^5$ = $R^6$ = H, n = 1 |
| 7 | 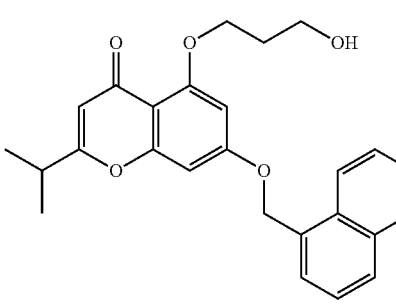 | $R^1$ = H, $R^2$ = i-Pr, Z = $OCH_2$, L = O,<br><br>$R^3$ = 1-naphthyl (Y = H)<br><br>$R^4$ = formula (IIA) wherein $R^5$ = $R^6$ = H, n = 1 |

TABLE 3-continued

| example | chemical structure | groups present |
|---|---|---|
| 8 | 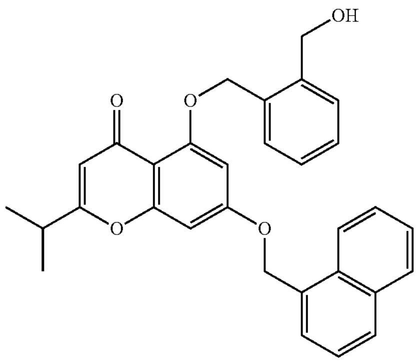 [SMILES: CC(C)c1cc(=O)c2c(OCc3ccccc3CO)cc(OCc3cccc4ccccc34)cc2o1] | $R^1$ = H, $R^2$ = i-Pr, Z = OCH$_2$, L = O, $R^3$ = 1-naphthyl (Y = H), $R^4$ = formula (IIC) wherein $R^5 = R^6$ = H, n = 0, ring = phenyl |
| 9 | 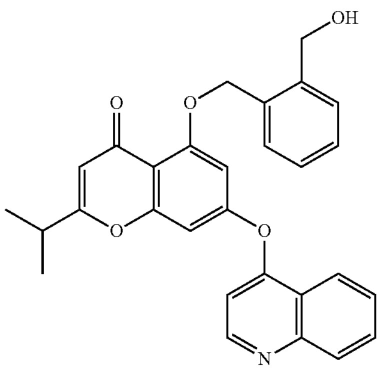 [SMILES: CC(C)c1cc(=O)c2c(OCc3ccccc3CO)cc(Oc3ccnc4ccccc34)cc2o1] | $R^1$ = H, $R^2$ = i-Pr, Z = O, L = O, $R^3$ = 4-quinolinyl (Y = H), $R^4$ = formula (IIC) wherein $R^5 = R^6$ = H, n = 0, ring = phenyl |
| 10 | 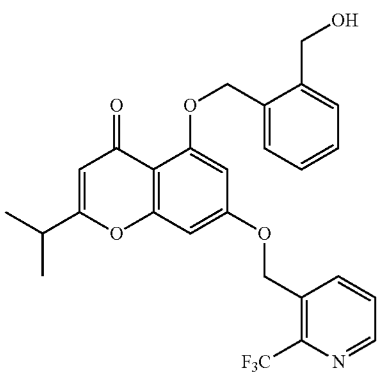 [SMILES: CC(C)c1cc(=O)c2c(OCc3ccccc3CO)cc(OCc3cccnc3C(F)(F)F)cc2o1] | $R^1$ = H, $R^2$ = i-Pr, Z = OCH$_2$, L = O, $R^3$ = 3-pyridinyl (Y = CF$_3$), $R^4$ = formula (IIC) wherein $R^5 = R^6$ = H, n = 0, ring = phenyl |
| 11 | 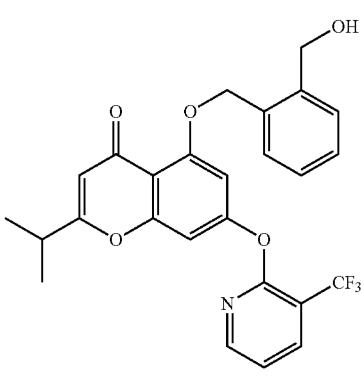 [SMILES: CC(C)c1cc(=O)c2c(OCc3ccccc3CO)cc(Oc3ncccc3C(F)(F)F)cc2o1] | $R^1$ = H, $R^2$ = i-Pr, Z = O, L = O, $R^3$ = 2-pyridinyl (Y = CF$_3$), $R^4$ = formula (IIC) wherein $R^5 = R^6$ = H, n = 0, ring = phenyl |

TABLE 3-continued

| example | chemical structure | groups present |
|---|---|---|
| 12 | 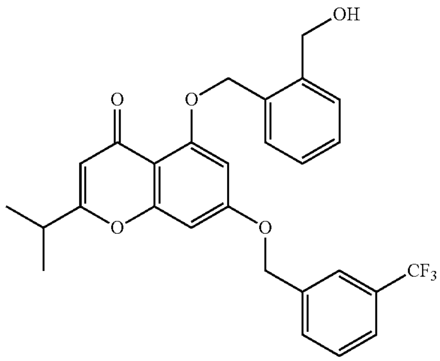 [SMILES: CC(C)c1cc(=O)c2c(OCc3ccccc3CO)cc(OCc3cccc(C(F)(F)F)c3)cc2o1] | $R^1$ = H, $R^2$ = i-Pr, Z = $OCH_2$, L = O,<br><br>$R^3$ = $Y\text{-phenyl}$ wherein Y = $CF_3$,<br><br>$R^4$ = formula (IIC) wherein $R^5$ = $R^6$ = H, n = 0<br>ring = phenyl |
| 13 | 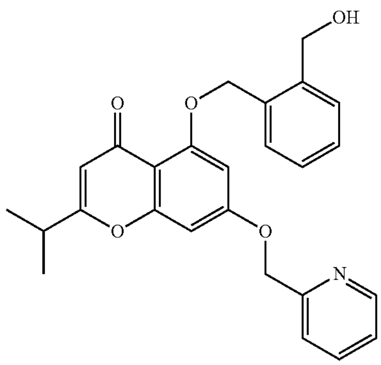 [SMILES: CC(C)c1cc(=O)c2c(OCc3ccccc3CO)cc(OCc3ccccn3)cc2o1] | $R^1$ = H, $R^2$ = i-Pr, Z = $OCH_2$, L = O,<br><br>$R^3$ = $Y\text{-pyridyl}$ wherein Y = H,<br><br>$R^4$ = formula (IIC) wherein $R^5$ = $R^6$ = H, n = 0<br>ring = phenyl |
| 14 | 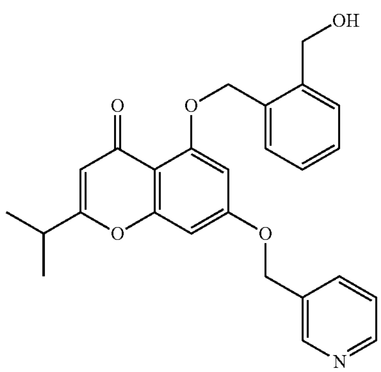 [SMILES: CC(C)c1cc(=O)c2c(OCc3ccccc3CO)cc(OCc3cccnc3)cc2o1] | $R^1$ = H, R2 = i-Pr, Z = $OCH_2$, L = O,<br><br>$R^3$ = $Y\text{-pyridyl}$ wherein Y = H,<br><br>$R^4$ = formula (IIC) wherein $R^5$ = $R^6$ = H, n = 0<br>ring = phenyl |
| 15 | 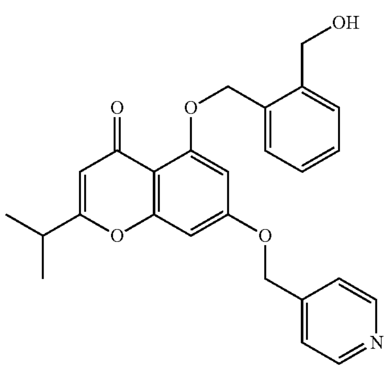 | $R^1$ = H, R2 = i-Pr, Z = $OCH_2$, L = O,<br><br>$R^3$ = $Y\text{-pyridyl}$ wherein Y = H,<br><br>$R^4$ = formula (IIC) wherein $R^5$ = $R^6$ = H, n = 0<br>ring = phenyl |

TABLE 3-continued

| example | chemical structure | groups present |
|---|---|---|
| 16 | 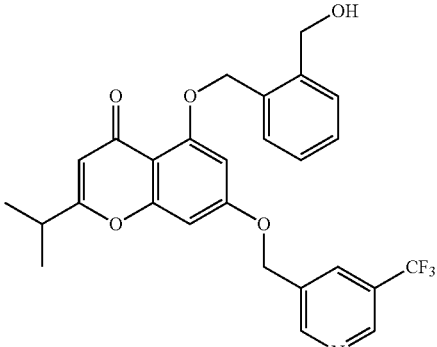 | $R^1$ = H, R2 = i-Pr, Z = OCH$_2$, L = O,<br>$R^3$ = 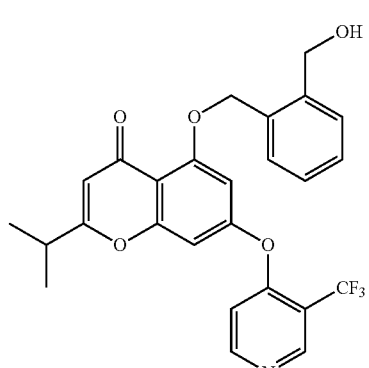 wherein Y = CF$_3$,<br>$R^4$ = formula (IIC) wherein $R^5$ = $R^6$ = H, n = 0<br>ring = phenyl |
| 17 | 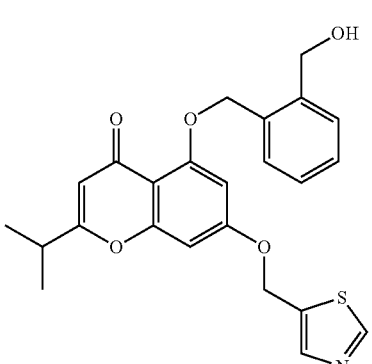 | $R^1$ = H, $R^2$ = i-Pr, Z = O, L = O,<br>$R^3$ = 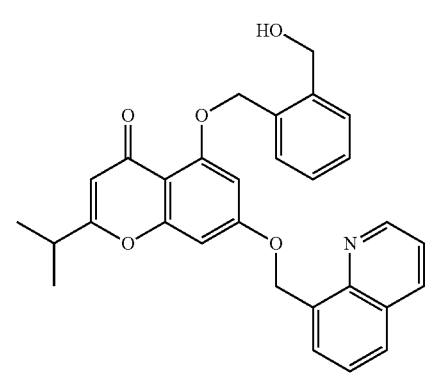 wherein Y = CF$_3$,<br>$R^4$ = formula (IIC) wherein $R^5$ = $R^6$ = H, n = 0<br>ring = phenyl |
| 18 | 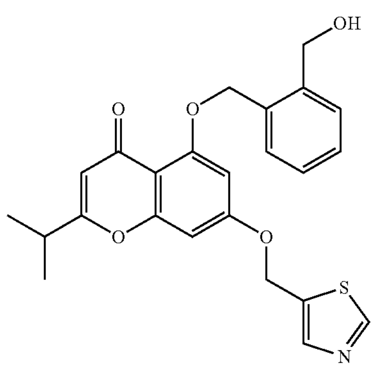 [SMILES: CC(C)c1cc(=O)c2c(OCc3ccccc3CO)cc(OCc3cncs3)cc2o1] | $R^1$ = H, $R^2$ = i-Pr, Z = OCH$_2$, L = O,<br>$R^3$ = wherein Y = H,<br>$R^4$ = formula (IIC) wherein $R^5$ = $R^6$ = H, n = 0<br>ring = phenyl |
| 19 | 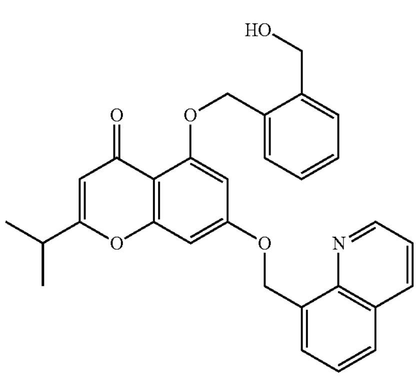 [SMILES: CC(C)c1cc(=O)c2c(OCc3ccccc3CO)cc(OCc3cccc4cccnc34)cc2o1] | $R^1$ = H, $R^2$ = i-Pr, Z = OCH$_2$, L = O,<br>$R^3$ = wherein Y = H,<br>$R^4$ = formula (IIC) wherein $R^5$ = $R^6$ = H, n = 0<br>ring = phenyl |

TABLE 3-continued

| example | chemical structure | groups present |
|---|---|---|
| 20 | 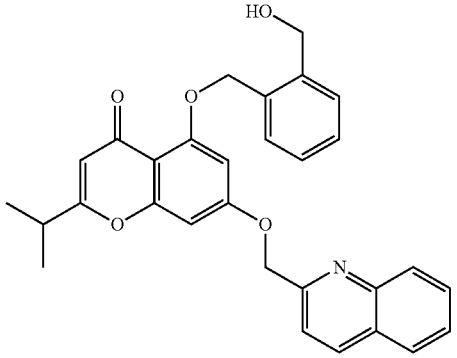 [SMILES: CC(C)c1cc(=O)c2c(OCc3ccccc3CO)cc(OCc3ccc4ccccc4n3)cc2o1] | $R^1$ = H, $R^2$ = i-Pr, Z = $OCH_2$, L = O,<br><br>$R^3$ = 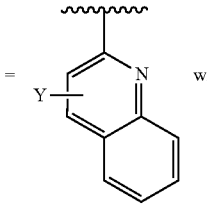 wherein Y = H,<br><br>$R^4$ = formula (IIC) wherein $R^5$ = $R^6$ = H, n = 0<br>ring = phenyl |
| 21 | 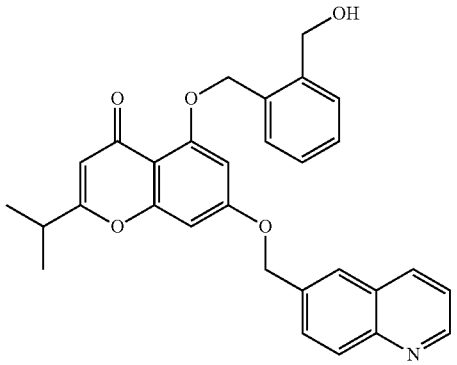 [SMILES: CC(C)c1cc(=O)c2c(OCc3ccccc3CO)cc(OCc3ccc4ncccc4c3)cc2o1] | $R^1$ = H, $R^2$ = i-Pr, Z = $OCH_2$, L = O,<br><br>$R^3$ = 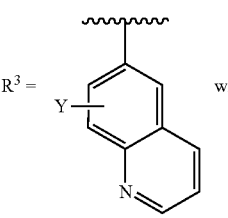 wherein Y = H,<br><br>$R^4$ = formula (IIC) wherein $R^5$ = $R^6$ = H, n = 0<br>ring = phenyl |
| 22 | 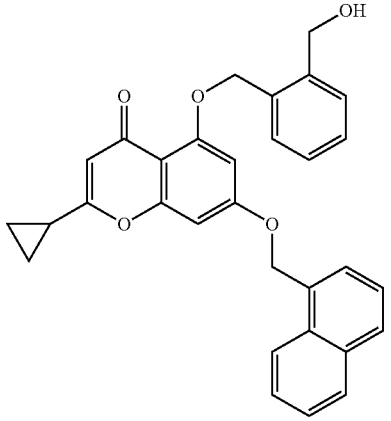 [SMILES: O=c1cc(C2CC2)oc2cc(OCc3cccc4ccccc34)cc(OCc3ccccc3CO)c12] | $R^1$ = H, $R^2$ = cyclopropyl, Z = $OCH_2$, L = O,<br><br>$R^3$ = 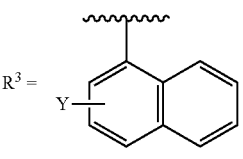 wherein Y = H,<br><br>$R^4$ = formula (IIC) wherein $R^5$ = $R^6$ = H, n = 0<br>ring = phenyl |
| 23 | 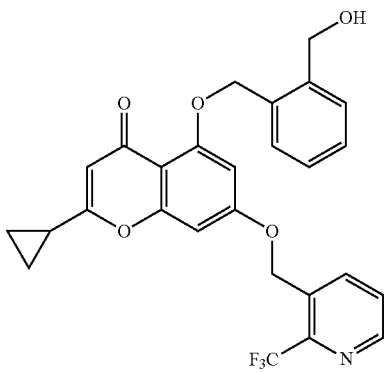 [SMILES: O=c1cc(C2CC2)oc2cc(OCc3cccnc3C(F)(F)F)cc(OCc3ccccc3CO)c12] | $R^1$ = H, $R^2$ = i-Pr, Z = $OCH_2$, L = O,<br><br>$R^3$ = 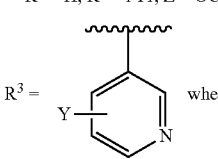 wherein Y = $CF_3$,<br><br>$R^4$ = formula (IIC) wherein $R^5$ = $R^6$ = H, n = 0<br>ring = phenyl |

TABLE 3-continued

| example | chemical structure | groups present |
|---|---|---|
| 24 | 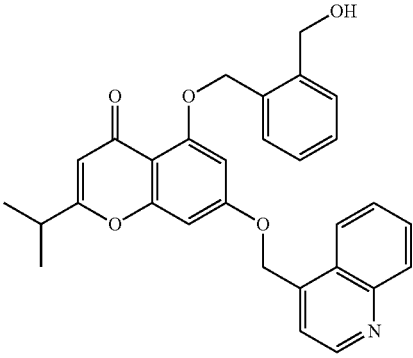 [SMILES: CC(C)c1cc(=O)c2c(OCc3ccccc3CO)cc(OCc3ccnc4ccccc34)cc2o1] | $R^1$ = H, $R^2$ = i-Pr, Z = $OCH_2$, L = O,<br><br>$R^3$ = 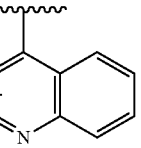 wherein Y = H,<br><br>$R^4$ = formula (IIC) wherein $R^5$ = $R^6$ = H, n = 0<br>ring = phenyl |
| 25 | 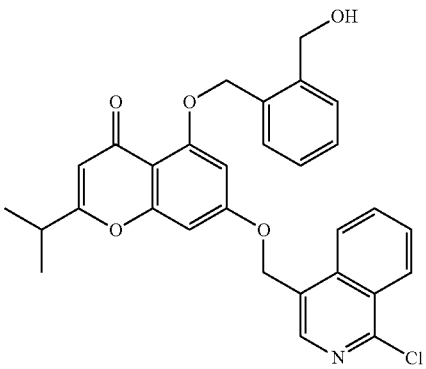 [SMILES: CC(C)c1cc(=O)c2c(OCc3ccccc3CO)cc(OCc3cnc(Cl)c4ccccc34)cc2o1] | $R^1$ = H, $R^2$ = i-Pr, Z = $OCH_2$, L = O,<br><br>$R^3$ = 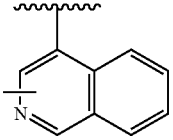 wherein Y = Cl at C1,<br><br>$R^4$ = formula (IIC) wherein $R^5$ = $R^6$ = H, n = 0<br>ring = phenyl |
| 26 | 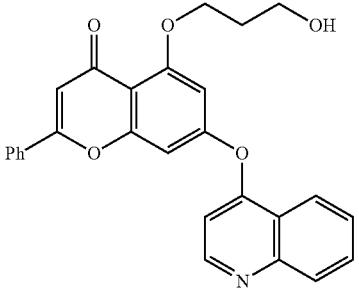 [SMILES: O=c1cc(-c2ccccc2)oc2cc(Oc3ccnc4ccccc34)cc(OCCCO)c12] | $R^1$ = H, $R^2$ = Ph, Z = O, L = O,<br><br>$R^3$ = 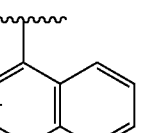 wherein Y = H,<br><br>$R^4$ = formula (IIA) wherein $R^5$ = $R^6$ = H, n = 1 |
| 27 | 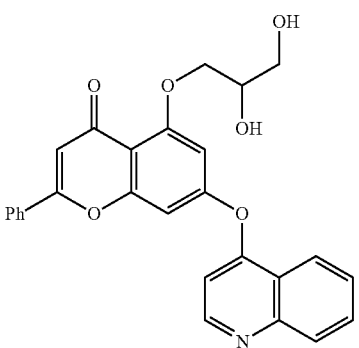 [SMILES: O=c1cc(-c2ccccc2)oc2cc(Oc3ccnc4ccccc34)cc(OCC(O)CO)c12] | $R^1$ = H, $R^2$ = Ph, Z = O, L = O,<br><br>$R^3$ = 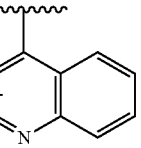 wherein Y = H,<br><br>$R^4$ = formula (IIA) wherein $R^5$ = H, $R^6$ = OH, n = 0 |

TABLE 3-continued

| example | chemical structure | groups present |
|---|---|---|
| 28 | 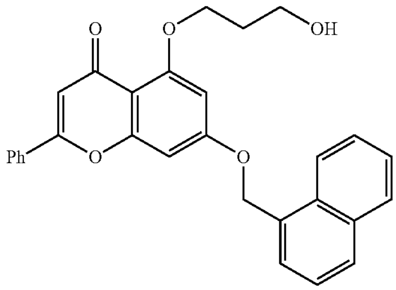 [SMILES: O=c1cc(-c2ccccc2)oc2cc(OCc3cccc4ccccc34)cc(OCCCO)c12] | $R^1$ = H, $R^2$ = Ph, Z = $OCH_2$, L = O,<br><br>$R^3$ = (1-naphthyl, Y attached) wherein Y = H,<br><br>$R^4$ = formula (IIA) wherein $R^5$ = $R^6$ = H, n = 1 |
| 29 | 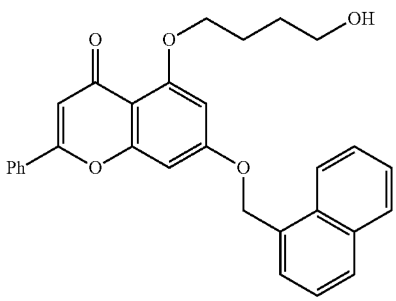 [SMILES: O=c1cc(-c2ccccc2)oc2cc(OCc3cccc4ccccc34)cc(OCCCCO)c12] | $R^1$ = H, $R^2$ = Ph, Z = $OCH_2$, L = O,<br><br>$R^3$ = (1-naphthyl, Y attached) wherein Y = H,<br><br>$R^4$ = formula (IIA) wherein $R^5$ = $R^6$ = H, n = 2 |
| 30 | 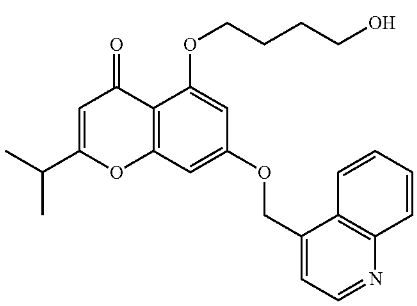 [SMILES: CC(C)c1cc(=O)c2c(OCCCCO)cc(OCc3ccnc4ccccc34)cc2o1] | $R^1$ = H, $R^2$ = i-Pr, Z = $OCH_2$, L = O,<br><br>$R^3$ = (4-quinolinyl, Y attached) wherein Y = H,<br><br>$R^4$ = formula (IIA) wherein $R^5$ = $R^6$ = H, n = 2 |
| 31 | 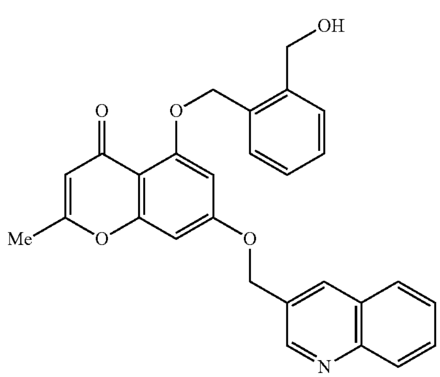 [SMILES: Cc1cc(=O)c2c(OCc3ccccc3CO)cc(OCc3cnc4ccccc4c3)cc2o1] | $R^1$ = H, $R^2$ = Me, Z = O, L = O,<br><br>$R^3$ = (quinolinyl, Y attached) wherein Y = H,<br><br>$R^4$ = formula (IIC) wherein $R^5$ = $R^6$ = H, n = 0<br>ring = phenyl |

TABLE 3-continued

| example | chemical structure | groups present |
|---|---|---|
| 32 | 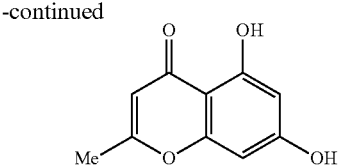 | $R^1$ = H, $R^2$ = i-Pr, Z = O, L = O, <br><br>$R^3$ = [pyridyl group] wherein Y = CF$_3$,<br><br>$R^4$ = formula (IIC) wherein $R^5$ = $R^6$ = H, n = 0<br>ring = phenyl |
| 33 | 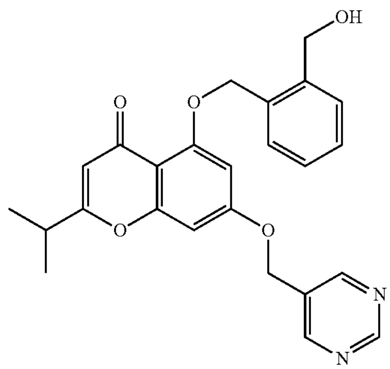 [SMILES: CC(C)c1cc(=O)c2c(OCc3ccccc3CO)cc(OCc3cncnc3)cc2o1] | $R^1$ = H, $R^2$ = i-Pr, Z = OCH$_2$, L = O,<br><br>$R^3$ = [pyrimidinyl group] wherein Y = H,<br><br>$R^4$ = formula (IIC) wherein $R^5$ = $R^6$ = H, n = 0<br>ring = phenyl |

Synthetic Procedures

Example 1

5-(3-hydroxypropoxy)-2-methyl-7-(quinolin-4-yloxy)-4H-chromen-4-one

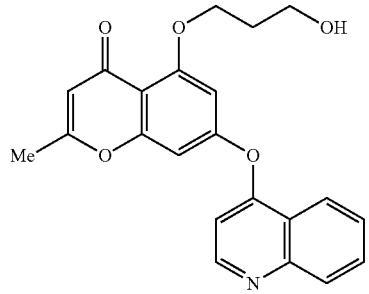 [SMILES: Cc1cc(=O)c2c(OCCCO)cc(Oc3ccnc4ccccc34)cc2o1]

Step 1.

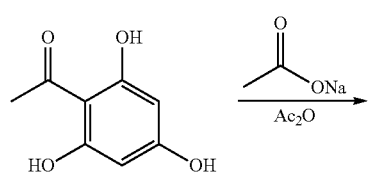

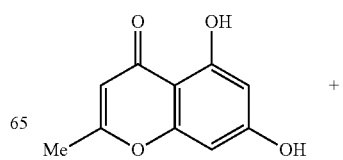

5,7-dihydro-2-methyl-4H-chromen-4-one: A mixture of 1-(2,4,6-trihydroxyphenyl)ethan-1-one (2.02 g, 12.0 mmol), AcONa (0.984 g, 12.0 mmol) in Ac$_2$O (6.0 mL) was heated at 180° C. for 40 min in a microwave reactor. The reaction mixture was poured into water, extracted with ethyl acetate (EA), washed with sat'd NaHCO$_3$ and brine, dried over Na$_2$SO$_4$, and concentrated. The residue was treated with a solution of K$_2$CO$_3$ (4.98 g, 36 mmol) in H$_2$O (90 mL) and refluxed for 3 h. Acidified with 3 N HCl. The precipitate was collected by vacuum filtration to afford 1.09 g (47%) of 5,7-dihydro-2-methyl-4H-chromen-4-one as a yellow solid. R$_f$=0.45 (hexanes:EA=1:1); LC-MS (ESI): m/z 193 [M+1]$^+$; $^1$H NMR (400 MHz, DMSO-d$_6$) δ (ppm) 2.35 (s, 3H), 6.17 (d, J=2.0 Hz, 2H), 6.33 (d, J=2.0 Hz, 1H), 10.78 (s, 1H), 12.82 (s, 1H);

Step 2.

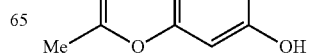

-continued

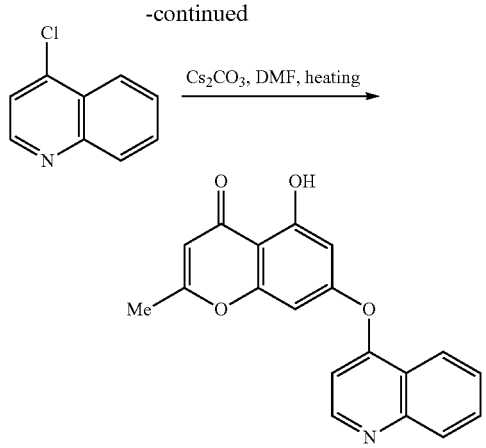

5-hydroxy-2-methyl-7-(quinolin-4-yloxy)-4H-chromen-4-one: A mixture of 5,7-dihydro-2-methyl-4H-chromen-4-one (154 mg, 0.80 mmol), 4-chloroquinoline (144 mg, 0.88 mmol), Cs$_2$CO$_3$ (782 mg, 2.40 mmol) in DMF (4.0 mL) was heated to 140° C. under N$_2$ for 40 hours. The mixture was cooled to room temperature, quenched with saturated NH$_4$Cl, extracted with ethyl acetate (EA). The combined organic extracts were washed with brine and dried over Na$_2$SO$_4$. The crude product was purified by flash column (hexanes:EA=1:1) to afford 110 mg (43%) of 5-hydroxy-2-methyl-7-(quinolin-4-yloxy)-4H-chromen-4-one as a white solid. R$_f$=0.35 (EA:hexanes=1:1); LC-MS (ESI): m/z 320 [M+1]$^+$; $^1$H NMR (400 MHz, CDCl$_3$) δ (ppm) 2.39 (s, 3H), 6.13 (s, 1H), 6.58 (dd, J=2.0, 3.6 Hz, 2H), 6.91 (d, J=4.8 Hz, 1H), 7.61 (t, J=8.0 Hz, 1H), 7.80 (t, J=8.0 Hz, 1H), 8.15 (d, J=4.4 Hz, 1H), 8.20 (d, J=4.4 Hz, 1H), 8.83 (d, J=4.8 Hz, 1H), 12.83 (s, 1H).
Step 3.

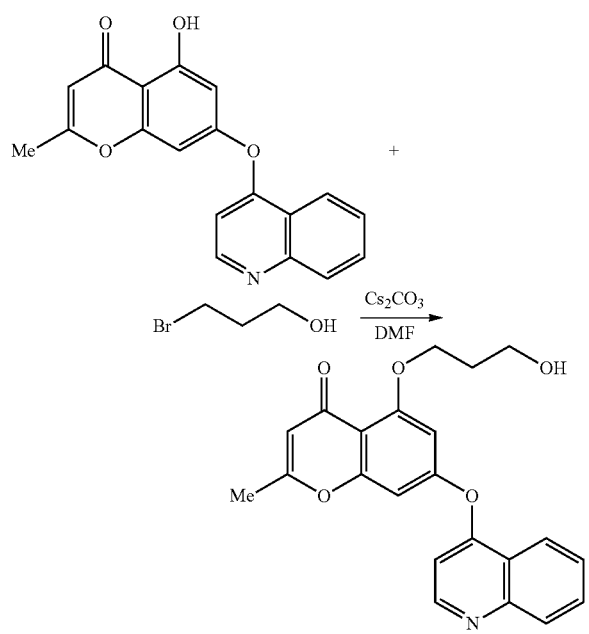

5-(3-hydroxypropoxy)-2-methyl-7-(quinolin-4-yloxy)-4H-chromen-4-one: A mixture of 5-hydroxy-2-methyl-7-(quinolin-4-yloxy)-4H-chromen-4-one (61 mg, 0.19 mmol), 3-bromo-1-propanol (53 mg, 0.38 mmol), Cs$_2$CO$_3$ (155 mg, 0.48 mmol) in DMF (2.0 mL) was heated to 65° C. under N$_2$ for 16 hours. The mixture cooled to room temperature, quenched with saturated NH$_4$Cl, and extracted with EA. The combined organic extracts were washed with brine and dried over Na$_2$SO$_4$. The crude product was purified by preparative HPLC to afford 11 mg of 5-(3-hydroxypropoxy)-2-methyl-7-(quinolin-4-yloxy)-4H-chromen-4-one as a white solid. Single peak in analytical HPLC. Supporting data: LC-MS (ESI): m/z 378 [M+1]$^+$; $^1$H NMR (400 MHz, CD$_3$OD) δ (ppm) 2.08-2.14 (m, 2H), 2.41 (s, 3H), 3.86 (t, J=5.4 Hz, 2H), 4.26 (t, J=6.2 Hz, 2H), 6.20 (s, 1H), 7.11 (d, J=2.4 Hz, 1H), 7.22 (d, J=2.4 Hz, 1H), 7.31 (dd, J=2.8, 6.8 Hz, 1H), 8.03-8.07 (m, 1H), 8.24-8.26 (m 2H), 8.71 (dd, J=0.8, 6.8 Hz, 1H), 9.02 (d, J=6.4 Hz, 1H).

Example 2

5-(3-hydroxypropoxy)-2-methyl-7-(naphthalen-1-ylmethoxy)-4H-chromen-4-one

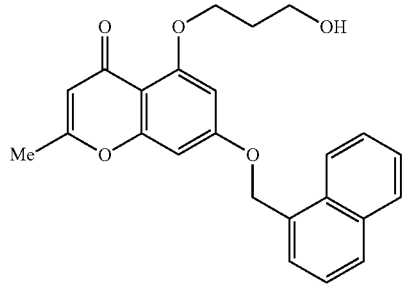 [SMILES: Cc1cc(=O)c2c(OCCCO)cc(OCc3cccc4ccccc34)cc2o1]

Prepared following the procedure of Example 1, using 1-bromomethyl naphthalene as the first alkylating agent (Step 2). Product of step 2, 5-hydroxy-2-phenyl-7-(quinolin-4-yloxy)-4H-chromen-4-one: yellow solid. R$_f$=0.55 (EA: hexanes=1:1); LC-MS (ESI): m/z 382 [M+1]$^+$; $^1$H NMR (400 MHz, CDCl$_3$) δ (ppm) 6.64 (d, J=2.0 Hz, 1H), 6.73 (d, J=2.0 Hz, 1H), 6.97 (d, J=5.2 Hz, 1H), 7.61 (t, J=8.0 Hz, 1H), 7.80 (t, J=8.0 Hz, 1H), 8.15 (d, J=4.4 Hz, 1H), 8.20 (d, J=4.4 Hz, 1H), 8.83 (d, J=4.8 Hz, 1H), 12.83 (s, 1H). Supporting data for the final product: white solid. LC-MS (ESI): m/z 391 [M+1]$^+$; $^1$H NMR (400 MHz, CDCl$_3$) δ (ppm) 2.05-2.13 (m, 2H), 2.21 (s, 3H), 3.84 (t, J=5.4 Hz, 2H), 4.07 (t, J=5.2 Hz, 2H), 5.47 (s, 2H), 5.95 (s, 1H), 6.33 (d, J=2.4 Hz, 1H), 6.56 (d, J=2.4 Hz, 1H), 7.39-7.52 (m, 4H), 7.81-7.94 (m, 3H).

Example 3

5-(4-hydroxybutoxy)-2-methyl-7-(naphthalen-1-ylmethoxy)-4H-chromen-4-one

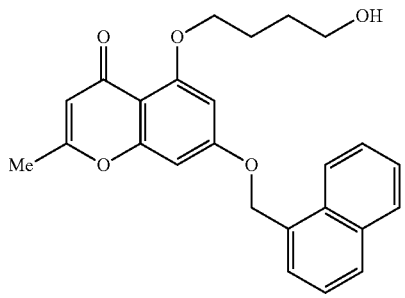 [SMILES: Cc1cc(=O)c2c(OCCCCO)cc(OCc3cccc4ccccc34)cc2o1]

Prepared following the procedure of Example 2, using 4-bromo-1-butanol as the second alkylating agent (Step 3). Supporting data for the final product: white solid. LC-MS (ESI): m/z 405 [M+1]$^+$; $^1$H NMR (400 MHz, CDCl$_3$) δ (ppm) 1.64-1.79 (m, 2H), 1.95-2.05 (m, 2H), 2.20 (s, 3H), 3.68 (t, J=5.4 Hz, 2H), 3.97 (t, J=5.2 Hz, 2H), 5.46 (s, 2H), 5.90 (s, 1H), 6.35 (d, J=2.4 Hz, 1H), 6.55 (d, J=2.4 Hz, 1H), 7.18-7.53 (m, 4H), 7.81-7.94 (m, 3H).

Example 4

5-(2,3-dihydroxypropoxy)-2-methyl-7-(quinolin-4-yloxy)-4H-chromen-4-one

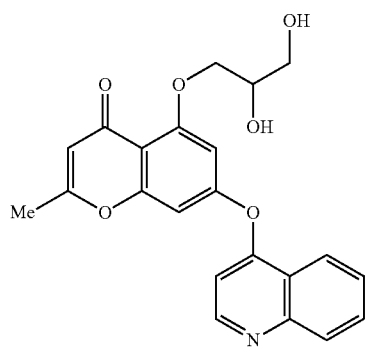 [SMILES: Cc1cc(=O)c2c(OCC(O)CO)cc(Oc3ccnc4ccccc34)cc2o1]

The following synthetic intermediate, 5-(allyloxy)-2-methyl-7-(quinolin-4-yloxy)-4H-chromen-4-one, was prepared following the procedure of Example 1, using allyl bromide as the second alkylating agent (Step 3):

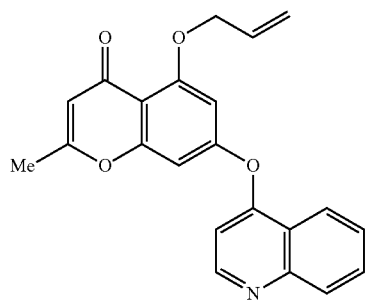 [SMILES: C=CCOc1cc(Oc2ccnc3ccccc23)cc2oc(C)cc(=O)c12]

Supporting data for this compound: white solid. LC-MS (ESI): m/z 360 [M+1]$^+$.

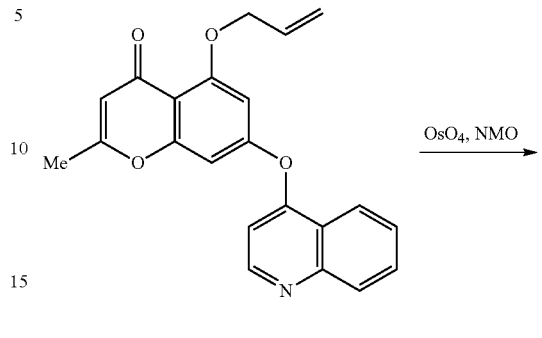

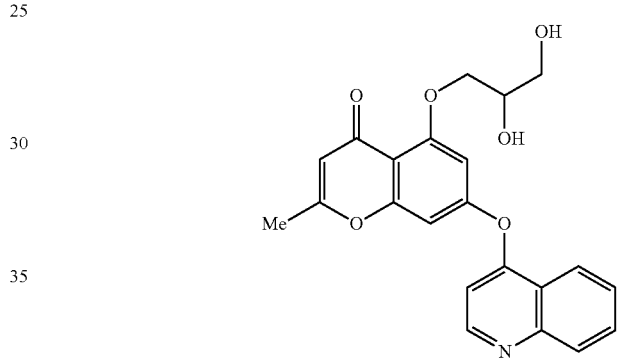

5-(2,3-dihydroxypropoxy)-2-methyl-7-(quinolin-4-yloxy)-4H-chromen-4-one: A mixture of 5-(allyloxy)-2-methyl-7-(quinolin-4-yloxy)-4H-chromen-4-one (40 mg, 0.11 mmol) in acetone (2 mL) and H$_2$O (1 drop) was treated NMO (39 mg, 0.33 mmol) and OsO$_4$ (5.5 μL, 2% solution in H$_2$O) under N$_2$. The resultant mixture was stirred at room temperature for 24 h. The reaction was cooled to 0° C. and treated with saturated Na$_2$SO$_3$. After stirring for 15 min, the reaction was extracted with EA. The combined organic extracts were washed with brine and dried over Na$_2$SO$_4$. The crude product was purified with preparative HPLC to afford 5-(2,3-dihydroxypropoxy)-2-methyl-7-(quinolin-4-yloxy)-4H-chromen-4-one as a white solid.

Supporting data: LC-MS (ESI): m/z 394 [M+1]$^+$; $^1$H NMR (400 MHz, CD$_3$OD) δ (ppm) 2.42 (s, 3H), 3.77 (d, J=5.2 Hz, 2H), 4.03-4.10 (m, 1H), 4.28-4.37 (m, 2H), 6.23 (s, 1H), 7.14 (d, J=2.4 Hz, 1H), 7.23 (d, J=2.4 Hz, 1H), 7.30 (d, J=6.4 Hz, 1H), 78.03-8.23 (m, 3H), 8.69 (d, J=8.4 Hz, 1H), 9.00 (d, J=6.4 Hz, 1H).

Example 5

5-(4-hydroxybutoxy)-2-isopropyl-7-(naphthalen-1-ylmethoxy)-4H-chromen-4-one

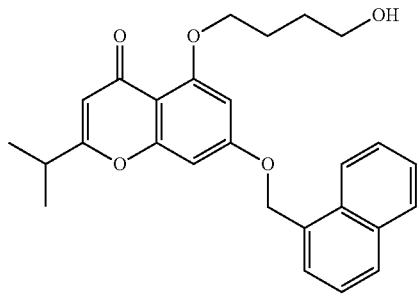 [SMILES: CC(C)c1cc(=O)c2c(OCCCCO)cc(OCc3cccc4ccccc34)cc2o1]

Prepared following the procedure of Example 1, but in step 1 making the 2-isopropyl analog as follows:

Step 1.

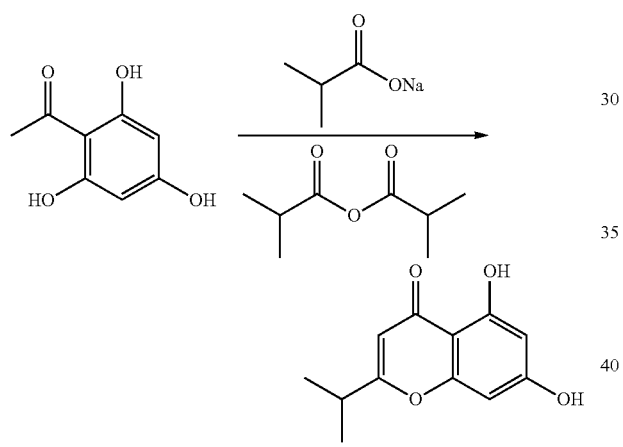

5,7-dihydroxy-2-isopropyl-4H-chromen-4-one: A mixture of 1-(2,4,6-trihydroxyphenyl)ethan-1-one (336 mg, 2.0 mmol), i-PrCO$_2$Na (220 mg, 2.0 mmol) in (i-PrCO)$_2$O (2.0 mL) was heated at 180° C. for 40 min in a microwave reactor. The reaction mixture was poured into water, extracted with EA, washed with saturated NaHCO$_3$ and brine, dried over Na$_2$SO$_4$, concentrated. The residue was treated with a solution of K$_2$CO$_3$ (4.98 g, 36 mmol) in H$_2$O (40 mL) and refluxed for 16 h. Acidified with 3 N HCl. The precipitate was collected by vacuum filtration to afford 179 mg (41%) of 5,7-dihydro-2-isopropyl-4H-chromen-4-one as a light brown solid. R$_f$=0.50 (hexanes:EA=1:1); LC-MS (ESI): m/z 221 [M+1]$^+$; $^1$H NMR (400 MHz, DMSO-d$_6$) δ (ppm) 1.23 (d, J=6.8 Hz, 6H), 2.88 (sep, J=6.8 Hz, 1H), 6.13 (s, 1H), 6.17 (d, J=2.0 Hz, 1H), 6.34 (d, J=2.0 Hz, 1H), 10.82 (s, 1H), 12.81 (s, 1H); $^{13}$C NMR (100 MHz, DMSO-d$_6$) δ (ppm) 19.7, 32.4, 93.7, 98.7, 103.5, 105.2, 157.7, 161.4, 164.1, 174.8, 182.0.

Step 2.

As in Example 2, 1-bromomethyl naphthalene was used the first alkylating agent.

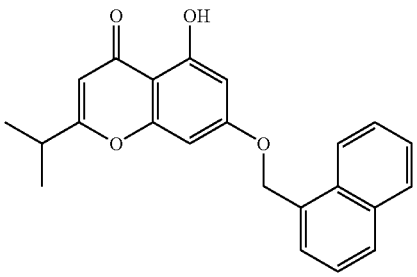 [SMILES: CC(C)c1cc(=O)c2c(O)cc(OCc3cccc4ccccc34)cc2o1]

5-hydroxy-2-isopropyl-7-(naphthalene-1-ylmethoxy)-4H-chromen-4-one: yellow solid. R$_f$=0.30 (EA:hexanes=1:4); LC-MS (ESI): m/z 361 [M+1]$^+$.

Step 3. As in Example 3, using 4-bromo-1-butanol as the second alkylating agent.

Supporting data for 5-(4-hydroxybutoxy)-2-isopropyl-7-(naphthalen-1-ylmethoxy)-4H-chromen-4-one: white solid. LC-MS (ESI): m/z 433 [M+1]$^+$; $^1$H NMR (400 MHz, CDCl$_3$) δ (ppm) 1.20 (d, J=7.2 Hz, 6H), 1.60-1.78 (m, 2H), 1.95-2.05 (m, 2H), 2.70 (sep, J=6.8 Hz, 1H), 3.68 (t, J=5.4 Hz, 2H), 3.97 (t, J=5.0 Hz, 2H), 5.47 (s, 2H), 5.97 (s, 1H), 6.33 (d, J=2.4 Hz, 1H), 6.58 (d, J=2.4 Hz, 1H), 7.40-7.53 (m, 4H), 7.81-7.94 (m, 3H).

Example 6

5-(3-hydroxypropoxy)-2-isopropyl-7-(quinolin-4-ylmethoxy)-4H-chromen-4-one

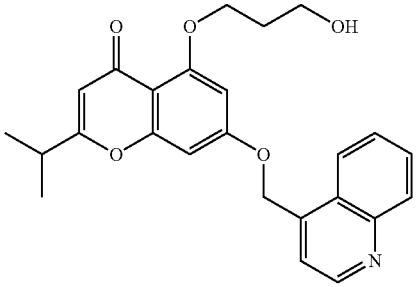 [SMILES: CC(C)c1cc(=O)c2c(OCCCO)cc(OCc3ccnc4ccccc34)cc2o1]

Prepared following the procedure of Example 5, using 4-bromomethyl quinoline as the first alkylating agent (step 2) and using 3-bromo-1-propanol as the second alkylating agent. This intermediate was obtained:

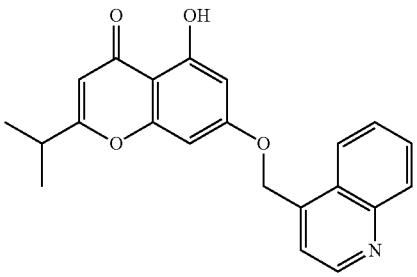 [SMILES: CC(C)c1cc(=O)c2c(O)cc(OCc3ccnc4ccccc34)cc2o1]

Supporting data for 5-hydroxy-2-isopropyl-7-(quinolin-4-ylmethoxy)-4H-chromen-4-one: yellow solid. R$_f$=0.35 (EA:hexanes=1:1); LC-MS (ESI): m/z 362 [M+1]$^+$; $^1$H NMR (400 MHz, CDCl₃) δ (ppm) 1.26 (d, J=7.2 Hz, 6H), 2.78 (sep, J=6.8 Hz, 1H), 5.56 (s, 2H), 6.03 (s, 1H), 6.44 (d, J=2.4 Hz, 1H), 6.49 (d, J=2.4 Hz, 1H), 7.51 (d, J=4.4 Hz, 1H), 7.58-7.62 (m, 1H), 7.73-7.77 (m, 1H), 7.92 (dd, J=0.4, 8.4 Hz, 1H), 8.17, (d, J=8.4 Hz, 1H), 8.91 (d, J=4.4 Hz, 1H), 12.77 (s, 1H).

Supporting data for the final product 5-(3-hydroxypropoxy)-2-isopropyl-7-(quinolin-4-ylmethoxy)-4H-chromen-4-one: white solid. LC-MS (ESI): m/z 420 [M+1]⁺; ¹H NMR (400 MHz, CD₃OD) δ (ppm) 1.21 (d, J=6.8 Hz, 6H), 1.99-2.02 (m, 2H), 2.77 (sep, J=6.8 Hz, 1H), 3.74 (t, J=5.4 Hz, 2H), 4.16 (t, J=6.0 Hz, 2H), 5.88 (s, 2H), 5.95 (s, 1H), 6.69 (d, J=2.4 Hz, 1H), 6.86 (d, J=2.4 Hz, 1H), 7.81-8.33 (m, 5H), 8.99 (d, J=5.2 Hz, 1H).

Example 7

5-(3-hydroxypropoxy)-2-isopropyl-7-(naphthalen-1-ylmethoxy)-4H-chromen-4-one

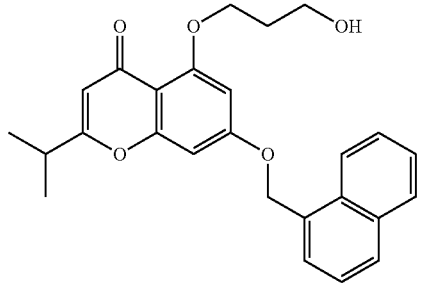 [SMILES: CC(C)c1cc(=O)c2c(OCCCO)cc(OCc3cccc4ccccc34)cc2o1]

Prepared following the procedure of Example 6, using 1-bromomethyl naphthalene as the first alkylating agent (step 2). Supporting data: LC-MS (ESI): m/z 419 [M+1]⁺; ¹H NMR (400 MHz, CDCl₃) δ (ppm) 1.28 (d, J=6.8 Hz, 6H), 2.13 (m, 2H), 2.76-2.81 (m, 1H), 3.95 (br, 2H), 4.15 (t, 2H), 5.56 (s, 2H), 6.07 (s, 1H), 6.41 (d, J=2.4 Hz, 1H), 6.68 (d, J=2.4, 1H), 7.48-7.61 (m, 4H), 7.90-7.94 (m, 2H), 8.01 (dd, J=8.2, 1.6 Hz, 1H), HPLC purity >95%.

Example 8

5-((2-(hydroxymethyl)benzyl)oxy)-2-isopropyl-7-(naphthalen-1-ylmethoxy)-4H-chromen-4-one

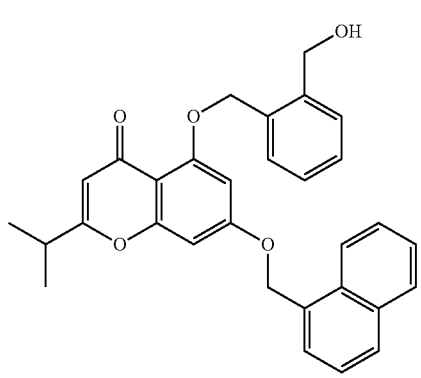

Prepared following the procedure of Example 7 except with the following modification of step 3:

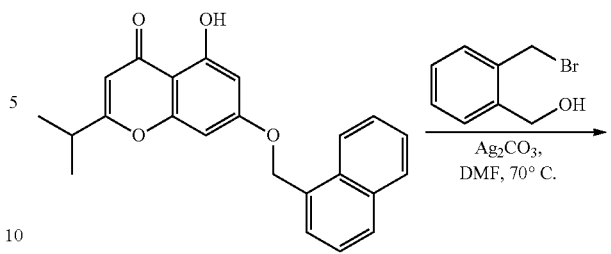

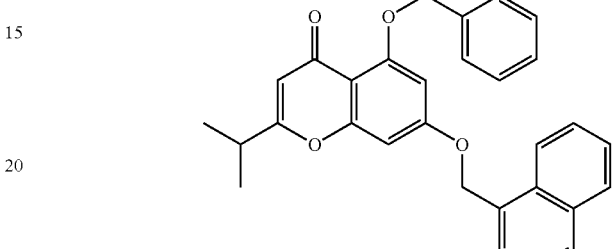

A solution of the starting material 5-hydroxy-2-isopropyl-7-(naphthalen-1-ylmethoxy)-4H-chromen-4-one (see Example 7) (1.0 eq.) in DMF was treated with Ag₂CO₃ (2.0 eq.) and 2-(bromomethyl)benzyl alcohol (2.0 eq.) at room temperature under argon in a sealed tube. Then the suspension was heated at 70° C. 12 h. After that time, the reaction was cooled to room temperature and filtered. The residue was purified by preparative HPLC to give the target compound as a colorless solid. Supporting data: LC-MS (ESI): m/z 481 [M+1]⁺; ¹H NMR (400 MHz, CDCl₃) δ 1.27 (d, J=6.8 Hz, 6H), 2.74-2.81 (m, 1H), 4.64 (s, 2H), 5.15 (s, 2H), 5.58 (s, 2H), 6.01 (s, 1H), 6.61 (d, J=2.4 Hz, 1H), 6.70 (d, J=2.4 Hz, 1H), 7.29-7.42 (md, 4H), 7.49-7.63 (m, 5H), 7.93 (dd, J=8.0, 9.2 Hz, 2H), 8.02 (d, J=8.0 Hz, 1H), HPLC purity >95%.

Example 9

5-((2-(hydroxymethyl)benzyl)oxy)-2-isopropyl-7-(quinolin-4-yloxy)-4H-chromen-4-one

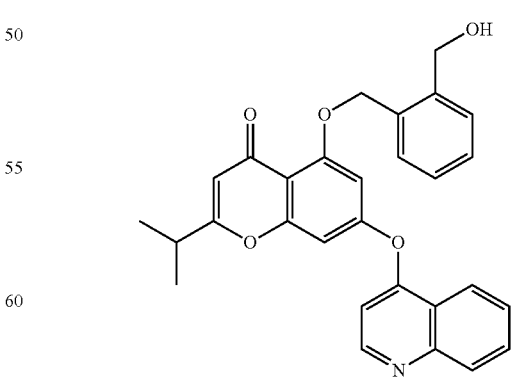

Prepared following the procedure of Example 8 but using 4-chloroquinoline in the first alkylation step as in Example 1. Supporting data: LC-MS (ESI): m/z 468 [M+1]⁺; ¹H NMR (400 MHz, DMSO-d₆) δ 1.23 (d, J=6.8 Hz, 6H), 2.81-2.90 (m, 1H), 4.59 (s, 2H), 5.26 (s, 2H), 6.07 (s, 1H), 7.11 (d, J=2.0 Hz, 1H), 7.16 (d, J=5.6 Hz, 1H), 7.22 (d, J=2.0 Hz, 1H), 7.29-7.37 (md, J=1.6 Hz, 2H), 7.45 (d, J=1.6, 8.8 Hz, 1H), 7.74 (d, 1H), 7.83 (t, J=7.6 Hz, 1H), 8.00 (t, J=7.2 Hz, 1H), 8.18 (d, J=8.8 Hz, 1H), 8.39 (d, J=7.6 Hz, 1H), 8.97 (d, J=5.6 Hz, 1H), HPLC purity=87%.

Example 10

5-((2-(hydroxymethyl)benzyl)oxy)-2-isopropyl-7-((2-(trifluoromethyl)pyridin-3-yl)methoxy)-4H-chromen-4-one

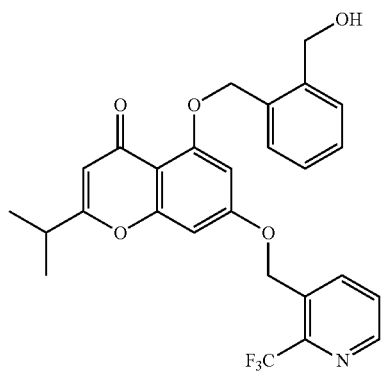 [SMILES: CC(C)c1cc(=O)c2c(OCc3ccccc3CO)cc(OCc3cccnc3C(F)(F)F)cc2o1]

Prepared following the procedure of Example 8 but using 3-(bromomethyl)-2-(trifluoromethyl)pyridine in the first alkylation step. Supporting data: LC-MS (ESI): m/z 500 [M+1]⁺; ¹H NMR (400 MHz, CDCl₃) δ 1.27 (d, J=6.8 Hz, 6H), 2.71-2.81 (m, 1H), 4.64 (s, 2H), 5.20 (s, 2H), 5.18 (s, 2H), 6.00 (s, 1H), 6.42 (d, J=2.4 Hz, 1H), 6.61 (d, J=2.4 Hz, 1H), 7.28-7.32 (td, J=7.6 Hz, J=1.2 Hz, 1H), 7.37-7.43 (qt, J=7.2 Hz, J=1.2 Hz, 2H), 7.51 (dd, J=7.2 Hz, J=1.2 Hz, 1H), 7.58-7.61 (m, 1H), 8.13 (d, J=8.0 Hz, 1H), 8.71 (d, J=3.6 Hz, 1H), HPLC purity >95%.

Example 11

5-((2-(hydroxymethyl)benzyl)oxy)-2-isopropyl-7-((3-(trifluoromethyl)pyridin-2-yl)oxy)-4H-chromen-4-one

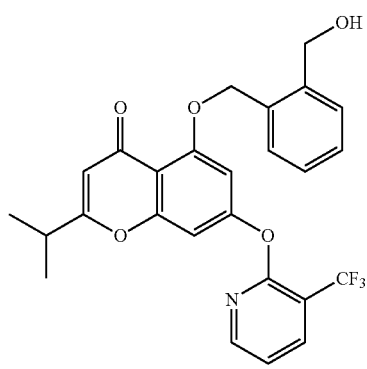 [SMILES: CC(C)c1cc(=O)c2c(OC(C)c3ccccc3CO)cc(Oc3ncccc3C(F)(F)F)cc2o1]

Prepared following the procedure of Example 8 but using 2-chloro-3-(trifluoromethyl)pyridine in the first alkylation step. Supporting data: LC-MS (ESI): m/z 486 [M+1]⁺; ¹H NMR (400 MHz, CDCl₃) δ 1.26 (d, J=7.2 Hz, 6H), 2.73-2.80 (m, 1H), 4.65 (s, 2H), 5.17 (s, 2H), 5.20 (s, 2H), 6.04 (s, 1H), 6.81 (d, J=2.0 Hz, 1H), 6.87 (d, J=2.0 Hz, 1H), 7.22-7.27 (md, 1H), 7.28 (dd, J=7.2 Hz, J=1.2 Hz, 1H), 7.35 (dd, J=7.2 Hz, J=1.2 Hz, 1H), 7.40 (td, J=7.2 Hz, J=1.2 Hz, 1H), 7.53 (dd, J=7.6 Hz, J=1.2 Hz, 1H), 8.08 ((dd, J=7.6 Hz, J=2.0 Hz, 1H), 8.39 ((dd, J=5.2 Hz, J=1.2 Hz, 1H), HPLC purity >95%.

Example 12

5-((2-(hydroxymethyl)benzyl)oxy)-2-isopropyl-7-((3-(trifluoromethyl)benzyl)oxy)-4H-chromen-4-one

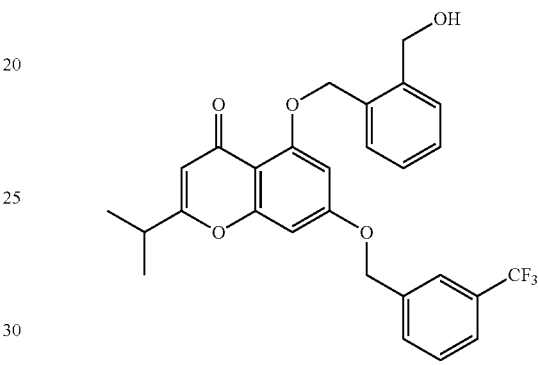

Prepared following the procedure of Example 8 but using 1-(chloromethyl)-3-(trifluoromethyl)benzene pyridine in the first alkylation step. Supporting data: LC-MS (ESI): m/z 499 [M+1]⁺; ¹H NMR (400 MHz, CDCl₃) δ 1.27 (d, J=6.8 Hz, 6H), 2.73-2.80 (m, 1H), 4.64 (s, 2H), 5.20 (s, 4H), 6.01 (s, 1H), 6.55 (d, J=2.4 Hz, 1H), 6.60 (d, J=2.4 Hz, 1H), 7.28-7.32 (td, J=7.2 Hz, J=1.2 Hz, 1H), 7.37-7.43 (mt, 2H), 7.53 (td, J=7.2 Hz, J=1.2 Hz, 1H), 7.57 (d, J=8.0 Hz, 1H), 7.65 (d, J=8.0 Hz, 2H), 7.75 (s, 1H), HPLC purity >95%.

Example 13

5-((2-(hydroxymethyl)benzyl)oxy)-2-isopropyl-7-(pyridin-2-ylmethoxy)-4H-chromen-4-one

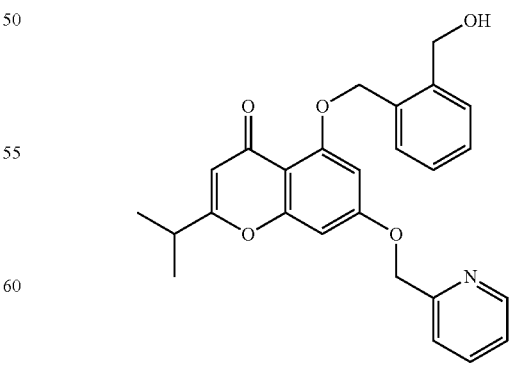

Prepared following the procedure of Example 8 but using 2-(chloromethyl)pyridine in the first alkylation step. Supporting data: LC-MS (ESI): m/z 432 [M+1]⁺; ¹H NMR (400

MHz, CDCl₃) δ 1.27 (d, J=7.2 Hz, 6H), 2.72-2.83 (m, 1H), 4.68 (s, 2H), 5.24 (s, 2H), 5.45 (s, 2H), 6.04 (s, 1H), 6.60 (s, 1H), 6.71 (s, 1H), 7.28-7.32 (td, J=7.6 Hz, J=1.2 Hz, 1H), 7.36-7.40 (td, J=7.6 Hz, J=1.2 Hz, 2H), 7.53 (dd, J=7.6 Hz, J=1.2 Hz, 1H), 7.59 (br, 1H), 7.80 (br, 1H), 8.09 (t, J=7.6 Hz, 1H), 8.81 (br, 1H), HPLC purity >95%.

Example 14

5-((2-(hydroxymethyl)benzyl)oxy)-2-isopropyl-7-(pyridin-3-ylmethoxy)-4H-chromen-4-one

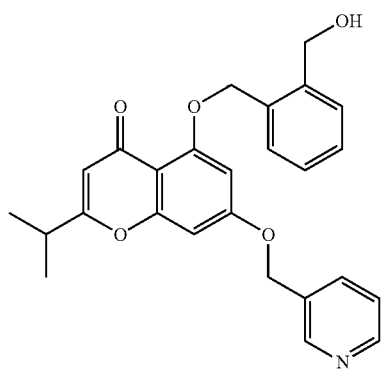

Prepared following the procedure of Example 8 but using 3-(chloromethyl)pyridine in the first alkylation step. Supporting data: LC-MS (ESI): m/z 432 [M+1]⁺; ¹H NMR (400 MHz, CDCl₃) δ 1.27 (d, J=6.8 Hz, 6H), 2.73-2.80 (m, 1H), 4.63 (s, 2H), 5.17 (s, 2H), 5.18 (s, 2H), 5.99 (s, 1H), 6.56 (d, J=2.4 Hz, 1H), 6.59 (d, J=2.4 Hz, 1H), 7.27-7.33 (md, 1H), 7.39 (m, 3H), 7.51 (dd, J=7.6 Hz, J=1.2 Hz, 1H), 7.82 (d, J=8.0 Hz, 1H), 8.65 (s, 1H), 8.74 (s, 1H), HPLC purity >95%.

Example 15

5-((2-(hydroxymethyl)benzyl)oxy)-2-isopropyl-7-(pyridin-4-ylmethoxy)-4H-chromen-4-one

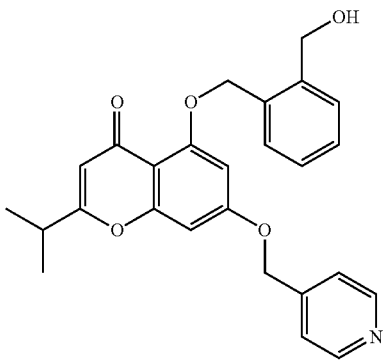 [SMILES: CC(C)c1cc(=O)c2c(OC(C)c3ccccc3CO)cc(OCc3ccncc3)cc2o1]

Prepared following the procedure of Example 8 but using 4-(chloromethyl)pyridine in the first alkylation step. Supporting data: LC-MS (ESI): m/z 432 [M+1]⁺; ¹

Example 16

5-((2-(hydroxymethyl)benzyl)oxy)-2-isopropyl-7-((5-(trifluoromethyl)pyridin-3-yl)methoxy)-4H-chromen-4-one

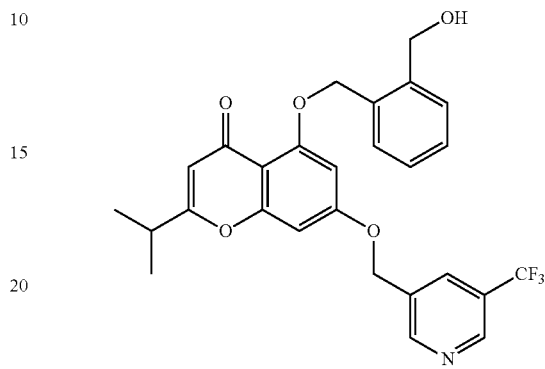

Prepared following the procedure of Example 8 but using 3-(bromomethyl)-5-(trifluoromethyl)pyridine in the first alkylation step. Supporting data: LC-MS (ESI): m/z 500 [M+1]⁺; ¹

Example 17

5-((2-(hydroxymethyl)benzyl)oxy)-2-isopropyl-7-((3-(trifluoromethyl)pyridin-4-yl)oxy)-4H-chromen-4-one

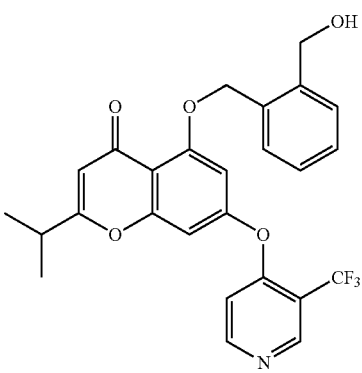 [SMILES: CC(C)c1cc(=O)c2c(OC(C)c3ccccc3CO)cc(Oc3ccncc3C(F)(F)F)cc2o1]

Prepared following the procedure of Example 8 but using 4-chloro-3-(trifluoromethyl)pyridine in the first alkylation step. Supporting data: LC-MS (ESI): m/z 486 [M+1]⁺; ¹H NMR (400 MHz, CDCl₃) δ 1.25 (d, J=7.2 Hz, 6H), 2.72-2.82 (m, 1H), 4.65 (s, 2H), 5.22 (s, 2H), 6.05 (s, 1H), 6.73 (q, J=2.4 Hz, 2H), 7.27-7.33 (td, J=7.6 Hz, J=1.2 Hz, 1H), 7.35-7.42 (m, 3H), 7.50 (dd, J=7.6 Hz, J=1.2 Hz, 1H), 8.70 (br, 1H), 8.92 (br, 1H), HPLC purity >95%.

Example 18

5-((2-(hydroxymethyl)benzyl)oxy)-2-isopropyl-7-(thiazol-5-ylmethoxy)-4H-chromen-4-one

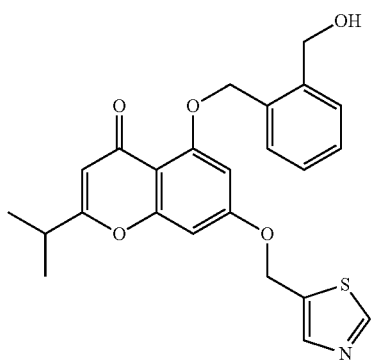

Prepared following the procedure of Example 8 but using 5-(bromomethyl)thiazole in the first alkylation step. Supporting data: LC-MS (ESI): m/z 438 [M+1]+; 1H NMR (400 MHz, CD3OD) δ 1.32 (d, J=6.8 Hz, 6H), 2.82-2.93 (m, 1H), 4.70 (s, 2H), 5.33 (s, 2H), 5.51 (s, 2H), 6.04 (s, 1H), 6.74 (d, J=2.0 Hz, 1H), 6.82 (d, J=2.2 Hz, 1H), 7.30-7.39 (md, 2H), 7.45 (dd, J=7.2 Hz, J=1.2 Hz, 1H), 7.35 (dd, J=6.8 Hz, J=1.6 Hz, 1H), 8.08 (br, 1H), 9.19 (br, 1H).

Example 19

5-((2-(hydroxymethyl)benzyl)oxy)-2-isopropyl-7-(quinolin-8-ylmethoxy)-4H-chromen-4-one

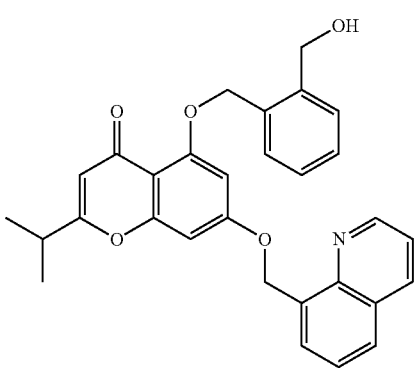 [SMILES: CC(C)c1cc(=O)c2c(OCc3ccccc3CO)cc(OCc3cccc4cccnc34)cc2o1]

Prepared following the procedure of Example 8 but using 8-bromomethyl quinoline in the first alkylation step. Supporting data: LC-MS (ESI): m/z 482 [M+1]+; 1H NMR (400 MHz, CDCl3) δ 1.25 (d, J=6.8 Hz, 6H), 2.7-2.78 (m, 1H), 4.64 (s, 2H), 5.18 (s, 2H), 5.92 (s, 2H), 5.98 (s, 1H), 6.72 (d, J=2.4 Hz, 1H), 6.76 (d, J=2.4 Hz, 1H), 7.29 (dd, J=7.6 Hz, J=2.4 Hz, 1H), 7.34-7.41 (md, 2H), 7.50-7.53 (m, 2H), 7.63 (t, J=7.2 Hz, 1H), 7.86 (d, J=8.4 Hz, 1H), 7.96 (dd, J=7.2 Hz, J=1.2 Hz, 1H), 8.26 (dd, J=8.4 Hz, J=1.6 Hz, 1H) 9.23 (dd, J=4.4 Hz, J=2.0 Hz, 1H), HPLC purity >95%.

Example 20

5-((2-(hydroxymethyl)benzyl)oxy)-2-isopropyl-7-(quinolin-2-ylmethoxy)-4H-chromen-4-one

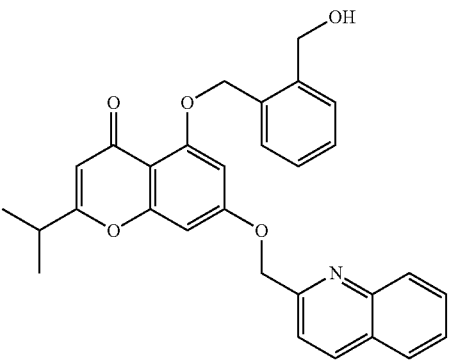 [SMILES: CC(C)c1cc(=O)c2c(OCc3ccccc3CO)cc(OCc3ccc4ccccc4n3)cc2o1]

Prepared following the procedure of Example 8 but using 2-bromomethyl quinoline in the first alkylation step. Supporting data: LC-MS (ESI): m/z 482 [M+1]+; 1H NMR (400 MHz, CDCl3) δ 1.26 (d, J=6.8 Hz, 6H), 2.7-2.80 (m, 1H), 4.67 (s, 2H), 5.26 (s, 2H), 5.72 (s, 2H), 6.03 (s, 1H), 6.66 (d, J=2.4 Hz, 1H), 6.74 (d, J=2.4 Hz, 1H), 7.23-7.27 (m, 1H), 7.3-7.35 (td, J=7.2 Hz, J=1.2 Hz, 1H), 7.38-7.43 (qd, J=7.6 Hz, J=1.2 Hz 2H), 7.76 (t, J=7.2 Hz, 1H), 7.83 (d, J=8.4 Hz, 1H), 7.96 (td, J=6.8 Hz, J=1.2 Hz, 1H), 8.99 (dd, J=8.4 Hz, J=0.8 Hz, 1H), 8.38 (d, J=8.8 Hz, 1 H), 8.50 (d, J=8.8 Hz, 1H), HPLC purity >95%.

Example 21

5-((2-(hydroxymethyl)benzyl)oxy)-2-isopropyl-7-(quinolin-6-ylmethoxy)-4H-chromen-4-one

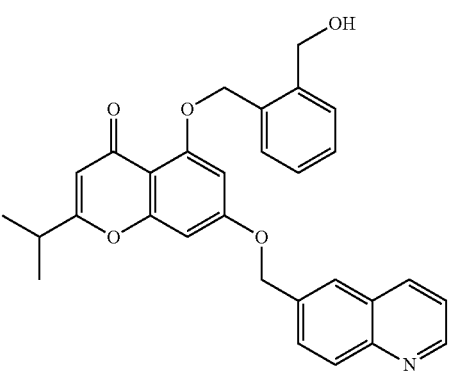 [SMILES: CC(C)c1cc(=O)c2c(OCc3ccccc3CO)cc(OCc3ccc4ncccc4c3)cc2o1]

Prepared following the procedure of Example 8 but using 6-bromomethyl quinoline in the first alkylation step. Supporting data: LC-MS (ESI): m/z 482 [M+1]+; 1H NMR (400 MHz, CDCl3) δ 1.25 (d, J=6.8 Hz, 6H), 2.70-2.80 (m, 1H), 4.64 (s, 2H), 5.20 (s, 2H), 5.34 (s, 2H), 5.98 (s, 1H), 6.59 (d, J=2.4 Hz, 1H), 6.64 (d, J=2.4 Hz, 1H), 7.28 (dd, J=7.6 Hz, J=1.6 Hz, 1H) 7.36-7.41 (m, 2H), 7.47-7.52 (m, 2H), 7.81 (dd, J=8.8 Hz, J=2.0 Hz, 1H), 7.93 (s, 1 H), 8.24 (dd, J=7.2 Hz, J=3.2 Hz, 2H), 8.96 (d, J=3.2 Hz, 1H), HPLC purity >95%.

Example 22

2-cyclopropyl-5-((2-(hydroxymethyl)benzyl)oxy)-7-(naphthalen-1-ylmethoxy)-4H-chromen-4-one

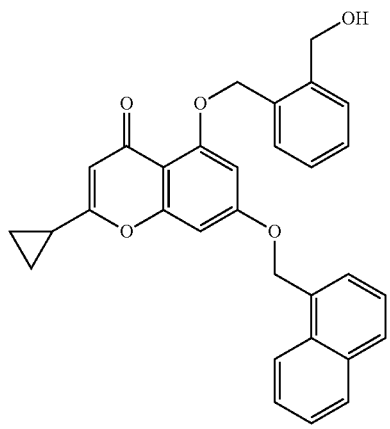 [SMILES: O=c1cc(C2CC2)oc2cc(OCc3cccc4ccccc34)cc(OCc3ccccc3CO)c12]

Prepared following the procedure of Example 8 but using reagents with R²=cyclopropyl in the Synthetic Scheme 1 reaction sequence.

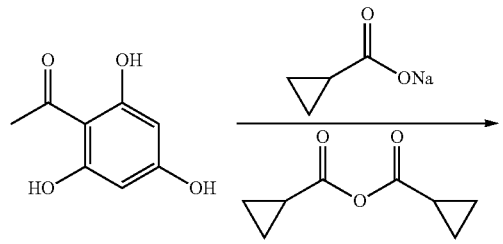

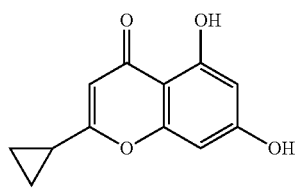

Supporting data: LC-MS (ESI): m/z 479 [M+1]⁺.

Example 23

2-cyclopropyl-5-((2-(hydroxymethyl)benzyl)oxy)-7-((2-(trifluoromethyl)pyridin-3-yl)methoxy)-4H-chromen-4-one

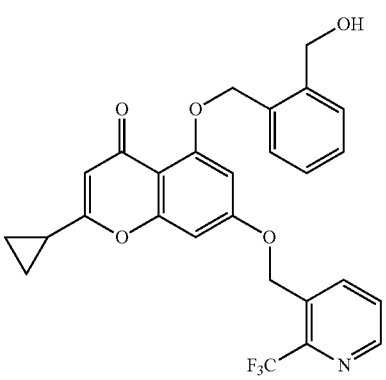 [SMILES: O=c1cc(C2CC2)oc2cc(OCc3cccnc3C(F)(F)F)cc(OCc3ccccc3CO)c12]

Prepared following the procedure of Example 10 but using reagents with R²=cyclopropyl in the Synthetic Scheme 1 reaction sequence, as in example 22. Supporting data: LC-MS (ESI): m/z 498 [M+1]⁺; ¹H NMR (400 MHz, CDCl₃) δ (ppm) 1.01-1.07 (m, 4H), 1.74-1.79 (m, 1H), 4.62 (s, 2H), 5.17 (s, 2H), 5.34 (s, 2H), 5.99 (s, 1H), 6.42 (d, J=2.0 Hz, 1H), 6.58 (d, J=2.0 Hz, 1H), 7.24-7.40 (m, 3H), 7.48-7.59 (m, 2H), 8.10 (d, J=7.2 Hz, 1H), 8.69 (d, J=7.2 Hz, 1H).

Example 24

5-((2-(hydroxymethyl)benzyl)oxy)-2-isopropyl-7-(quinolin-4-ylmethoxy)-4H-chromen-4-one

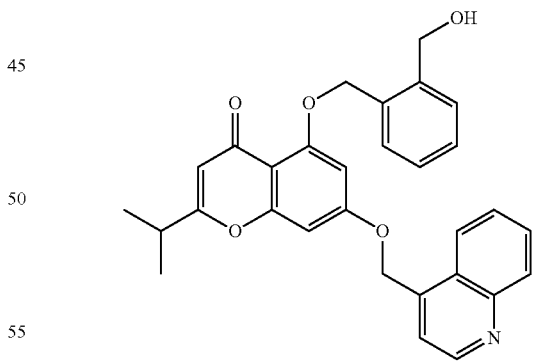

Prepared following the procedure of Example 8 but using 4-bromomethyl quinoline in the first alkylation step. Supporting data: LC-MS (ESI): m/z 482 [M+1]⁺; ¹H NMR (400 MHz, CDCl₃) δ 1.27 (d, J=6.8 Hz, 6H), 2.74-2.81 (m, 1H), 4.67 (s, 2H), 5.24 (s, 2H), 5.78 (s, 2H), 6.04 (s, 1H), 6.62 (d, J=2.4 Hz, 1H), 6.71 (d, J=2.4 Hz, 1H), 7.29-7.53 (md, 4H), 7.88 (t, J=7.2 Hz, 1H), 8.01 (m, 2H), 8.15 (d, J=8.0 Hz, 1H), 8.55 (d, J=8.4 Hz, 1H), 9.23 (d, J=5.2 Hz, 1H), HPLC purity >95%.

Example 25

7-((1-chloroisoquinolin-4-yl)methoxy)-5-((2-(hydroxymethyl)benzyl)oxy)-2-isopropyl-4H-chromen-4-one

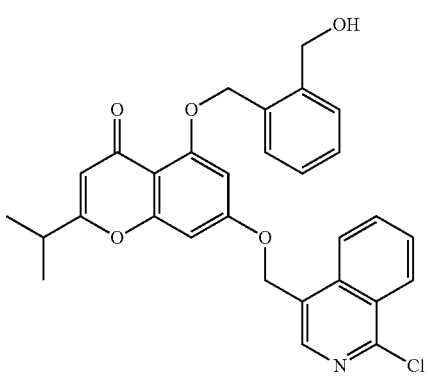 [SMILES: CC(C)c1cc(=O)c2c(OCc3ccccc3CO)cc(OCc3cnc(Cl)c4ccccc34)cc2o1]

Prepared following the procedure of Example 8 but using 3-bromomethyl-2-chloro isoquinoline in the first alkylation step. Supporting data: LC-MS (ESI): m/z 516 [M+1]+; $^1$H NMR (400 MHz, CDCl$_3$) δ 1.27 (d, J=6.8 Hz, 6H), 2.75-2.89 (m, 1H), 4.63 (s, 2H), 5.16 (s, 2H), 5.50 (s, 2H), 6.01 (s, 1H), 6.57 (d, J=2.4 Hz, 1H), 6.70 (d, J=2.4 Hz, 1H), 7.18-7.32 (md, J=1.2 Hz, 3H), 7.41 (dd, J=7.6, 1.2 Hz, 1H), 7.67-7.71 (qd, J=1.2, 6.8 Hz, 1H), 7.76-7.80 (qd, J=1.2, 6.8 Hz, 1H), 7.97 (d, J=8.4 Hz, 1H), 8.31 (s, 1H), 8.37 (dd, J=0.4, 8.4 Hz, 1H).

Example 26

5-(3-hydroxypropoxy)-2-phenyl-7-(quinolin-4-yloxy)-4H-chromen-4-one

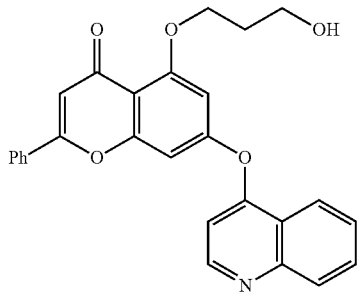 [SMILES: O=c1cc(-c2ccccc2)oc2cc(Oc3ccnc4ccccc34)cc(OCCCO)c12]

Prepared following the procedure of Example 1, beginning with step 2, using chrysin as the starting material:

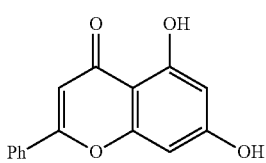

chrysin

The product of step 2 is 5-hydroxy-2-phenyl-7-(quinolin-4-yloxy)-4H-chromen-4-one, the structure below:

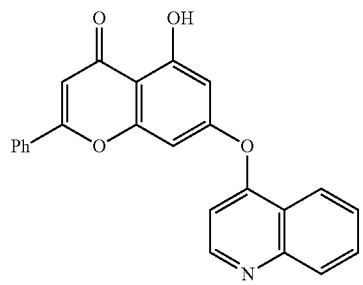 [SMILES: O=c1cc(-c2ccccc2)oc2cc(Oc3ccnc4ccccc34)cc(O)c12]

Supporting data for this intermediate: yellow solid. R$_f$=0.55 (EA:hexanes=1:1); LC-MS (ESI): m/z 382 [M+1]+; $^1$H NMR (400 MHz, CDCl$_3$) δ (ppm) 6.64 (d, J=2.0 Hz, 1H), 6.73 (d, J=2.0 Hz, 1H), 6.97 (d, J=5.2 Hz, 1H), 7.61 (t, J=8.0 Hz, 1H), 7.80 (t, J=8.0 Hz, 1H), 8.15 (d, J=4.4 Hz, 1H), 8.20 (d, J=4.4 Hz, 1H), 8.83 (d, J=4.8 Hz, 1H), 12.83 (s, 1H).

Supporting data for the final product of this Example, 5-(3-hydroxypropoxy)-2-phenyl-7-(quinolin-4-yloxy)-4H-chromen-4-one: LC-MS (ESI): m/z 440 [M+1]+; $^1$H NMR (400 MHz, CD$_3$OD) δ (ppm) 1.99-2.08 (m, 2H), 3.77 (t, J=5.4 Hz, 2H), 4.18 (t, J=6.0 Hz, 2H), 6.77 (s, 1H), 7.02 (d, J=2.0 Hz, 1H), 7.22 (d, J=6.8 Hz, 1H), 7.26 (d, J=2.0 Hz, 1H), 7.45-7.49 (m, 3H), 7.90-7.93 (m, 3H), 8.09-8.11 (m, 2H), 8.57 (d, J=8.4 Hz, 1H), 8.89 (d, J=6.4 Hz, 1H).

Example 27

5-(2,3-dihydroxypropoxy)-2-phenyl-7-(quinolin-4-yloxy)-4H-chromen-4-one

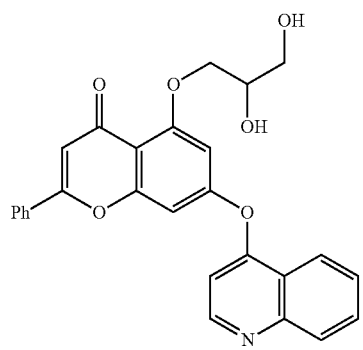 [SMILES: O=c1cc(-c2ccccc2)oc2cc(Oc3ccnc4ccccc34)cc(OCC(O)CO)c12]

Prepared following the procedure of Example 4, beginning with step 2, and using chrysin as the starting material.

The product of step 3 is 5-(allyloxy)-2-phenyl-7-(quinolin-4-yloxy)-4H-chromen-4-one, the structure below:

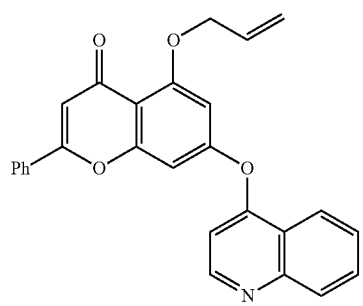 [SMILES: C=CCOc1cc(Oc2ccnc3ccccc23)cc2oc(-c3ccccc3)cc(=O)c12]

Supporting data for this intermediate: LC-MS (ESI): m/z 422 [M+1]+.

Supporting data for the final product of this Example, 5-(2,3-dihydroxypropoxy)-2-phenyl-7-(quinolin-4-yloxy)-4H-chromen-4-one: white solid. LC-MS (ESI): m/z 456 [M+1]+; $^1$H NMR (400 MHz, CD$_3$OD) δ (ppm) 3.67 (d, J=5.6 Hz, 2H), 3.96-3.99 (m, 1H), 4.11-4.13 (m, 2H), 6.80 (s, 1H), 7.05 (d, J=2.4 Hz, 1H), 7.22 (d, J=6.4 Hz, 1H), 7.28 (d, J=2.4 Hz, 1H), 7.45-7.50 (m, 3H), 7.89-7.94 (m, 3H), 8.05-8.11 (m, 2H), 8.56 (d, J=8.4 Hz, 1H), 8.88 (d, J=6.4 Hz, 1H).

Example 28

5-(3-hydroxypropoxy)-7-(naphthalen-1-ylmethoxy)-2-phenyl-4H-chromen-4-one

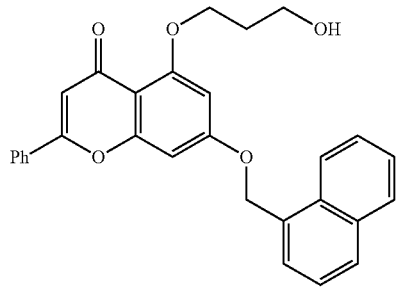 [SMILES: O=c1cc(-c2ccccc2)oc2cc(OCc3cccc4ccccc34)cc(OCCCO)c12]

Prepared following the procedure of Example 2, beginning with step 2, and using chrysin as the starting material.

The product of step 2 is 5-hydroxy-2-methyl-7-(naphthalene-1-ylmethoxy)-4H-chromen-4-one, the compound below:

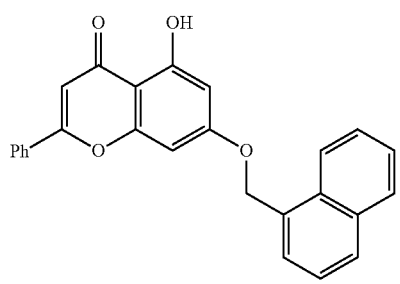 [SMILES: O=c1cc(-c2ccccc2)oc2cc(OCc3cccc4ccccc34)cc(O)c12]

Supporting data for this intermediate: yellow solid. Rf=0.18 (EA:hexanes=1:4); LC-MS (ESI) m/z 395 [M+1]+.

Supporting data for final product of this Example, 5-(3-hydroxypropoxy)-7-(naphthalen-1-ylmethoxy)-2-phenyl-4H-chromen-4-one: white solid. LC-MS (ESI): m/z 453 [M+1]+

Example 29

5-(4-hydroxybutoxy)-7-(naphthalen-1-ylmethoxy)-2-phenyl-4H-chromen-4-one

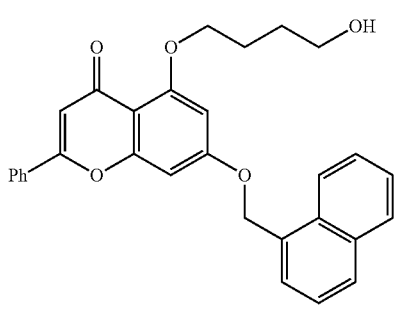 [SMILES: O=c1cc(-c2ccccc2)oc2cc(OCc3cccc4ccccc34)cc(OCCCCO)c12]

Prepared following the procedure of Example 28, but using 4 bromo-1-butanol in the final alkylation step. Supporting data for this product: white solid. LC-MS (ESI): m/z 467 [M+1]+; $^1$H NMR (400 MHz, CDCl$_3$) δ (ppm) 1.78-1.86 (m, 2H), 2.08-2.19 (m, 2H), 3.80 (t, J=5.8 Hz, 2H), 4.11 (t, J=5.0 Hz, 2H), 5.62 (s, 2H), 6.50 (d, J=2.4 Hz, 1H), 6.71 (s, 1H), 6.82 (d, J=2.4 Hz, 1H), 7.51-7.66 (m, 7H), 7.89-8.07 (m, 5H).

Example 30

5-(4-hydroxybutoxy)-2-isopropyl-7-(quinolin-4-ylmethoxy)-4H-chromen-4-one

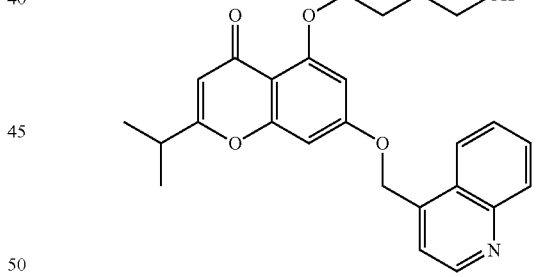

Prepared following the procedure of Example 6, but the final alkylation step was replaced by a two step alkylation/reduction procedure:

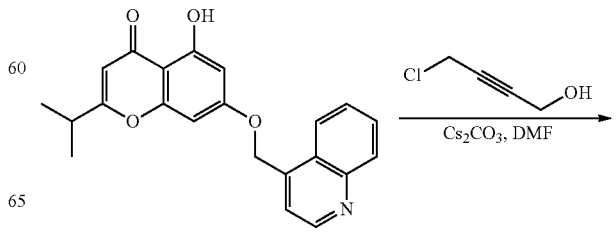

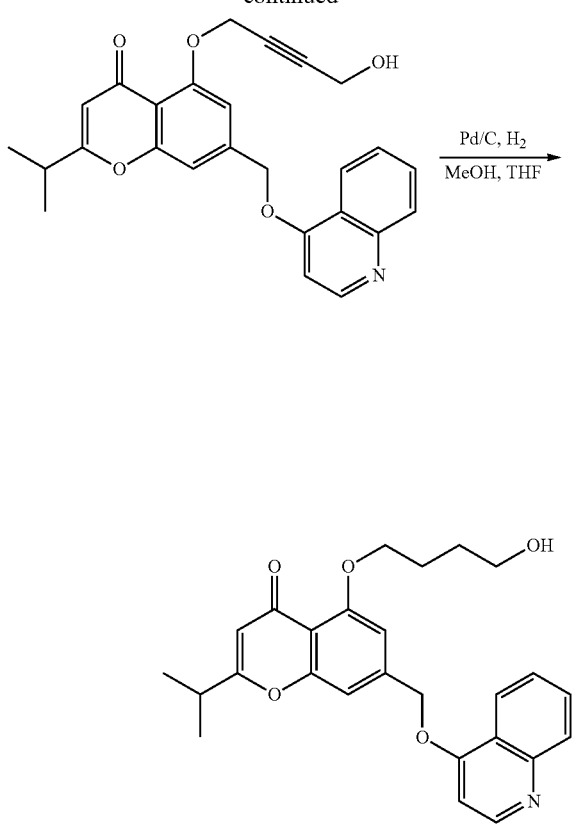

Data for the alkylation product, 5-((4-hydroxybut-2-yn-1-yl)oxy)-2-isopropyl-7-(quinolin-4-ylmethoxy)-4H-chromen-4-one: yellow solid. LC-MS (ESI): m/z 430 [M+1]$^+$; $^1$H NMR (400 MHz, CDCl$_3$) δ (ppm) 1.28 (d, J=6.8 Hz, 6H), 2.78 (sep, J=6.8 Hz, 1H), 4.29 (s, 2H), 4.88 (s, 2H), 5.63 (s, 2H), 6.04 (s, 1H), 6.63-6.67 (m, 2H), 7.57-8.01 (m, 4H), 8.21 (d, J=8.4 Hz, 1H), 8.95 (dd, J=2.4, 4.4 Hz, 1H).

The reduction to give 5-(4-hydroxybutoxy)-2-isopropyl-7-(quinolin-4-ylmethoxy)-4H-chromen-4-one: A solution of 5-((4-hydroxybut-2-yn-1-yl)oxy)-2-isopropyl-7-(quinolin-4-ylmethoxy)-4H-chromen-4-one (27 mg, 0.063 mmol) in THF (5 mL) and MeOH (10 mL) was treated with Pd/C (10 mg, 10%). The resultant mixture was hydrogenated under atmosphere of H2 for 30 min. The reaction was filtered and the crude product was purified by preparative HPLC to afford 5-(4-hydroxybutoxy)-2-isopropyl-7-(quinolin-4-ylmethoxy)-4H-chromen-4-one as a white solid. Supporting data: LC-MS (ESI): m/z 434 [M+1]$^+$; $^1$H NMR (400 MHz, CD$_3$OD) δ (ppm) 1.21 (d, J=6.8 Hz, 6H), 1.65-1.71 (m, 2H), 1.84-1.89 (m, 2H), 2.76 (sep, J=6.8 Hz, 1H), 3.55 (t, J=6.4 Hz, 2H), 4.07 (t, J=6.0 Hz, 2H), 5.87 (s, 2H), 5.94 (s, 1H), 6.56 (d, J=2.4 Hz, 1H), 6.84 (d, J=2.4 Hz, 1H), 7.80-8.32 (m, 5H), 8.99 (d, J=4.4 Hz, 1H).

Example 31

5-((2-(hydroxymethyl)benzyl)oxy)-2-methyl-7-(quinolin-4-yloxy)-4H-chromen-4-one

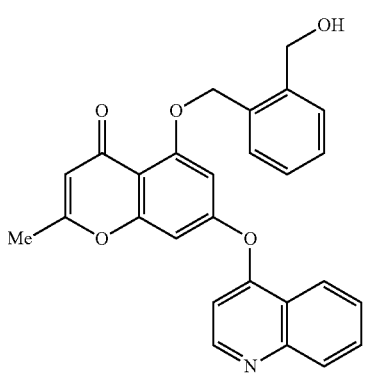 [SMILES: Cc1cc(=O)c2c(OCc3ccccc3CO)cc(Oc3ccnc4ccccc34)cc2o1]

This compound was prepared following the methods of Example 9 but using the methyl-substituted starting material, as in Example 1. Supporting data: LC-MS (ESI): m/z 440 [M+1]$^+$. $^1$H NMR (400 MHz, CD$_3$OD) δ 2.24 (s, 3H), 4.52 (s, 2H), 5.18 (s, 2H), 5.45 (s, 2H), 6.05 (s, 1H), 6.96 (d, J=2.0 Hz, 1H), 7.01 (d, J=5.2 Hz, 1H), 7.13 (d, J=2.0 Hz, 1H), 7.22-7.29 (m, 2H), 7.38 (d, J=6.0 Hz, 1H), 7.70 (t, J=6.8 Hz, 2H), 7.89 (t, J=7.2 Hz, 1H), 8.07 (d, J=8.8 Hz, 1H), 8.27 (d, J=8.0 Hz, 1H), 8.82 (d, J=5.2 Hz, 1H). HPLC purity >95%.

Example 32

5-((2-(hydroxymethyl)benzyl)oxy)-2-isopropyl-7-((4-(trifluoromethyl)pyridin-2-yl)oxy)-4H-chromen-4-one

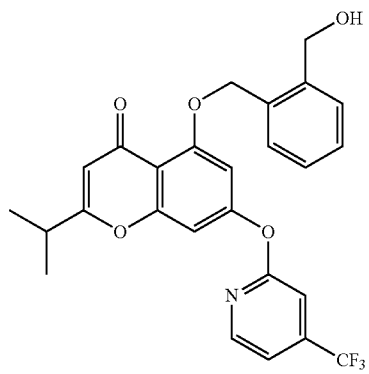 [SMILES: CC(C)c1cc(=O)c2c(OCc3ccccc3CO)cc(Oc3cc(C(F)(F)F)ccn3)cc2o1]

This compound was prepared following the methods of Example 17 but using 2-fluoro-4-(trifluoromethyl)pyridine in the first alkylation procedure. Supporting data: LC-MS (ESI): m/z 486 [M+1]$^+$; m $^1$H NMR (400 MHz, CDCl$_3$) δ 1.27 (d, J=7.2 Hz, 6H), 2.72-2.82 (m, 1H), 4.65 (s, 2H), 5.19 (s, 2H), 6.04 (s, 1H), 6.60 (d, J=2.4 Hz, 1H), 6.84 (d, J=2.4 Hz, 1H), 7.27-7.31 (td, J=6.0 Hz, J=1.2 Hz, 2H), 7.33-7.36 (td, J=7.6 Hz, J=1.2 Hz, 2H), 7.36-7.43 (td, J=7.2 Hz, J=1.2 Hz, 1H), 7.53 (dd, J=7.6 Hz, J=0.8 Hz, 1H), 8.42 (d, J=5.2 Hz, 1H). HPLC purity >95%.

Example 33

5-((2-(hydroxymethyl)benzyl)oxy)-2-isopropyl-7-(pyrimidin-5-ylmethoxy)-4H-chromen-4-one

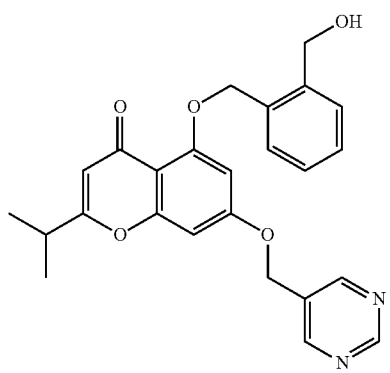 [SMILES: CC(C)c1cc(=O)c2c(OCc3ccccc3CO)cc(OCc3cncnc3)cc2o1]

This compound was prepared following the methods of Example 13 but using 5-(bromomethyl)pyrimidine in the first alkylation procedure. Supporting data: LC-MS (ESI): m/z 433 [M+1]$^+$; $^1$H NMR (400 MHz, CDCl$_3$) δ 1.27 (d, J=6.8 Hz, 6H), 2.74-2.81 (m, 1H), 4.65 (s, 2H), 5.18 (s, 2H), 5.20 (s, 2H), 6.02 (s, 1H), 6.57 (d, J=2.0 Hz, 1H), 6.60 (d, J=2.0 Hz, 1H), 7.29-7.33 (td, J=7.2 Hz, J=1.2 Hz, 1H), 7.37-7.43 (td, J=7.6 Hz, J=1.2 Hz, 2H), 7.53 (dd, J=7.2 Hz, J=1.2 Hz, 1H), 8.89 (br, 2H), 9.28 (br, 1H), HPLC purity >95%.

Synthetic intermediates used to prepare compounds of the invention were prepared by the procedure outlined in Synthetic Scheme 2:

Synthetic Scheme 2

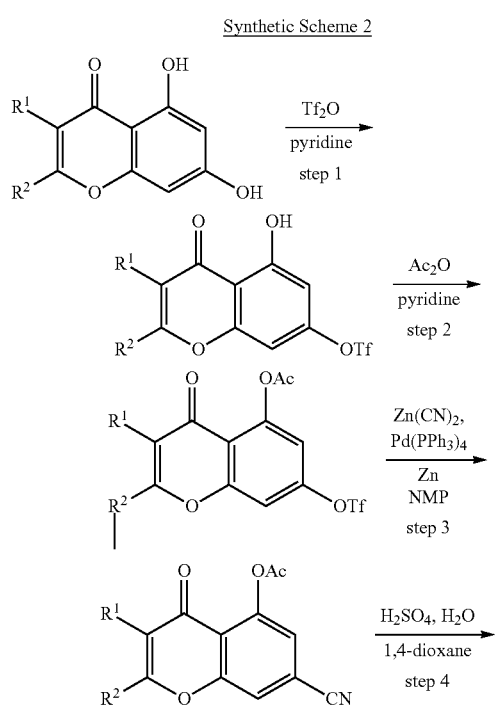

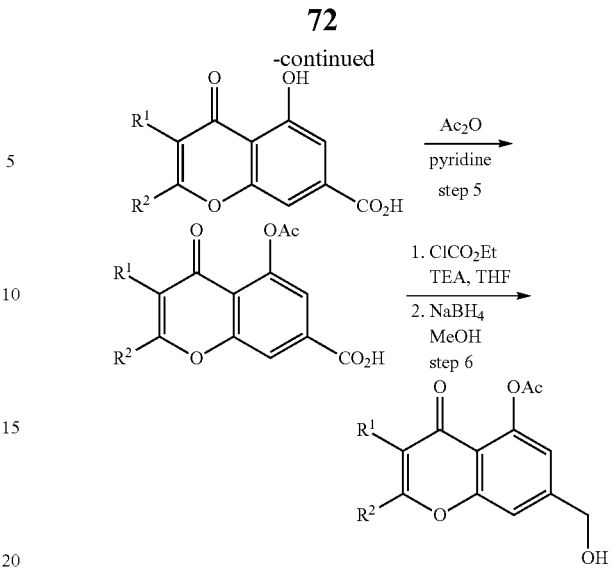

Example 34

7-(hydroxymethyl)-2-isopropyl-4-oxo-4H-chromen-5-yl acetate

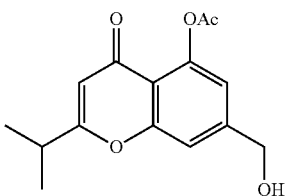 [SMILES: CC(=O)Oc1cc(CO)cc2oc(C(C)C)cc(=O)c12]

The six step sequence of General Scheme 2 was used to make the product of this Example.

Step 1: 5-hydroxy-2-isopropyl-4-oxo-4H-chromen-7-yltrifluoromethanesulfonate:

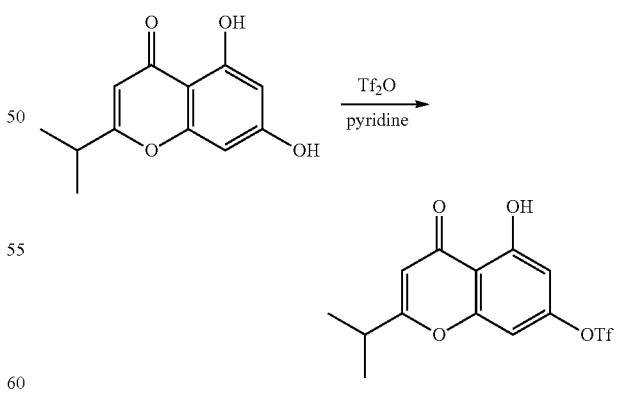

A mixture of 5,7-dihydroxy-2-isopropyl-4H-chromen-4-one (220 mg, 1.00 mmol) and pyridine (395 mg, 5.00 mmol) in DCM (10 mL) was treated with Tf$_2$O (310 mg, 1.10 mmol) at 0° C. under N$_2$. The resultant mixture was stirred at room temperature for 16 h. The reaction was quenched with saturated NH$_4$Cl, extracted with DCM, and dried over Na$_2$SO$_4$. The crude product was purified by column (hexanes:EA=6:1) to afford 270 mg (77%) of 5-hydroxy-2-isopropyl-4-oxo-4H-chromen-7-yltrilfuoromethanesulfoneate as a yellow oil. LC-MS (ESI): m/z 353 [M+1]$^+$; $^1$H NMR (400 MHz, CDCl$_3$) δ (ppm) 1.28 (d, J=6.8 Hz, 6H), 2.91 (sep, J=6.8 Hz, 1H), 6.20 (s, 1H), 6.71 (d, J=2.4 Hz, 1H), 6.87 (d, J=2.4 Hz, 1H), 12.94 (s, 1H). $^{19}$F NMR (400 MHz, CDCl$_3$) δ (ppm) −72.7.

Step 2: 2-isopropyl-4-oxo-7-(((trifluoromethyl)sulfonyl)oxy)-4H-chromen-5-ylacetate

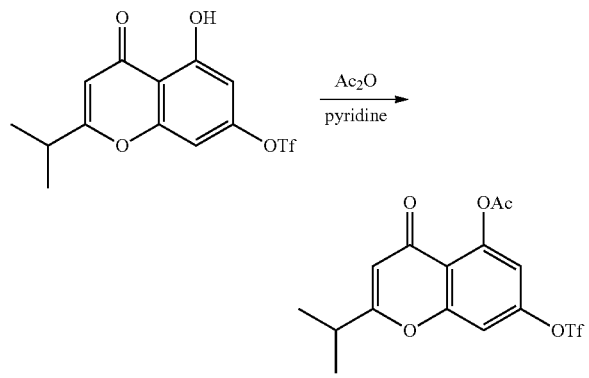

A solution of 5-hydroxy-2-isopropyl-4-oxo-4H-chromen-7-yltrilfuoromethanesulfonate (150 mg, 0.43 mmol) in pyridine (2 mL) was treated with Ac$_2$O (87 mg, 0.85 mmol). The resultant mixture was stirred at room temperature for 16 h and concentrated. The crude product was purified by column (hexanes:EA=4:1) to afford 175 mg (100%) of 2-isopropyl-4-oxo-7-(((trifluoromethyl)sulfonyl)oxy)-4H-chromen-5-ylacetate as a white solid. LC-MS (ESI): m/z 395 [M+1]$^+$; $^1$H NMR (400 MHz, CDCl$_3$) δ (ppm) 1.31 (d, J=6.8 Hz, 6H), 2.45 (s, 3H), 2.85 (sep, J=6.8 Hz, 1H), 6.09 (s, 1H), 6.95 (d, J=2.4 Hz, 1H), 7.33 (d, J=2.4 Hz, 1H).

Step 3: 7-cyano-2-isopropyl-4-oxo-4H-chromen-5-yl acetate

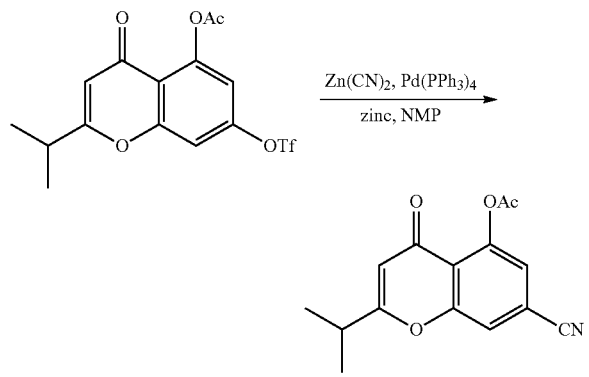

A mixture of 2-isopropyl-4-oxo-7-(((trifluoromethyl)sulfonyl)oxy)-4H-chromen-5-yl acetate (1.86 g, 4.72 mmol), Zn(CN)$_2$ (0.554 g, 4.72 mmol), zinc (62 mg, 0.944 mmol) in NMP was treated with Pd(PPh$_3$)$_4$ (273 mg, 0.236 mmol). The resultant mixture was degassed and heated to 90° C. for 2 h. The reaction was quenched with saturated NH$_4$Cl and extracted with EA. The combined organic extracts were washed with brine and dried over Na$_2$SO$_4$. The crude product was purified by column (hexanes:EA=3:1) to afford 1.248 g (97%) of 7-cyano-2-isopropyl-4-oxo-4H-chromen-5-yl acetate as a yellow solid. LC-MS (ESI): m/z 272 [M+1]$^+$; $^1$H NMR (400 MHz, CDCl$_3$) δ (ppm) 1.32 (d, J=6.8 Hz, 6H), 2.45 (s, 3H), 2.86 (sep, J=6.8 Hz, 1H), 6.13 (s, 1H), 7.23 (d, J=1.6 Hz, 1H), 7.70 (d, J=1.6 Hz, 1H).

Step 4: 5-hydroxy-2-isopropyl-4-oxo-4H-chromene-7-carboxylic acid

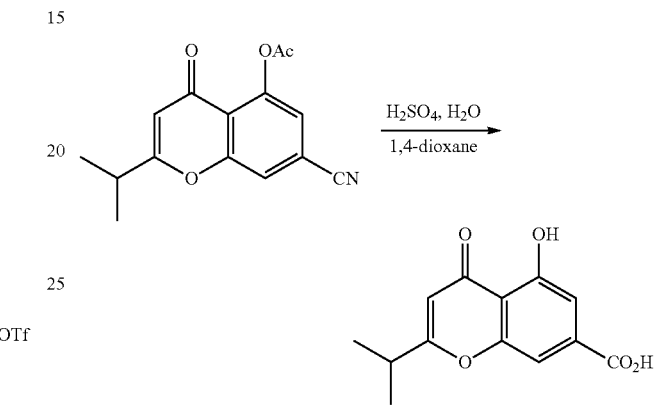

A solution of 7-cyano-2-isopropyl-4-oxo-4H-chromen-5-yl acetate (1.25 g, 4.61 mmol) in 1,4-dioxane (60 mL) was treated with H$_2$SO$_4$ (60%, 40 mL). The resultant mixture was refluxed for 4 h. The reaction was extracted with EA. The combined organic extracts were washed with brine and dried over Na$_2$SO$_4$ to afford 1.02 g (90%) of 5-hydroxy-2-isopropyl-4-oxo-4H-chromene-7-carboxylic acid as a brown solid. LC-MS (ESI): m/z 249 [M+1]$^+$; $^1$H NMR (400 MHz, DMSO-d$_6$) δ (ppm) 1.28 (d, J=6.8 Hz, 6H), 2.97 (sep, J=6.8 Hz, 1H), 6.39 (s, 1H), 7.21 (d, J=1.2 Hz, 1H), 7.52 (d, J=1.2 Hz, 1H), 12.67 (s, 1H), 13.62 (br. s, 1H).

Step 5: 5-acetoxy-2-isopropyl-4-oxo-4H-chromene-7-carboxylic acid

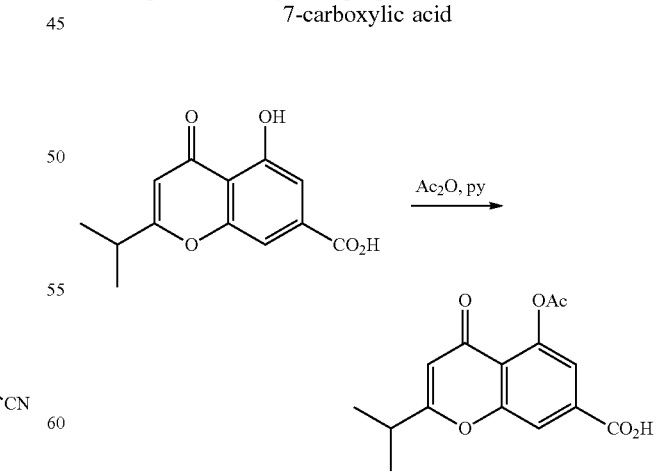

A suspension of 5-hydroxy-2-isopropyl-4-oxo-4H-chromene-7-carboxylic acid (1.02 g, 4.03 mmol) in pyridine (5 mL) was treated with Ac$_2$O (1.23 g, 12.09 mmol) at 0° C. The resultant reaction was stirred at room temperature for 14 h. The reaction was concentrated. The residue was dissolved in EA and washed with H₂O. The separated organic layer was dried over Na₂SO₄ and concentrated to afford 544 mg (47%) of 5-acetoxy-2-isopropyl-4-oxo-4H-chromene-7-carboxylic acid as a yellow solid. LC-MS (ESI): m/z 291 [M+1]⁺.

Step 6: 7-(hydroxymethyl)-2-isopropyl-4-oxo-4H-chromen-5-yl acetate

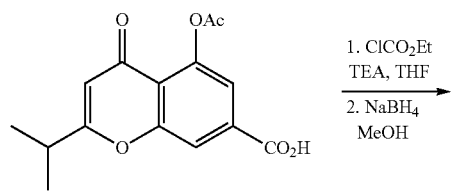

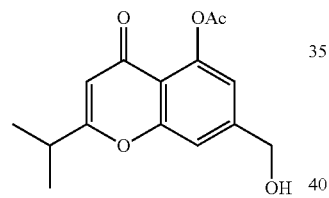

A suspension of 5-acetoxy-2-isopropyl-4-oxo-4H-chromene-7-carboxylic acid (411 mg, 1.42 mmol) in THF (15 mL) was treated with TEA (430 mg, 4.25 mmol) followed by ethyl chloroformate (307 mg, 2.83 mmol) at 0° C. The resultant mixture was stirred at 0° C. for an additional 1 h. The precipitate was filtered off. The filtrate was cooled to 0° C., treated with NaBH₄ (321 mg, 8.49 mmol), and followed by MeOH (4 mL). The reaction was stirred at 0° C. for an additional 1.5 h and quenched with saturated NH₄Cl. The reaction was extracted with EA. The combined organic extracts were washed with brine and dried over Na₂SO₄. The crude product was purified by column (hexanes:EA=1:1) to afford 179 mg (46%) of 7-(hydroxymethyl)-2-isopropyl-4-oxo-4H-chromen-5-yl acetate as a yellow solid. Supporting data: LC-MS (ESI): m/z 277 [M+1]⁺; ¹H NMR (400 MHz, CDCl₃) δ (ppm) 1.28 (d, J=6.8 Hz, 6H), 2.40 (s, 3H), 2.79 (sep, J=6.8 Hz, 1H), 4.76 (s, 2H), 6.01 (s, 1H), 6.93 (d, J=1.2 Hz, 1H), 7.36 (d, J=1.2 Hz, 1H).

Compounds of the invention can be made by the procedure outlined in Synthetic Scheme 3 from intermediates obtained by procedures outlined in Synthetic Scheme 2:

Synthetic Scheme 3

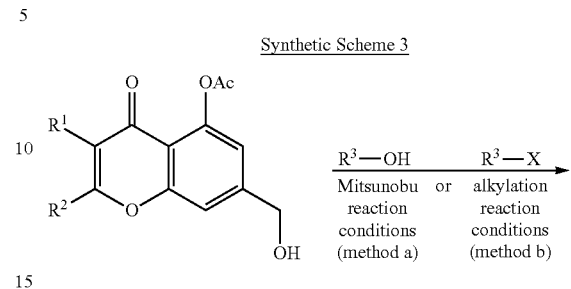

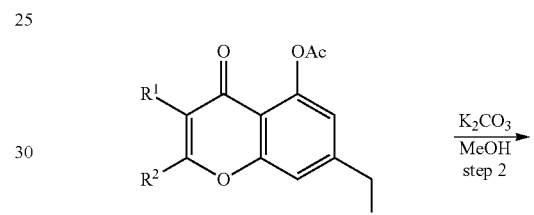

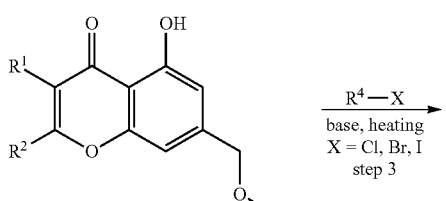

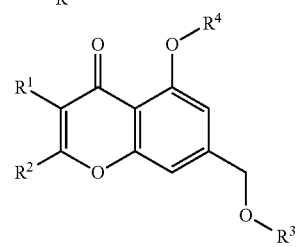

The following compound was made according to the methods of General Synthetic Scheme 3:

TABLE 4

| Example | chemical structure | groups present |
|---|---|---|
| 35 | 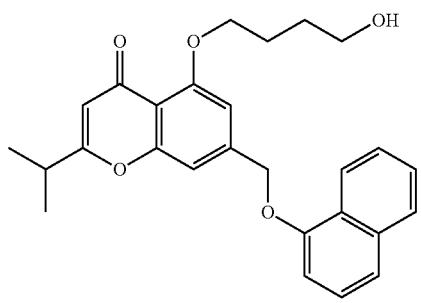 [SMILES: CC(C)c1cc(=O)c2c(OCCCCO)cc(COc3cccc4ccccc34)cc2o1] | $R^1$ = H, $R^2$ = i-Pr, Z = $CH_2O$, L = O,<br><br>$R^3$ = [naphthalenyl structure] wherein Y = H,<br><br>$R^4$ = formula (IIA) wherein $R^5$ = $R^6$ = H, n = 2 |

Example 35

5-(4-hydroxybutoxy)-2-isopropyl-7-((naphthalen-1-yloxy)methyl)-4H-chromen-4-one

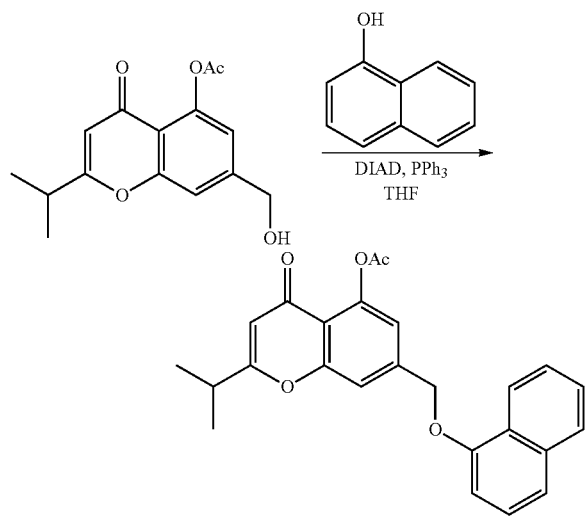

Step 1. 2-isopropyl-7-((naphthalen-1-yloxy)methyl)-4-oxo-4H-chromen-5-yl acetate A mixture of 7-(hydroxymethyl)-2-isopropyl-4-oxo-4H-chromen-5-yl acetate (28 mg, 0.10 mmol, from Example 31), 1-naphthol (17 mg, 0.12 mmol), and $PPh_3$ (37 mg, 0.14 mmol) in THF (4 mL) was treated with DIAD (28 mg, 0.14 mmol). The resultant mixture was stirred at room temperature for an additional 14 h. The reaction was diluted with EA, washed with brine, and dried over $Na_2SO_4$. The crude product was purified by column (hexanes:EA=3:1) to afford 37 mg (92%) of 2-isopropyl-7-((naphthalen-1-yloxy)methyl)-4-oxo-4H-chromen-5-ylacetate as a white solid. LC-MS (ESI): m/z 403 $[M+1]^+$.

Step 2. 5-hydroxy-2-isopropyl-7-((naphthalen-1-yloxy)methyl)-4H-chromen-4-one

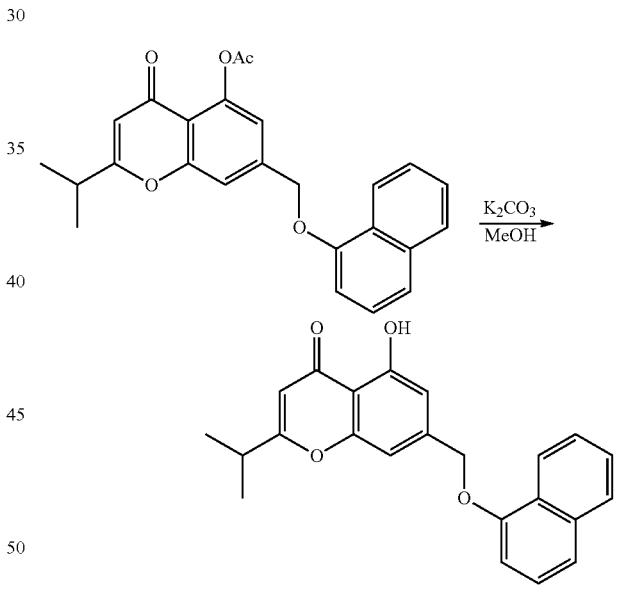

A solution of 2-isopropyl-7-((naphthalen-1-yloxy)methyl)-4-oxo-4H-chromen-5-yl acetate (37 mg, 0.092 mmol) in MeOH (10 mL) was treated with $K_2CO_3$ (127 mg, 0.92 mmol). The resultant mixture was stirred at room temperature for an additional 1 h. The reaction was diluted with EA and washed with brine. The separated organic layer was dried over $Na_2SO_4$ and concentrated to afford 35 mg of 5-hydroxy-2-isopropyl-7-((naphthalen-1-yloxy)methyl)-4H-chromen-4-one as a colorless oil. LC-MS (ESI): m/z 361 $[M+1]^+$; $^1$H NMR (400 MHz, $CDCl_3$) δ (ppm) 1.26 (d, J=6.8 Hz, 6H), 2.86 (sep, J=6.8 Hz, 1H), 5.30 (s, 2H), 6.15 (s, 1H), 6.82 (d, J=7.2 Hz, 1H), 6.93 (d, J=1.2 Hz, 1H), 7.08 (d, J=1.2 Hz, 1H), 7.34-7.55 (m, 4H), 7.82-7.84 (m, 1H), 8.39 (d, J=6.0 Hz, 1H), 12.62 (s, 1H).

Step 3: 5-(4-hydroxybutoxy)-2-isopropyl-7-((naphthalen-1-yloxy)methyl)-4H-chromen-4-one

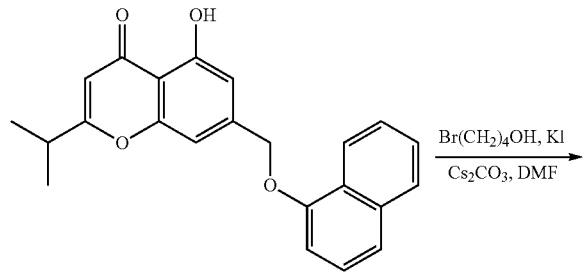

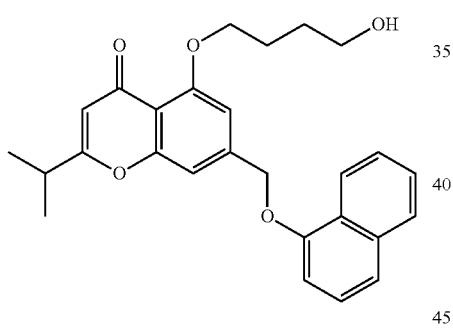

A mixture of 5-hydroxy-2-isopropyl-7-((naphthalen-1-yloxy)methyl)-4H-chromen-4-one (35 mg, 0.092 mmol) and 4-bromo-1-butanol (46 mg, 0.30 mmol) in DMF (4 mL) was treated with $Cs_2CO_3$ (65 mg, 0.20 mmol) and KI. The reaction was stirred at 70° C. for 24 h. The crude product was purified by preparative HPLC to afford 5-(4-hydroxybutoxy)-2-isopropyl-7-((naphthalen-1-yloxy)methyl)-4H-chromen-4-one as a yellow solid. Supporting data: LC-MS (ESI): m/z 433 [M+1]$^+$; $^1$H NMR (400 MHz, CDCl$_3$) δ (ppm) 1.31 (d, J=6.8 Hz, 6H), 2.10-2.13 (m, 2H), 2.82 (sep, J=6.8 Hz, 1H), 3.44-3.48 (m, 2H), 3.79 (t, J=5.6 Hz, 2H), 4.18 (t, J=5.2 Hz, 2H), 5.34 (s, 2H), 6.12 (s, 1H), 6.87 (d, J=7.2 Hz, 1H), 6.93 (d, J=1.2 Hz, 1H), 7.20 (d, J=1.2 Hz, 1H), 7.37-7.57 (m, 4H), 7.85-7.88 (m, 1H), 8.39 (d, J=6.0 Hz, 1H).

Compounds of the invention were also prepared by the procedure outlined in Synthetic Scheme 4.

Synthetic Scheme 4

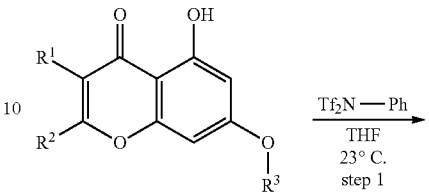

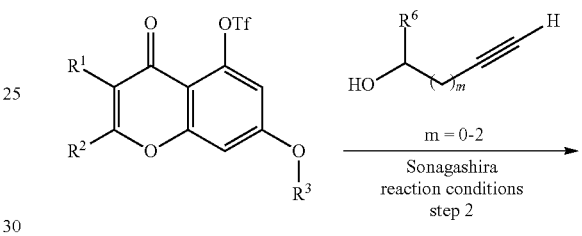

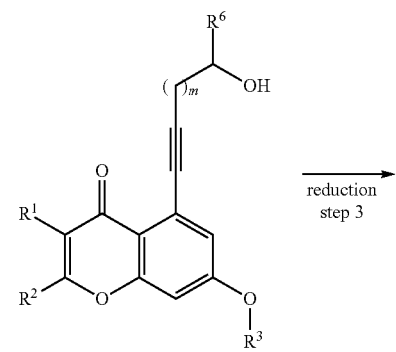

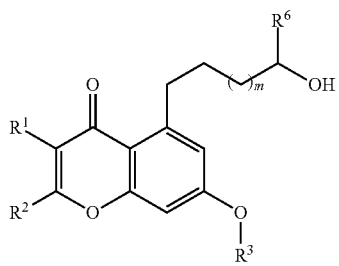

The following compounds were made according to the methods of General Scheme 4:

TABLE 5

| example | chemical structure | groups present |
|---|---|---|
| 36 | 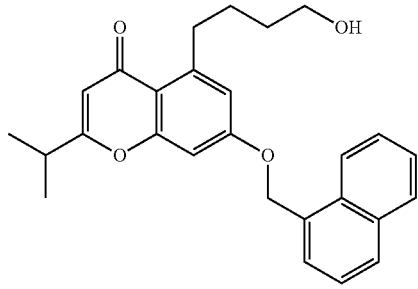 [SMILES: CC(C)c1cc(=O)c2c(CCCCO)cc(OCc3cccc4ccccc34)cc2o1] | $R^1 = H$, $R^2 = i\text{-Pr}$, $Z = OCH_2$, $L = CH_2$, $R^3 = $ naphthalen-1-yl wherein $Y = H$, $R^4 = $ formula (IIA) wherein $R^5 = R^6 = H$, $n = 1$ (m, from Scheme 4, equals 1) |
| 37 | 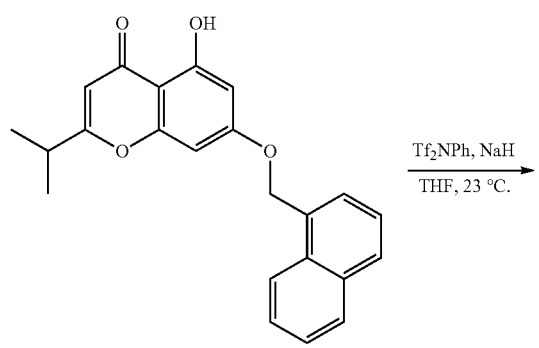 | $R^1 = H$, $R^2 = i\text{-Pr}$, $Z = OCH_2$, $L = CH_2$, $R^3 = $ naphthalen-1-yl wherein $Y = H$, $R^4 = $ formula (IIA) wherein $R^5 = R^6 = H$, $n = 2$ (m, from Scheme 4, equals 2) |

Example 36

5-(4-hydroxybutyl)-2-isopropyl-7-(naphthalen-1-ylmethoxy)-4H-chromen-4-one

Step 1.

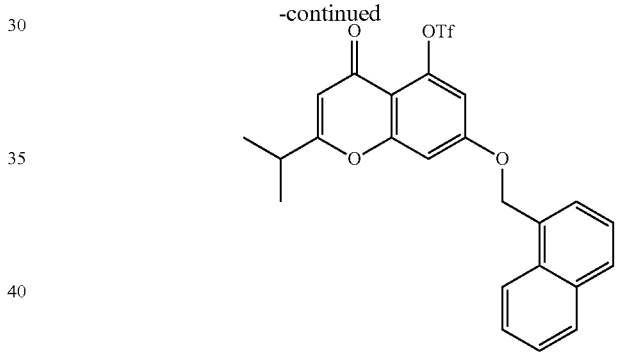

-continued

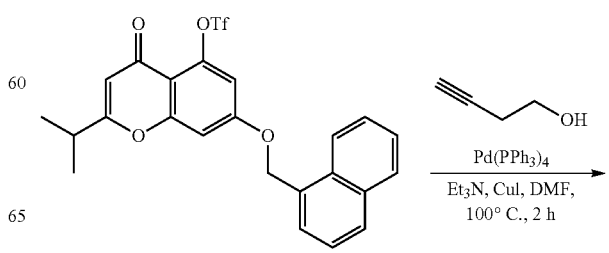

A solution of 5-hydroxy-2-isopropyl-7-(naphthalen-1-yl-methoxy)-4H-chromen-4-one (1.0 eq., from step 2 of Example 5) in THF was treated with NaH (1.1 eq.) at 0° C., then Tf₂NPh (1.2 eq.) was added. Then mixture was stirred at room temperature for 2 h, sat.NaHCO₃ was added, and the mixture was extracted with ethyl acetate (EA). The combined organic phases were washed with water and brine, dried over Na₂SO₄, then concentrated to give the product as a pale yellow solid, which was used in the next step without further purification.

Step 2.

-continued

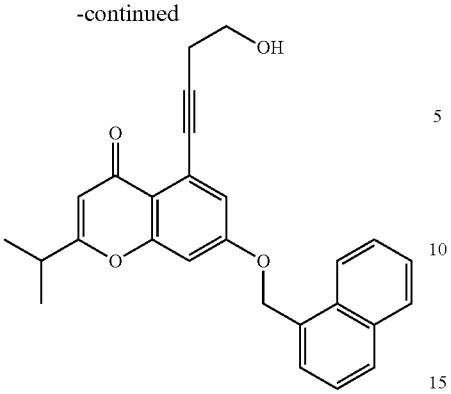

To a mixture of the product of step 1 (1.0 equiv.), Et₃N (6.0 eq.) and CuI (0.15 equiv.) in anhydrous, degassed DMF was added Pd(PPh₃)₄ (0.05 eq.) in one portion and also but-3-yn-1-ol (1.5 equiv.) The brown mixture was heated at 100° C. for 2 h, cooled to room temperature, saturated aqueous NH₄Cl solution was added, and the mixture was extracted with EA. The combined organic phases were washed with water and brine, dried over Na₂SO₄, then concentrated to give the crude product. Purification was achieved by flash column chromatography on silica gel using a gradient of ethyl acetate:hexanes as the eluent. Fractions containing the desired product were pooled and concentrated under reduced pressure to give the product as a yellow solid that was taken to Step 3.
Step 3.

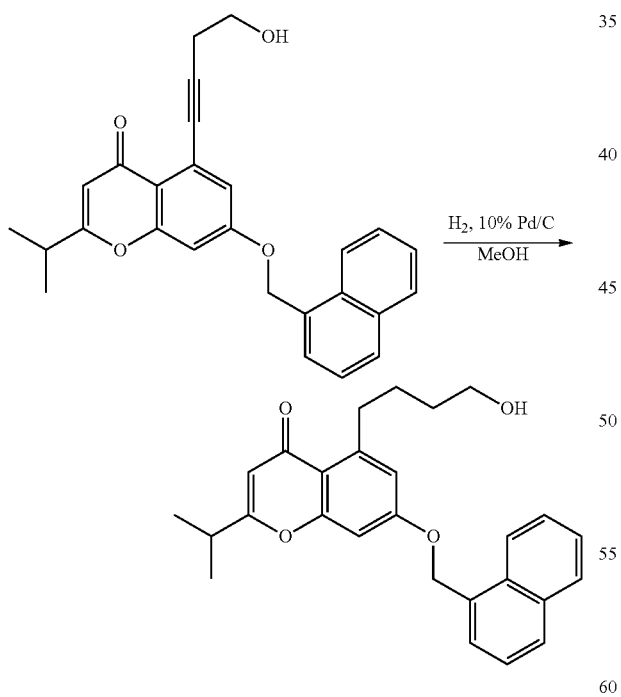

A solution of the product of step 2 in MeOH in a pressure hydrogenation vessel was treated with 10% Pd/C (0.1 eq.) at room temperature. The mixture was hydrogenated at 50 psi for 2 h. The mixture was then filtered and concentrated to give a yellow oil that was purified by preparative HPLC to give the target compound. Supporting data: LC-MS (ESI): m/z 417 [M+1]⁺; ¹H NMR (400 MHz, CDCl₃) δ 1.30 (d, J=6.8 Hz, 6H), 1.62 (t, J=3.2 Hz, 4H), 2.82-2.93 (m, 1H), 3.23 (t, J=6.4 Hz, 2H), 3.58 (t, J=6.8 Hz, 1H), 5.64 (s, 2H), 6.06 (s, 1H), 6.89 (d, J=2.4 Hz, 1H), 7.12 (d, J=2.4 Hz, 1H), 7.4-7.59 (m, 3H), 7.65 (d, J=6.4 Hz, 1H), 7.89-7.94 (m, 2H), 8.01 (dd, J=1.2, 9.2 Hz, 1H), HPLC purity >95%.

Example 37

5-(5-hydroxypentyl)-2-isopropyl-7-(naphthalen-1-ylmethoxy)-4H-chromen-4-one

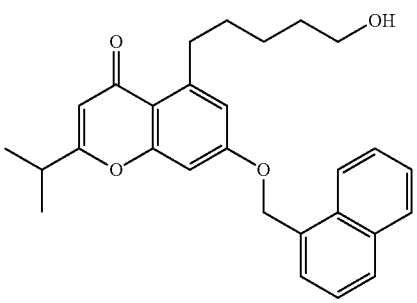

This compound was prepared following the method of Example 36 but using pent-4-yn-1-ol in step 2. Supporting data for the product of this Example: LC-MS (ESI): m/z 431[M+1]⁺; ¹H NMR (400 MHz, CDCl₃) δ (ppm) 1.30 (d, J=6.8 Hz, 6H), 1.42-1.52 (m, 3H), 1.59-1.62 (m, 3H), 2.77-2.85 (m, 1H), 3.24 (t, J=7.6 Hz, 2H), 3.66 (t, J=6.4 Hz, 2H), 5.57 (s, 2H), 6.06 (s, 1H), 6.81 (d, J=2.4 Hz, 1H), 6.90 (d, J=2.4 Hz, 1H), 7.47-7.62 (m, 4H), 7.89-7.94 (m, 2H), 8.02 (d, J=7.6 Hz, 1H), HPLC purity >95%.

Compounds of the invention were also prepared by the procedure outlined in Synthetic Scheme 5:

Synthetic Scheme 5

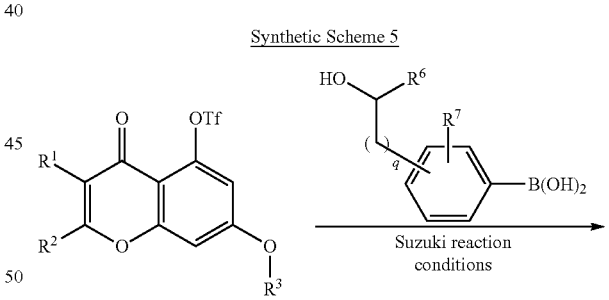

from Scheme 4

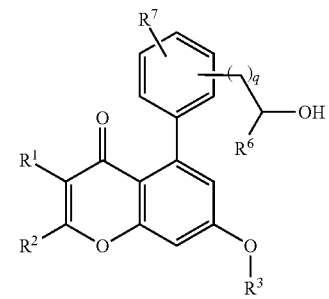

The following compounds were made according to the methods of Synthetic Scheme 5

TABLE 6

| example | chemical structure | groups present |
|---|---|---|
| 38 | 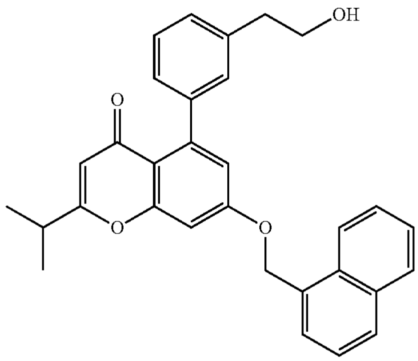 [SMILES: CC(C)c1cc(=O)c2c(-c3cccc(CCO)c3)cc(OCc3cccc4ccccc34)cc2o1] | $R^1$ = H, $R^2$ = i-Pr, Z = $OCH_2$, L = absent (a bond), $R^3$ = (1-naphthyl) wherein Y = H, $R^4$ = formula (IIC) wherein $R^5 = R^6$ = H, n = 1, and the ring = phenyl<br>q, from Scheme 5, equals 1 |
| 39 | 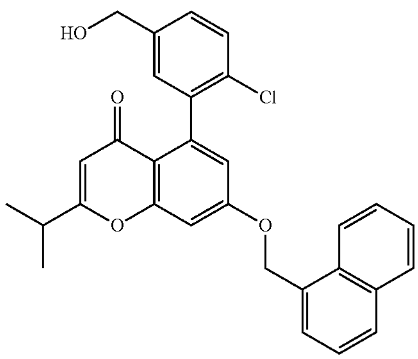 [SMILES: CC(C)c1cc(=O)c2c(-c3cc(CO)ccc3Cl)cc(OCc3cccc4ccccc34)cc2o1] | $R^1$ = H, $R^2$ = i-Pr, Z = $OCH_2$, L = absent (a bond), $R^3$ = (1-naphthyl) wherein Y = H, $R^4$ = formula (IIC) wherein $R^5$ = H, n = 0, $R^6$ = Cl and the ring = phenyl<br>q, from Scheme 5, equals 0 |
| 40 | 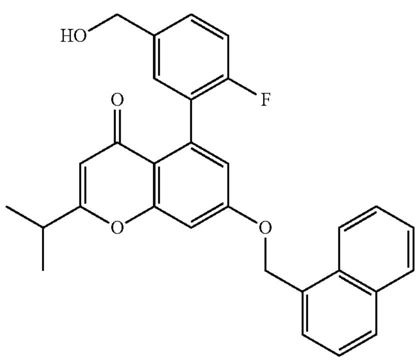 [SMILES: CC(C)c1cc(=O)c2c(-c3cc(CO)ccc3F)cc(OCc3cccc4ccccc34)cc2o1] | $R^1$ = H, $R^2$ = i-Pr, Z = $OCH_2$, L = absent (a bond), $R^3$ = (1-naphthyl) wherein Y = H, $R^4$ = formula (IIC) wherein $R^5$ = H, n = 0, $R^6$ = F and the ring = phenyl<br>q, from Scheme 5, equals 0 |
| 41 | 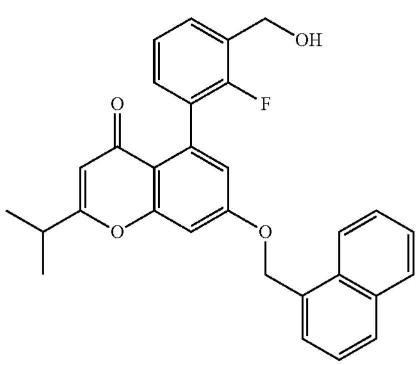 [SMILES: CC(C)c1cc(=O)c2c(-c3cccc(CO)c3F)cc(OCc3cccc4ccccc34)cc2o1] | $R^1$ = H, $R^2$ = i-Pr, Z = $OCH_2$, L = absent (a bond), $R^3$ = (1-naphthyl) wherein Y = H, $R^4$ = formula (IIC) wherein $R^5$ = H, n = 0, $R^6$ = F and the ring = phenyl<br>(a regioisomer of Example 23)<br>q, from Scheme 5, equals 0 |

TABLE 6-continued

| example | chemical structure | groups present |
|---|---|---|
| 42 | 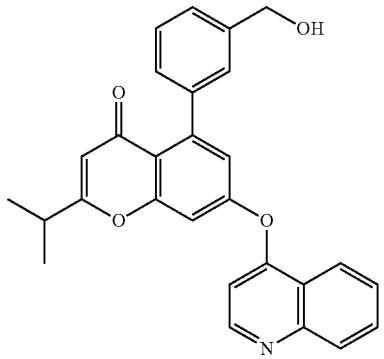 [SMILES: CC(C)c1cc(=O)c2c(-c3cccc(CO)c3)cc(Oc3ccnc4ccccc34)cc2o1] | $R^1$ = H, $R^2$ = i-Pr, Z = O, L = absent (a bond), $R^3$ =  wherein Y = H, $R^4$ = formula (IIC) wherein $R^5$ = $R^6$ = H, n = 0, and the ring = phenyl q, from Scheme 5, equals 0 |
| 43 | 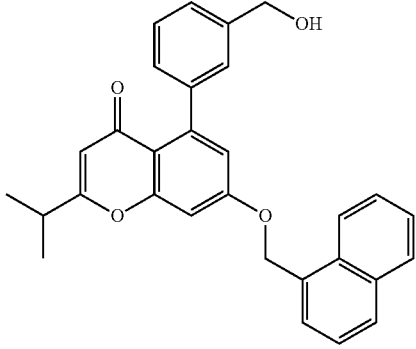 [SMILES: CC(C)c1cc(=O)c2c(-c3cccc(CO)c3)cc(OCc3cccc4ccccc34)cc2o1] | $R^1$ = H, $R^2$ = i-Pr, Z = $OCH_2$, L = absent (a bond), $R^3$ = 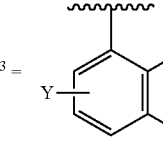 wherein Y = H, $R^4$ = formula (IIC) wherein $R^5$ = $R^6$ = H, n = 0, and the ring = phenyl q, from Scheme 5, equals 0 |
| 44 | 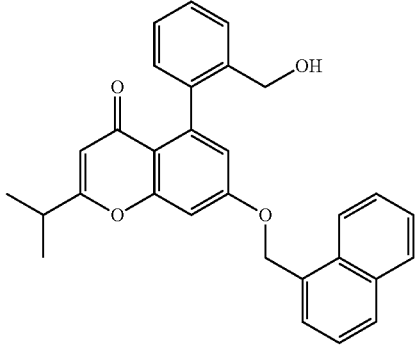 [SMILES: CC(C)c1cc(=O)c2c(-c3ccccc3CO)cc(OCc3cccc4ccccc34)cc2o1] | $R^1$ = H, $R^2$ = i-Pr, Z = $OCH_2$, L = absent (a bond), $R^3$ = 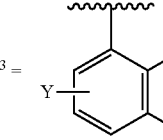 wherein Y = H, $R^4$ = formula (IIC) wherein $R^5$ = $R^6$ = H, n = 0, and the ring = phenyl; (a regioisomer of Example 43) q, from Scheme 5, equals 0 |
| 45 | 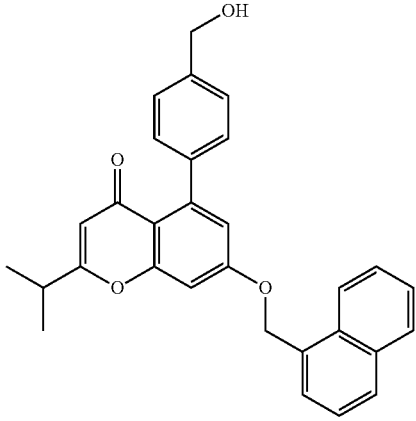 [SMILES: CC(C)c1cc(=O)c2c(-c3ccc(CO)cc3)cc(OCc3cccc4ccccc34)cc2o1] | $R^1$ = H, $R^2$ = i-Pr, Z = $OCH_2$, L = absent (a bond), $R^3$ = 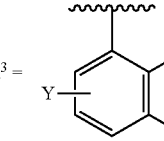 wherein Y = H, $R^4$ = formula (IIC) wherein $R^5$ = $R^6$ = H, n = 0, and the ring = phenyl; (another regioisomer of Ex. 43) q, from Scheme 5, equals 0 |

Example 38

5-(3-(2-hydroxyethyl)phenyl)-2-isopropyl-7-(naphthalen-1-ylmethoxy)-4H-chromen-4-one

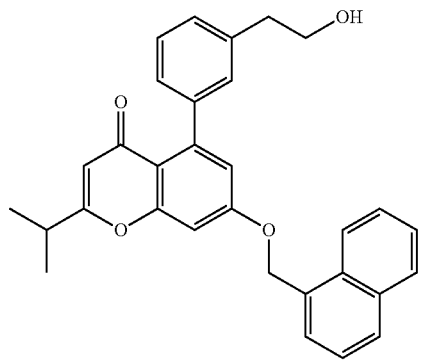

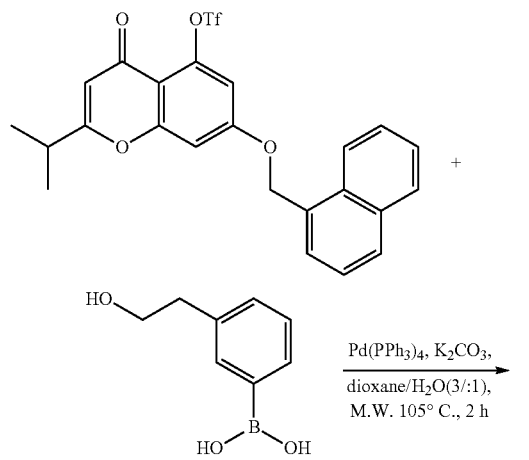

To a mixture of the triflate (1.0 equiv.), the boronic acid (1.2 equiv.), K₂CO₃ (3.0 equiv.) in degassed dioxane/H₂O (1:3) under argon was added Pd(PPh₃)₄ (0.12 eq.) in one portion. The reaction mixture was heated at 105° C. for 2 h in a microwave reactor, then cooled to room temperature, filtered and purified by preparative HPLC to give the target compound. Supporting data: LC-MS (ESI): m/z 465 [M+1]⁺; ¹H NMR (400 MHz, DMSO-d₆) δ 1.26 (d, J=6.8 Hz, 6H), 2.71-2.77 (m, 2H), 2.78-2.84 (m, 1H), 3.67 (t, 2H), 5.57 (s, 2H), 5.91 (s, 1H), 6.86 (d, J=2.4 Hz, 1H), 7.08-7.28 (m, 5H), 7.47-7.58 (m, 3H), 7.65 (d, J=6.4 Hz, 1H), 7.89-7.94 (t, 2H), 8.01 (d, J=7.6 Hz, 1H), HPLC purity >95%.

Example 39

5-(2-chloro-5-(hydroxymethyl)phenyl)-2-isopropyl-7-(naphthalen-1-ylmethoxy)-4H-chromen-4-one

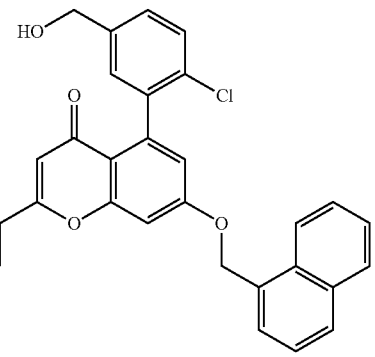

Prepared as in Example 38 using the appropriate boronic acid reagent. Supporting data: LC-MS (ESI): m/z 485 [M+1]⁺; ¹H NMR (400 MHz, CDCl₃) δ (ppm) 1.31 (d, J=7.2 Hz, 6H), 2.73-2.86 (m, 1H), 4.69 (s, 2H), 5.61 (s, 2H), 5.94 (s, 1H), 6.0 (s, 1H), 6.85 (d, J=2.4 Hz, 1H), 7.10 (d, J=2.4 Hz, 1H), 7.28 (m, 2H), 7.40 (d, J=2.4 Hz, 1H), 7.48-7.63 (m, 4H), 7.92 (td, J=7.6, 2.4 Hz, 2H), 8.04 (d, J=7.2 Hz, 1H), HPLC purity >95%.

Example 40

5-(2-fluoro-5-(hydroxymethyl)phenyl)-2-isopropyl-7-(naphthalen-1-ylmethoxy)-4H-chromen-4-one

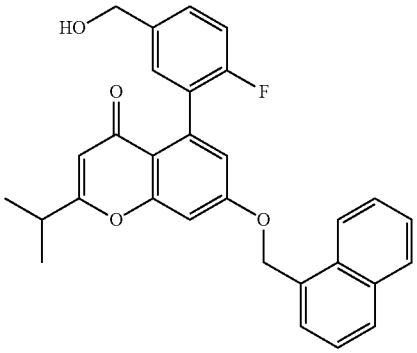 [SMILES: CC(C)c1cc(=O)c2c(-c3cc(CO)ccc3F)cc(OCc3cccc4ccccc34)cc2o1]

Prepared as in Example 38 using the appropriate boronic acid reagent. Supporting data: LC-MS (ESI): m/z 469 [M+1]⁺; ¹H NMR (400 MHz, CDCl₃) δ 1.30 (d, J=6.8 Hz, 6H), 2.78-2.85 (m, 1H), 4.69 (s, 2H), 5.61 (s, 2H), 6.01 (s, 1H), 6.90 (d, J=2.4, 1H), 7.06 (d, J=8.0 Hz, 2H), 7.09 (d, J=2.4, 1H), 7.32-7.37 (m, 1H), 7.47-7.63 (m, 4H), 7.89-7.94 (m, 2H), 8.04 (d, J=7.6 Hz, 1H), HPLC purity >95%.

Example 41

5-(2-fluoro-3-(hydroxymethyl)phenyl)-2-isopropyl-7-(naphthalen-1-ylmethoxy)-4H-chromen-4-one

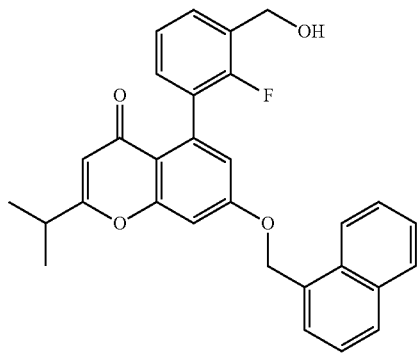 [SMILES: CC(C)c1cc(=O)c2c(-c3cccc(CO)c3F)cc(OCc3cccc4ccccc34)cc2o1]

Prepared as in Example 38 using the appropriate boronic acid reagent. Supporting data: LC-MS (ESI): m/z 469 [M+1]$^+$; $^1$H NMR (400 MHz, CDCl$_3$) δ 1.30 (d, J=6.8 Hz, 6H), 2.72-2.88 (m, 1H), 4.79 (s, 2H), 5.61 (s, 2H), 6.01 (s, 1H), 6.90 (d, J=2.4, 1H), 7.09 (d, J=2.4, 1H), 7.17-7.19 (m, 2H), 7.43-7.63 (m, 5H), 7.88-7.94 (m, 2H), 8.04 (d, J=7.6 Hz, 1H), HPLC purity >95%.

Example 42

5-(3-(hydroxymethyl)phenyl)-2-isopropyl-7-(quinolin-4-yloxy)-4H-chromen-4-one

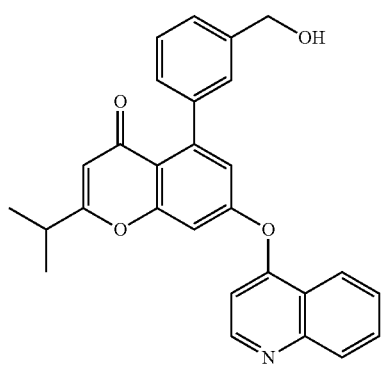 [SMILES: CC(C)c1cc(=O)c2c(-c3cccc(CO)c3)cc(Oc3ccnc4ccccc34)cc2o1]

Prepared as in Example 38 using the appropriate boronic acid reagent, using as the starting material the aryl triflate with R$^3$=4-quinoline and Z=O. Supporting data: LC-MS (ESI): m/z 438 [M+1]$^+$; $^1$H NMR (400 MHz, CDCl$_3$) δ 1.34 (d, J=6.8 Hz, 6H), 2.87-2.92 (m, 1H), 4.74 (s, 2H), 6.14 (s, 1H), 7.07 (br, 1H), 7.09 (d, J=2.0 Hz, 1H), 7.25 (br, 1H), 7.36-7.40 (m, 4H), 7.90 (t, J=7.6 Hz, 1H), 8.10 (t, J=7.2 Hz, 1H), 8.54 (d, J=8.0 Hz, 2H), 9.12 (br, 1H), HPLC purity >95%.

Example 43

5-(3-(hydroxymethyl)phenyl)-2-isopropyl-7-(naphthalen-1-ylmethoxy)-4H-chromen-4-one

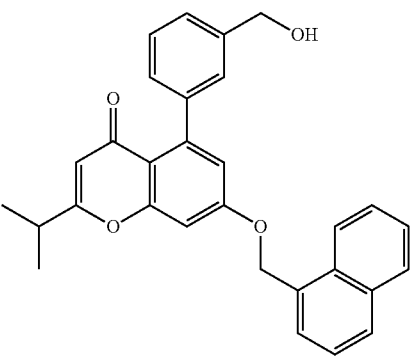 [SMILES: CC(C)c1cc(=O)c2c(-c3cccc(CO)c3)cc(OCc3cccc4ccccc34)cc2o1]

Prepared as in Example 38 using the appropriate boronic acid reagent. Supporting data: LC-MS (ESI): m/z 451 [M+1]$^+$; HPLC purity >90%.

Example 44

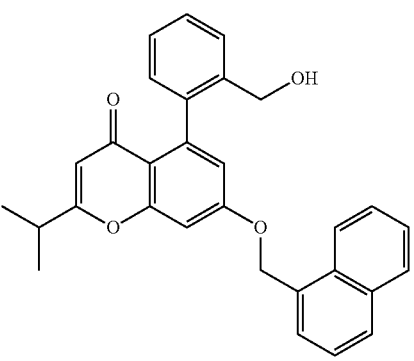 [SMILES: CC(C)c1cc(=O)c2c(-c3ccccc3CO)cc(OCc3cccc4ccccc34)cc2o1]

Prepared as in Example 38 using the appropriate boronic acid reagent. Supporting data: LC-MS (ESI): m/z 451 [M+1]$^+$; HPLC purity >90%.

Example 45

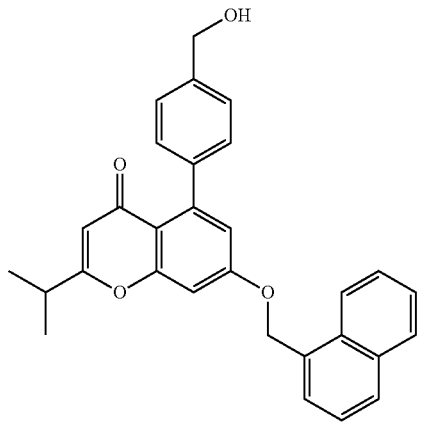 [SMILES: CC(C)c1cc(=O)c2c(-c3ccc(CO)cc3)cc(OCc3cccc4ccccc34)cc2o1]

Prepared as in Example 38 using the appropriate boronic acid reagent. Supporting data: LC-MS (ESI): m/z 451 [M+1]$^+$; HPLC purity >90%.

Compounds of the invention were also prepared by the procedure outlined in Synthetic Scheme 6:

Synthetic Scheme 6

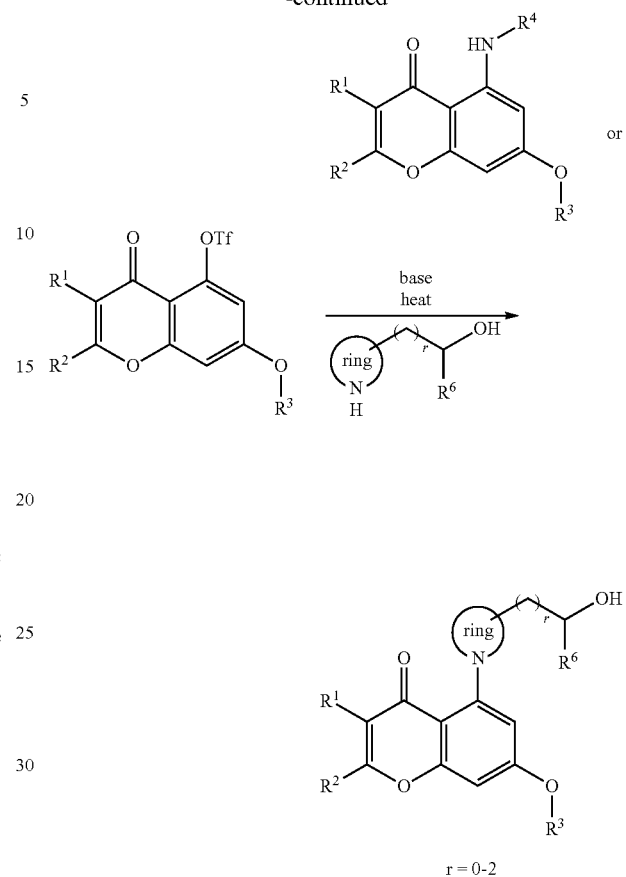

r = 0-2

The following compounds were made according to the methods of Synthetic Scheme 6:

TABLE 7

| example | chemical structure | groups present |
|---|---|---|
| 46 | ![structure] | $R^1$ = H, $R^2$ = i-Pr, Z = OCH$_2$, L = NH, $R^3$ = naphthyl (Y-substituted) wherein Y = H, $R^4$ = formula (IIA) wherein $R^5$ = $R^6$ = H, n = 2 |
| 47 | ![structure] | $R^1$ = H, $R^2$ = i-Pr, Z = OCH$_2$, L = NH, $R^3$ = naphthyl (Y-substituted) wherein Y = H, $R^4$ = formula (IIA) wherein $R^5$ = $R^6$ = H, n = 3 |

TABLE 7-continued

| example | chemical structure | groups present |
|---|---|---|
| 48 | 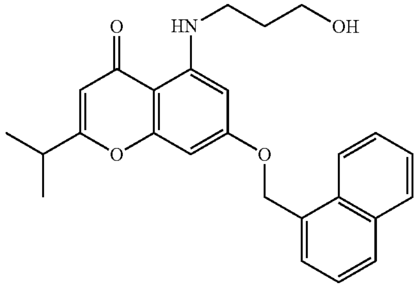 | $R^1$ = H, $R^2$ = i-Pr, Z = $OCH_2$, L = NH, $R^3$ = naphthyl wherein Y = H, $R^4$ = formula (IIA) wherein $R^5$ = $R^6$ = H, n = 1 |
| 49 | 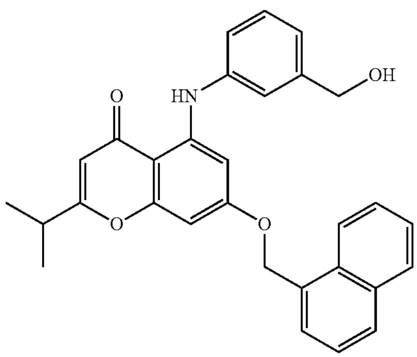 [SMILES: CC(C)c1cc(=O)c2c(Nc3cccc(CO)c3)cc(OCc3cccc4ccccc34)cc2o1] | $R^1$ = H, $R^2$ = i-Pr, Z = $OCH_2$, L = NH, $R^3$ = naphthyl wherein Y = H, $R^4$ = formula (IIC) wherein $R^5$ = $R^6$ = H, n = 0, ring = phenyl |
| 50 | 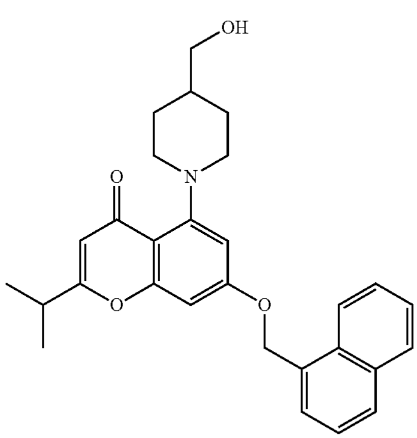 [SMILES: CC(C)c1cc(=O)c2c(N3CCC(CO)CC3)cc(OCc3cccc4ccccc34)cc2o1] | $R^1$ = H, $R^2$ = i-Pr, Z = $OCH_2$, L = NH, $R^3$ = naphthyl wherein Y = H, $R^4$ = formula (IID) wherein $R^5$ = $R^6$ = H, n = 0, ring = piperidine (substitutied at the 4-position) |

Example 46

5-((4-hydroxybutyl)amino)-2-isopropyl-7-(naphthalen-1-ylmethoxy)-4H-chromen-4-one

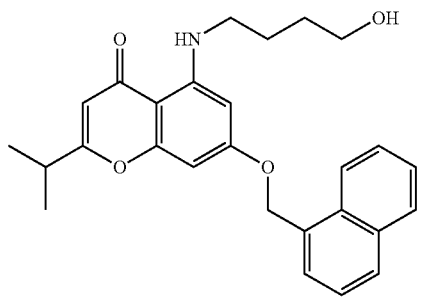

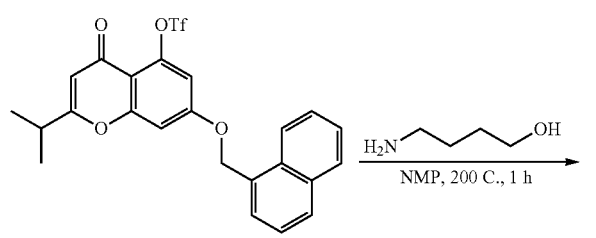

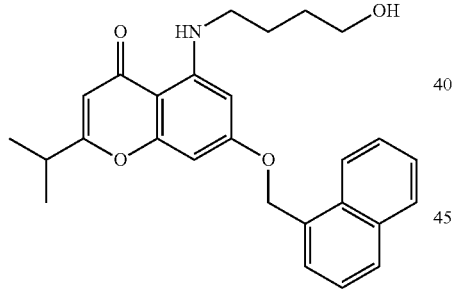

A mixture of the starting triflate (1.0 equiv.) and amine (1.5 equiv) in N-Methylpyrrolidone (NMP) was heated at 200° C. for 1 h in a microwave reactor. The black solution was cooled and diluted with EA, then washed with water three times. The organic phase was concentrated and purified by preparative HPLC to get the final product. Supporting data: LC-MS (ESI): m/z 432 [M+1]$^+$; $^1$H NMR (400 MHz, CDCl$_3$) δ (ppm) 1.27 (d, J=6.8 Hz, 6H), 1.67-1.73 (m, 2H), 1.75-1.81 (m, 2H), 2.74-2.81 (m, 1H), 3.19 (t, J=6.8 Hz, 2H), 3.69 (t, J=6.4 Hz, 2H), 5.55 (s, 2H), 5.99 (s, 1H), 6.14 (d, J=2.4 Hz, 1H), 6.33 (d, J=2.4, 1H), 7.47-7.62 (m, 4H), 7.88-7.93 (m, 2H), 8.0 (d, J=7.6 Hz, 1H), HPLC purity >95%.

Example 47

5-((5-hydroxypentyl)amino)-2-isopropyl-7-(naphthalen-1-ylmethoxy)-4H-chromen-4-one

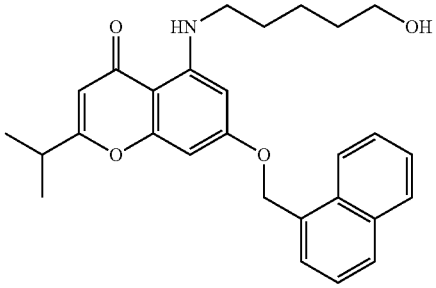 [SMILES: CC(C)c1cc(=O)c2c(NCCCCCO)cc(OCc3cccc4ccccc34)cc2o1]

Prepared as in Example 46 using the appropriate amino alcohol. Supporting data: LC-MS (ESI): m/z 446 [M+1]$^+$; $^1$H NMR (400 MHz, CDCl$_3$) δ (ppm) 1.28 (d, J=7.2 Hz, 6H), 1.47-1.53 (m, 2H), 1.57-1.65 (m, 4H), 2.74-2.81 (m, 1H), 3.16 (t, J=7.2 Hz, 2H), 3.66 (t, J=6.4 Hz, 2H), 5.56 (s, 2H), 6.02 (s, 1H), 6.17 (d, J=2.4 Hz, 1H), 6.34 (d, J=2.4 Hz, 1H), 7.477.62 (m, 4H), 7.87-7.92 (m, 2H), 8.04 (d, J=7.6 Hz 1H), HPLC purity >95%.

Example 48

5-((3-hydroxypropyl)amino)-2-isopropyl-7-(naphthalen-1-ylmethoxy)-4H-chromen-4-one

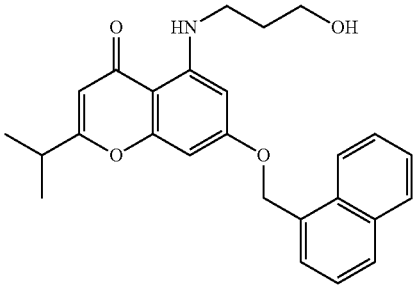

Prepared as in Example 46 using the appropriate amino alcohol. Supporting data: LC-MS (ESI): m/z 418 [M+1]$^+$; $^1$H NMR (400 MHz, CDCl$_3$) δ (ppm) 1.27 (d, J=6.8 Hz, 6H), 1.89-1.95 (m, 2H), 2.72-2.79 (m, 1H), 3.28 (t, J=6.8 Hz, 2H), 3.78 (t, J=6.0 Hz, 2H), 5.54 (s, 2H), 5.97 (s, 1H), 6.06 (d, J=2.4 Hz, 1H), 6.26 (d, J=2.4, 1H), 7.47-7.61 (m, 4H), 7.85-7.92 (m, 2H), 8.03 (d, J=8.2, 1.6 Hz, 1H), HPLC purity >95%.

Example 49

5-((3-(hydroxymethyl)phenyl)amino)-2-isopropyl-7-(naphthalen-1-ylmethoxy)-4H-chromen-4-one

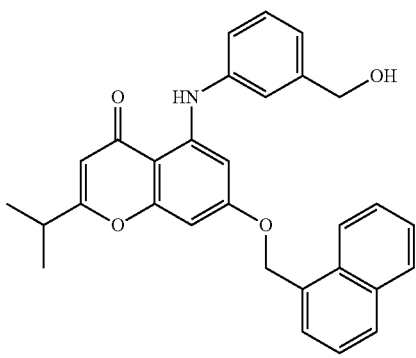 [SMILES: CC(C)c1cc(=O)c2c(Nc3cccc(CO)c3)cc(OCc3cccc4ccccc34)cc2o1]

Prepared as in Example 46 using the appropriate amino alcohol and also adding the base Et$_3$N to the reaction mixture (1.5 equiv.). Supporting data: LC-MS (ESI): m/z 466 [M+1]$^+$; [1] (400 MHz, DMSO-d$_6$) δ 1.31 (d, J=6.8 Hz, 6H), 2.83-2.90 (m, 1H), 4.56 (s, 2H), 5.57 (s, 2H), 6.11 (s, 1H), 6.54 (d, J=2.4, 1H), 6.66 (d, J=2.4, 1H), 7.06-7.11 (m, 2H), 7.28 (t, J=5.6 Hz, 2H), 7.45-7.58 (m, 3H), 7.88-7.93 (t, 2H), 8.05 (d, J=7.6 Hz, 1H), HPLC purity >95%.

Example 50

5-(4-(hydroxymethyl)piperidin-1-yl)-2-isopropyl-7-(naphthalen-1-ylmethoxy)-4H-chromen-4-one

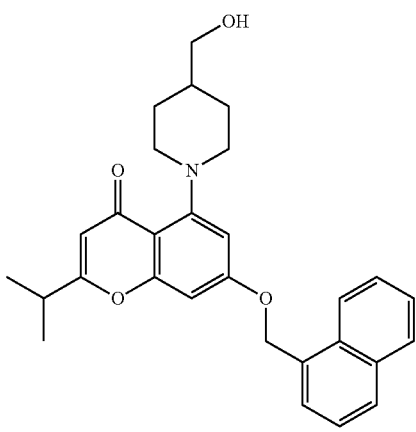 [SMILES: CC(C)c1cc(=O)c2c(N3CCC(CO)CC3)cc(OCc3cccc4ccccc34)cc2o1]

Prepared as in Example 46 using the appropriate amino alcohol. Supporting data: LC-MS (ESI): m/z 458 [M+1]$^+$; $^1$H NMR of the trifluoro acetic acid salt (400 MHz, DMSO) δ 8.11 (d, J=6.8 Hz, 1H), 7.94-7.96 (m, 2H), 7.50-7.58 (m, 4H), 7.65 (dd. J=8.4, 2.0 Hz, 1H), 7.70 (d, J=6.8 Hz, 1H), 6.42 (s, 1H), 5.79 (s, 2H), 3.68-3.73 (m, 4H), 3.54 (d, J=5.6, 2H), 3.01-3.08 (m, 1H), 2.20 (d, J=12.8 Hz, 2H), 1.96 (b, 1H), 1.75 (m, 2H), 1.38 (d, J=6.8 Hz, 6H), HPLC purity >95%.

Biological Activity

The invention provides, in various embodiments, a method of inhibiting monocarboxylate transporter MCT1, monocarboxylate transporter MCT4, or both, comprising contacting the monocarboxylate transporter with an effective amount or concentration of a compound of the invention.

The invention further provides, in various embodiments, a method of treatment of a condition in a mammal wherein treatment of the condition with a compound having an inhibitor effect on MCT1, MCT4, or both is medically indicated, comprising administering an effective amount of a compound of the invention. For example, a compound of the invention can show an antitumor, antidiabetes, anti-inflammatory, or immunosuppressive pharmacological effect. More specifically, the mammal can be a human patient.

In various embodiments, a method of treatment of a patient using an effective amount of a compound of the invention can further comprise administering an effective amount of a biguanide, e.g., metformin, to the mammal. A method of treatment of a patient using an effective amount of a compound of the invention can further comprise administering an effective amount of a standard-of-care therapeutic agent to the mammal. Administration can be carried out by an oral, intravenous, intranasal or transdermal method. In various embodiments, the condition is characterized by the heightened activity or by the high prevalence of MCT1 and/or MCT4. Examples include cancer and type II diabetes.

For instance, for a method of treatment of the invention, the condition can be cancer and the treatment can follow a determination of elevated MCT1 and/or MCT4 expression levels in the tumor or tumors.

In various embodiments, the invention provides a compound of the invention for the treatment of a malignant tumor or tumors in humans, or provides a compound of the invention for the treatment of a type II diabetes in humans.

Example 51

Biological Activity of Selected Compounds of the Invention

Specific Examples of compounds of the invention, with estimated EC$_{50}$ values determined using an MTT assay for 4-day viability of Raji (Burkitt's) lymphoma cells, a cell line known to highly express MCT1 and to be sensitive to small molecule MCT inhibitors,[4] are shown in Table 8. Assay protocols follow those described in the literature.[4] Other assays that are not described here but that are standard in the field, such as an assay for competitive inhibition of transport of radiolabeled lactic acid, an MCT substrate, may also be useful in establishing mechanism of action of these compounds.

TABLE 8

Biological activity of selected compounds of the invention

| Example | approximate potency (EC$_{50}$) |
|---|---|
| 1 | 1-10 μM |
| 2 | 1-10 μM |
| 3 | 1-10 μM |
| 4 | ≥10 μM |
| 5 | 0.1-1 μM |
| 6 | 0.1-1 μM |
| 7 | 0.1-1 μM |
| 8 | ≤100 nM |
| 9 | ≤100 nM |
| 10 | ≤100 nM |
| 11 | ≤100 nM |

TABLE 8-continued

Biological activity of selected compounds of the invention

| Example | approximate potency ($EC_{50}$) |
|---|---|
| 12 | ≤100 nM |
| 13 | ≤100 nM |
| 14 | ≤100 nM |
| 15 | 0.1-1 μM |
| 16 | ≤100 nM |
| 17 | ≤100 nM |
| 18 | 0.1-1 μM |
| 19 | ≤100 nM |
| 20 | ≤100 nM |
| 21 | 0.1-1 μM |
| 22 | 0.1-1 μM |
| 23 | ≤100 nM |
| 24 | ≤100 nM |
| 25 | ≤100 nM |
| 26 | 1-10 μM |
| 27 | ≥10 μM |
| 28 | 1-10 μM |
| 29 | 1-10 μM |
| 30 | ≤100 nM |
| 31 | 0.1-1 μM |
| 32 | 0.1-1 μM |
| 33 | 0.1-1 μM |
| 34 | not tested |
| 35 | 1-10 μM |
| 36 | 1-10 μM |
| 37 | 1-10 μM |
| 38 | 1-10 μM |
| 39 | 1-10 μM |
| 40 | 1-10 μM |
| 41 | ≥10 μM |
| 42 | 0.1-1 μM |
| 43 | 0.1-1 μM |
| 44 | ≥10 μM |
| 45 | 1-10 μM |
| 46 | 1-10 μM |
| 47 | ≥10 μM |
| 48 | 1-10 μM |
| 49 | ≥10 μM |
| 50 | 1-10 μM |

It is understood that certain claimed molecules may stably exist in with isotopic variants among specific substituents, such as deuterium or tritium in the place of hydrogen. Such isotopic variants also fall within the scope of the invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It is understood that certain groups such as amines bear a net charge. When such a group or groups are present in a "claimed compound", pharmaceutically acceptable salt forms of the structure are implicitly encompassed in the claims as well. For example, a claim for a compound with one or more amino groups present in the structure also implicitly claims all pharmaceutically acceptable salt forms, such as hydrochloride, methanesulfonyl, formate, oxalate, tartrate salts, and the like.

It is understood that certain "claimed compounds" may stably exist as hydrates or solvates. Such differing forms are also implicitly encompassed in the claims. Hydrates refer to molecules of water present in the crystal lattice. Solvates refer to molecules of a relatively benign solvent, such as ethanol, present in the crystal lattice.

It is understood that certain "claimed compounds" in any form, including as a salt, hydrate, or solvate, may stably exist in multiple solid crystalline and/or amorphous forms. Such forms may confer different physical properties (e.g., rate of dissolution, stability, hydroscopicity). Such differing solid forms are also implicitly encompassed in the claims.

Definitions

The terms MCT1 and MCT4 refer to monocarboxylate transporter isoform 1 and monocarboxylate transporter isoform 4, respectively.

The term "inhibitor" as used herein refers to a compound that binds to a target and renders it biologically inactive or less active.

The term "heteroatom" as used herein refers to an atom of any element other than carbon or hydrogen. Common heteroatoms include nitrogen, oxygen, phosphorus, sulfur and selenium.

The abbreviation "CNS" as used herein refers to the central nervous system of an organism.

The term "$EC_{50}$" as used herein refers to the dose of a test compound which produces 50% of its maximum response or effect in an assay.

The term "$IC_{50}$" as used herein refers to the dose of a test compound which produces 50% inhibition in a biochemical assay.

The term "alkyl" as used herein throughout the specification, examples, and claims refers to a hydrocarbon group, and includes branched chain variations, or "branched alkyl" groups.

The term "fluoroalkyl" refers to an alkyl group having any chemically possible number of fluorine atoms bonded thereto; thus, the term encompasses mono-, di-, and trifluoromethyl, perfluoroalkyl groups, and the like.

The term "fluoroalkoxy" refers to an alkoxy group having any chemically possible number of fluorine atoms bonded thereto; thus, the term encompasses mono-, di-, and trifluoromethoxy, perfluoroalkoxy groups, and the like.

The term "cycloalkyl" as used herein throughout the specification, examples, and claims refers to a cyclic hydrocarbon group, and may include alkyl substituents on the cyclic hydrocarbon group.

The term "substituted alkyl" as used herein refers to alkyl moieties having substituents replacing a hydrogen atom on one or more carbon atoms of the hydrocarbon backbone. Such substituents can include, for example, a halogen, a halogenated alkyl (e.g., $CF_3$), a hydroxyl, a carbonyl, an amino, an amido, an amidine, an imine, an alkoxy, a halogenated alkoxy (e.g., $OCF_3$, $OCHF_2$, etc.) a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic group. It will be understood by those skilled in the art that the moieties substituted on the hydrocarbon chain can themselves be substituted, if appropriate.

The term "aryl" and "heteroaryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names "1,2-dimethylbenzene" and "ortho, meta-dimethylbenzene" are synonymous.

The term "arylalkyl" as used herein refers to an alkyl group substituted with an aryl group (e.g., an aromatic or heteroaromatic group). Examples include CH$_2$Ph, CH$_2$CH$_2$Ph, CH$_2$CH$_2$-indole, and the like. The aromatic ring can be substituted at one or more ring positions with such substituents, as described above.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "heterocyclyl" or "heterocyclic group" as used herein refer to 3- to 10-membered ring structures, more preferably 3- to 7-membered rings that include one to four heteroatoms. Heterocycles can also be polycycles. Heterocyclyl groups include, for example, azetidine, azepine, thiophene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "halogen" designates —F, —Cl, —Br or —I.

As used herein, the term "hydroxyl" means —OH.

As used herein, the term "sulfonyl" means —SO$_2$—.

The terms "amine" and "amino" as used herein are recognized in the art and refer to both unsubstituted and substituted amines, e.g., a moiety that can be represented by the general formulas —NH$_2$, —NHR, —NRR", where R and R' are alkyl, cycloalkyl, aryl, or heterocyclyl groups, as example.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like.

The term "ether" as used herein refers to two hydrocarbons groups covalently linked by an oxygen atom.

The term "sulfonamido" is art recognized and includes a moiety that can be represented by the general formula —SO$_2$—N(R)(R') wherein where R, and R' are alkyl, cycloalkyl, aryl, or heterocyclyl groups, as examples.

The term "sulfonyl", as used herein, refers to a moiety that can be represented by the general formula —SO$_2$R wherein where R is an alkyl, cycloalkyl, aryl, or heterocyclyl group, as examples.

As used herein, the definition of each expression, e.g., alkyl, m, n, etc., when it occurs more than once in any structure, is intended to be independent of its definition elsewhere in the same structure.

When a group is specified that can be present in more than one orientation in a molecule, it is intended that all possible orientations are included. For example, when the divalent linking group OCH$_2$ is recited between groups A and B, it can be present in orientation A-OCH$_2$—B or A-CH$_2$O—B, unless otherwise specified.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The phrase "protecting group" as used herein means temporary substituents which protect a potentially reactive functional group from undesired chemical transformations. Examples of such protecting groups include carbamates of amines, esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "Example" as used herein indicates the procedures followed for the preparation of a claimed compound, In general, the compounds of the present invention may be prepared by the methods illustrated in the general reaction schemes as, for example, described in the examples, or by modifications thereof, using readily available starting materials, reagents and conventional synthesis procedures not mentioned here.

Certain abbreviations for common chemicals were used in the Examples and are defined as follows:
EA=ethyl acetate
ESI=Electrospray ionization mass spectroscopy
Et=ethyl
DIAD=diisopropyl azodicarboxylate
DMSO=dimethyl sulfoxide
DMF=N,N-dimethylformamide
Hex=hexanes
LC-MS=liquid chromatography—mass spectroscopy
HPLC=high performance liquid chromatography
Me=methyl
NMO=N-methylmorpholine N-oxide NMP=N-methyl pyrrolidinone
NMR=nuclear magnetic resonance spectroscopy
TEA=triethylamine
Ph=phenyl
Tf=trifluoromethansulfonyl

DOCUMENTS CITED

1. Warburg, O. On the origin of cancer cells. *Science* 1956, 123, 309-314.
2. Koppenol, W. H.; Bounds, P. L.; Dang, C. V. Otto Warburg's contributions to current concepts of cancer metabolism. *Nature Rev. Cancer* 2011, 11, 325-327.
3. Halestrap, A. P. The SLC16 gene family—structure, role and regulation in health and disease. *Mol. Asp. Med.* 2013, 34, 337-349.
4. Doherty, J. R.; Yang, C.; Scott, K.; Cameron M. D.; Fallahi, M.; Li, W; Hall, M. A.; Amelio, A. L.; Mishra, J. K.; Li, F; Tortosa, M.; Genau, H. M.; Rounbehler, R. J.; Yungi, L.; Dang, C. V.; Kumar, K. G.; Butler, A. A.; Bannister, T. D.; Hooper, A. T.; Unsal-Kacmaz, K.; Roush, W. R.; and Cleveland, J. L. Blocking lactate export by inhibiting the myc target MCT1 disables glycolysis and glutathione synthesis. *Cancer Res.* 2014, 74, 908-920.
5. Ullah, M. S.; Davies, A. J.; Halestrap, A. P. The plasma membrane lactate transporter MCT4, but not MCT1, is up-regulated by hypoxia through a HIF-1α-dependent mechanism. *J. Biol. Chem.* 2006, 281, 9030-9037.
6. Dang, C. V. The interplay between MYC and HIF in the Warburg effect. *Ernst Schering Found Symp. Proc.* 2007, 35-53.
7. Vaupel, P.; Mayer, A. Hypoxia in cancer: significance and impact on clinical outcome. *Cancer Metastasis Rev.* 2007, 26, 225-239.
8. Kizaka-Kondoh, S.; Inoue, M.; Harada, H.; Hiraoka, M. Tumor hypoxia: a target for selective cancer therapy. *Cancer Sci.* 2003, 94, 1021-1028.
9. Le Floch, R.; Chiche, J.; Marchiq, I.; Naiken, T.; Ilk, K.; Murray, C. M.; Critchlow, S. E.; Roux, D.; Simon, M. P.; Pouyssegur, J. CD147 subunit of lactate/$H^+$ symporters MCT1 and hypoxia-inducible MCT4 is critical for energetics and growth of glycolytic tumors. *Proc. Natl. Acad. Sci. USA* 2011, 108, 16663-16668.
10. Sonveaux, P.; Vegran, F.; Schroeder, T.; Wergin, M. C.; Verrax, J.; Rabbani, Z. N.; De Saedeleer, C.; J.; Kennedy, K. M.; Diepart, C.; Jordan, B. F.; Kelley, M. J.; Gallez, B.; Wahl, M. L.; Feron, O.; Dewhirst, M. W. Targeting lactate-fueled respiration selectively kills hypoxic tumor cells in mice. *J. Clin Invest.* 2008, 118, 3930-3942.
11. Broer, S.; Schneider, H.; Broer, A.; Rahman, B.; Hamprecht, B.; Deitmer, J. W. Characterization of the monocarboxylate transporter 1 expressed in *Xenopus laevis* oocytes by changes in cytosolic pH. *Biochem. J.* 1998, 333, 167-174.
12. Jackson, V, N.; Halestrap, A. P. The kinetics, substrate, and inhibitor specificity of the monocarboxylate (lactate) transporter of rat liver cells determined using the fluorescent intracellular pH indicator, 2',7'-bis(carboxyethyl)-5 (6)-carboxyfluorescein. *J. Biological Chem.* 1996, 271, 861-868.
13. Kobayashi, M.; Itagaki, S.; Hirano, T.; Iseki, K. mechanism of L-lactic acid transport in L6 skeletal muscle cells. *Drug Metab. Pharmacokin.* 2004, 19, 363-368.
14. Wang, Q.; Morris, M. E. Flavonoids modulate monocarboxylate transporter-1-mediated transport of γ-hydroxybutyrate in vitro and in vivo. *Drug Metabolism and Disposition* 2007, 35, 201-208.
15. Draoui, N.; Schicke, O.; Fernandes A.; Drozak, X.; Fady, N; Dumont, A.; Douxfils, J.; Hermans, E.; Dogne, J-M; Corbau, R.; Marchand, A.; Chaltin, P.; Sonveaux, P.; Feron, O.; Riant, O. Synthesis and pharmacological evaluation of carboxycoumarins as a new antitumor treatment targeting lactate transport in cancer cells. *Bioorg. Med. Chem.* 2013, 21, 7107-7117.
16. Mereddy, V. R.; Drewes, L. R.; Alam, M. A.; Jonnalagadda, S. K.; Gurrapu, S. Preparation of benzopyran derivatives and related compounds as MCT1 inhibitors. PCT Int. Appl. 2013, WO2013109972 A2 20130725.
17. Wang, H, and Bannister, T. D.; Synthesis and Structure-Activity Relationships of Pteridine Dione and Trione Monocarboxylate Transporter 1 Inhibitors, *J. Med. Chem.,* 2014, 57 (17), 7317-7324
18. Murray, C. M.; Hutchinson, R.; Bantick, J. R.; Belfield, G. P.; Benjamin, A. D.; Brazma, D.; Bundick, R. V.; Cook, I. D.; Craggs, R. I.; Edwards, S.; Evans, L. R.; Harrison, R.; Holness, E.; Jackson, A. P.; Jackson, C. G.; Kingston, L. P.; Perry, M. W. D.; Ross, A. R. J.; Rugman, P. A.; Sidhu, S. S.; Sullivan, M.; Taylor-Fishwick, D. A.; Walker, P. C.; Whitehead, Y. M.; Wilkinson, D. J.; Wright, A.; Donald, D. Monocarboxylate transporter MCT1 is a target for immunosuppression. *Nat. Chem. Biol.* 2005, 1, 371-376.
19. Guile, S. D.; Bantick, J. R.; Cheshire, D. R.; Cooper, M. E.; Davis, A. M.; Donald, D. K.; Evans, R.; Eyssade, C.; Ferguson, D. D.; Hill, S.; Hutchinson, R.; Ingall, A. H.; Kingston, L. P.; Marin, I.; Martin, B. P.; Mohammed, R. T.; Murry, C.; Perry, M. W. D.; Reynolds, R. H.; Thorne, P. V.; Wilkinson, D. J.; Withnall, J. Potent blockers of the monocarboxylate transporter MCT1: novel immunomodulatory compounds. *Bioorg. Med. Chem. Lett.* 2006, 16, 2260-2265.
20. Guile, S. D.; Bantick, J. R.; Cooper, M. E.; Donald, D. K.; Eyssade, C.; Ingall, A. H.; Lewis, R. J.; Martin, B. P.; Mohammed, R. T.; Potter, T. J.; Reynolds, R. H.; St-Gallay, S. A.; Wright, A. D. Optimization of monocarboxylate transporter 1 blockers through analysis and modulation of atropisomer interconversion properties. *J. Med. Chem.* 2007, 50, 254-263.
21. Bueno, V.; Binet, I.; Steger, U.; Bundick, R.; Ferguson, D.; Murray, C.; Donald, D.; Wood, K. The specific monocarboxylate transporter (MCT1) inhibitor, AR-C117977, a novel immunosuppressant, prolongs allograft survival in the mouse. *Transplantation* 2007, 84, 1204-1207.
22. Ovens, M. J.; Davies, A. J.; Wilson, M. C.; Murray, C. M.; Halestrap, A. P. AR-C155858 is a potent inhibitor of monocarboxylate transporters MCT1 and MCT2 that binds to an intracellular site involving transmembrane helices 7-10. *Biochem. J.* 2010, 425, 523-530.
23. Critchlow, S, E.; Tate, L. Use of a MCT1 inhibitor in the treatment of cancers expressing MCT1 over MCT4. PCT Int. Appl. 2010, WO2010089580 A1 20100812.
24. http://clinicaltrials.gov/show/NCT01791595
25. Polanski, R.; Hodgkinson, C. L.; Fusi, A.; Nonaka, D.; Priest, L.; Kelly, P.; Trapani, F.; Bishop, P. W.; White, A.; Critchlow, S. E.; Smith, P. D.; Blackhall F.; Dive, C.; Morrow, C. J. Activity of the monocarboxylate transporter 1 inhibitor AZD3965 in small cell lung cancer. *Clin. Cancer Res.* 2014, 20, 926-937.
26. Michne, W. F.; Schroeder, J. D.; Guiles, J. W.; Treasurywala, A. M.; Weigelt, C. A.; Stansberry, M. F.; McAvoy, E.; Shah, C. R.; Bump, E.; Schlegel, D. Novel Inhibitors of the Nuclear Factor of Activated T Cells (NFAT)-Mediated Transcription of .beta.-Galactosidase: Potential Immunosuppressive and Antiinflammatory Agents. *J. Med. Chem.*, 1995, 38 (14), 2557-2569.
27. Otonkoski, T; Jiao, H; Kaminen-Ahola, N; et al. Physical exercise-induced hypoglycemia caused by failed silencing of monocarboxylate transporter 1 in pancreatic beta cells. *Am J Hum Genet* 2007; 81, 467-474.
28. Zhao, C.; Wilson, M. C.; Schuit, F; Halestrap, A. P.; Rutter, G. A. Expression and distribution of lactate/monocarboxylate transporter isoforms in pancreatic islets and the exocrine pancreas. *Diabetes* 2001; 50, 361-366.
29. Sekine, N.; Cirulli, V.; Regazzi, R.; et al. Low lactate dehydrogenase and high mitochondrial glycerol phosphate dehydrogenase in pancreatic beta-cells. Potential role in nutrient sensing. *J Biol Chem* 1994, 269, 4895-4902.
30. Otonkoski, T.; Kaminen, N; Ustinov, J; et al. Physical exercise-induced hyperinsulinemic hypoglycemia is an autosomal-dominant trait characterized by abnormal pyruvate-induced insulin release. *Diabetes* 2003; 52, 199-204.
31. Pullen T. J; Sylow, L; Sun, G.; Halestrap, A. P.; Richter, E. A.; Rutter, G. A. Overexpression of Monocarboxylate Transporter-1 (Slc16a1) in Mouse Pancreatic beta-Cells Leads to Relative Hyperinsulinism During Exercise. *Diabetes* 2012, 61, 1719-1725.
32. Best, L.; Yates, A. P.; Meats, J. E.; Tomlinson, S. Effects of lactate on pancreatic islets: Lactate efflux as a possible determinant of islet-cell depolarization by glucose. *Biochem. J.* 1989; 259, 507-511.
33. Wang, Q.; Morris, M. E. Flavonoids Modulate Monocarboxylate Transporter-1-Mediated Transport of gamma-Hydroxybutyrate in Vitro and in Vivo. *Drug Metabolism and Disposition*, 2007, 35(2), 201-208.
34. Wang, X.; Wang, Q.; Morris, M. E. Pharmacokinetic Interaction between the Flavonoid Luteolin and Gamma-Hydroxybutyrate in Rats: Potential Involvement of Monocarboxylate Transporters. *The AAPS Journal*, 2008, 10(1), 47-55.

What is claimed is:

1. A method of inhibiting monocarboxylate transporter MCT1, monocarboxylate transporter MCT4, or both, comprising contacting the monocarboxylate transporter with an effective amount or concentration of a compound of formula (IA)

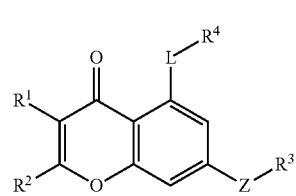

wherein
$R^1$ is H, straight chain $(C_1-C_6)$alkyl, branched chain $(C_3-C_6)$alkyl, $(C_3-C_7)$cycloalkyl, or $(C_1-C_6)$fluoroalkyl;
$R^2$ is H, straight chain $(C_1-C_6)$alkyl, branched chain $(C_3-C_6)$alkyl, $(C_3-C_7)$cycloalkyl, or $(C_1-C_6)$fluoroalkyl, a $(C_6-C_{10})$aryl ring system, a 5-to 9-membered heteroaryl ring system, a $(C_1-C_6)$alkyl-$(C_6-C_{10})$aryl ring system, or a $(C_1-C_6)$alkyl-(5- to 9-membered) heteroaryl ring system;
provided that when $R^2$ comprises an aryl or heteroaryl ring system, the ring system bears 0-2 independently selected substituents from the group consisting of fluoro, chloro, trifluoromethyl, $(C_1-C_6)$alkoxy, and $(C_1-C_6)$fluoroalkoxy;
Z is O, $CH_2$, $CH(CH_3)$, S, NH, $N((C_1-C_6)$alkyl$)$, $OCH_2$, $OCH(CH_3)$, $CH_2S$, $CH(CH_3)S$, $CH_2NH$, $CH(CH_3)NH$, $CH_2N(CH_3)$, or $CH(CH_3)N(CH_3)$;
$R^3$ is monocyclic or bicyclic (C6-C10)aryl or a monocyclic or bicyclic (5- to 10-membered)heteroaryl, wherein the aryl or heteroaryl can be substituted or unsubstituted;
L is O, $(CH_2)_m$ wherein m=1 or 2, $CH((C_1-C_6)$alkyl$)$, $CH((C_3-C_7)$cycloalkyl$)$, $CH((C_1-C_6)$alkyl$)CH_2$, S, NH, $N((C_1-C_8)$alkyl$)$, $OCH_2$, $OCH((C_1-C_6)$alkyl$)$, $SCH_2$, $SCH((C_1-C_6)$alkyl$)$, $CH_2NH$, $CH_2N((C_1-C_6)$alkyl$)$, $CH(CH_3)NH$, $CH(CH_3)N((C_1-C_6)$alkyl$)$, or a bond;
$R^4$ is a group of formula (IIA)

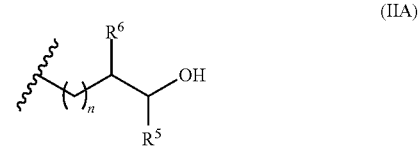

wherein a wavy line indicates a point of bonding, n=0, 1, or 2; $R^5$ is H, straight chain $(C_1-C_6)$alkyl, branched chain $(C_3-C_6)$alkyl, $(C_3-C_7)$cycloalkyl, or $(C_1-C_6)$fluoroalkyl; $R^6$ is H, methyl, or OH;
or, $R^4$ is a group of formula (IIB)

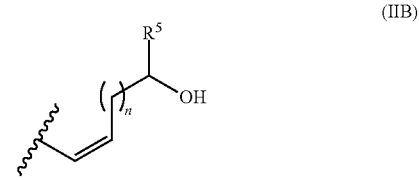

wherein a wavy line indicates a point of bonding, n=0, 1, or 2; $R^5$ is H, straight chain $(C_1-C_6)$alkyl, branched chain $(C_3-C_6)$alkyl, $(C_3-C_7)$cycloalkyl, or $(C_1-C_6)$fluoroalkyl;
or, $R^4$ is a group of formula (IIC)

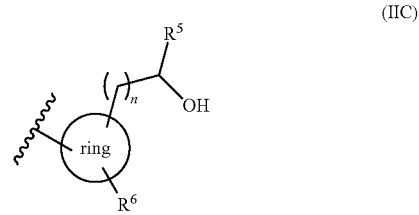

wherein a wavy line indicates a point of bonding, n=0, 1, or 2; $R^5$ is H, straight chain $(C_1-C_6)$alkyl, branched chain $(C_3-C_6)$alkyl, $(C_3-C_7)$cycloalkyl, $(C_1-C_6)$fluoroalkyl, $(C_8-C_{10})$aryl, or (4- to 7-membered)heterocyclyl comprising 1 or 2 heteroatoms selected from the group consisting of NH, N(C1-C6)alkyl, O, and S; $R^6$ is halo, $(C_1-C_6)$alkyl, $(C_1-C_6)$alkoxy, $(C_1-C_6)$fluoroalkyl, or $(C_1-C_6)$fluoroalkoxy; wherein the ring is a $(C_6-C_{10})$aryl or a (5- to 9-membered) heteroaryl comprising a carbon atom at the position of bonding of group L, and 0-3 independently selected $R^6$ groups are present as substituents on the ring; or, wherein the ring is a non-aromatic cycloalkyl or heterocyclyl ring comprising a carbon atom at the position of bonding of group L, wherein the carbon atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, N($C_1$-$C_6$)alkyl, or N($C_1C_6$)fluoroalkyl;

or, $R^4$ is a group of formula (IID)

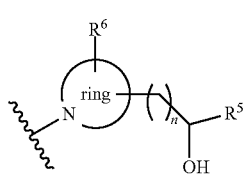

(IID)

wherein a wavy line Indicates a point of bonding; n=0, 1, or 2; $R^5$ is H, straight chain ($C_1$-$C_6$)alkyl, branched chain ($C_3$-$C_6$)alkyl, ($C_3$-$C_7$)cycloalkyl, ($C_1$-$C_6$)fluoroalkyl, ($C_6$-$C_{10}$)aryl, or (4- to 7-membered)heterocyclyl comprising 1 or 2 heteroatoms selected from the group consisting of NH, N(C1-C6)alkyl, O, and S; $R^6$ is halo, ($C_1$-$C_6$)alkyl, ($C_1$-$C_6$)alkoxy, ($C_1C_6$)fluoroalkyl, or ($C_1$-$C_6$)fluoroalkoxy; wherein the ring is a (5- to 9-membered)heterocyclyl or a (5- to 9-membered)heteroaryl comprising a nitrogen atom at the position of bonding of group L, wherein the nitrogen atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, N($C_1$-$C_6$)alkyl, or N($C_1$-$C_6$)fluoroalkyl; and 0-3 independently selected $R^6$ groups are present as substituents on the ring;

or a pharmaceutically acceptable salt thereof.

2. A method of treatment of a condition in a mammal wherein treatment of the condition with a compound having an inhibitor effect on MCT1, MCT4, or both is characterized by the heightened activity or by the high prevalence of MCT1 and/or MCT4, comprising administering an effective amount of a compound of formula (IA)

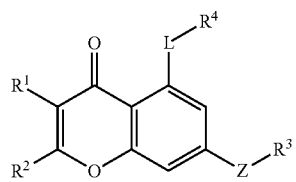

(IA)

wherein
$R^1$ is H, straight chain ($C_1$-$C_6$)alkyl, branched chain ($C_3$-$C_6$)alkyl, ($C_3$-$C_7$)cycloalkyl, or ($C_1$-$C_6$)fluoroalkyl;
$R^2$ is H, straight chain ($C_1$-$C_6$)alkyl, branched chain ($C_3$-$C_6$)alkyl, ($C_3$-$C_7$)cycloalkyl, or ($C_1$-$C_6$)fluoroalkyl, a ($C_6$-$C_{10}$)aryl ring system, a 5-to 9-membered heteroaryl ring system, a ($C_1$-$C_6$)alkyl-($C_6$-$C_{10}$)aryl ring system, or a ($C_1$-$C_6$)alkyl-(5- to 9-membered) heteroaryl ring system;

provided that when $R^2$ comprises an aryl or heteroaryl ring system, the ring system bears 0-2 independently selected substituents from the group consisting of fluoro, chloro, trifluoromethyl, ($C_1$-$C_6$)alkoxy, and ($C_1$-$C_6$)fluoroalkoxy;

Z is O, $CH_2$, $CH(CH_3)$, S, NH, N(($C_1$-$C_6$)alkyl), $OCH_2$, $OCH(CH_3)$, $CH_2S$, $CH(CH_3)S$, $CH_2NH$, $CH(CH_3)NH$, $CH_2N(CH_3)$, or $CH(CH_3)N(CH_3)$;

$R^3$ is monocyclic or bicylic (C6-C10)aryl or a monocyclic or bicyclic (5- to 10-membered)heteroaryl, wherein the aryl or heteroaryl can be substituted or unsubstituted;

L is O, $(CH_2)_m$ wherein m=1 or 2, CH(($C_1$-$C_6$)alkyl), CH((C3-C7)cycloalkyl), CH(($C_1$-$C_6$)alkyl)$CH_2$, S, NH, N(($C_1$-$C_6$)alkyl), $OCH_2$, OCH(($C_1$-$C_6$)alkyl), $SCH_2$, SCH(($C_1$-$C_6$)alkyl), $CH_2NH$, $CH_2$N(($C_1$-$C_6$)alkyl), $CH(CH_3)NH$, $CH(CH_3)$N(($C_1$-$C_6$)alkyl), or a bond;

$R^4$ is a group of formula (IIA)

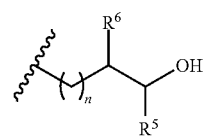

(IIA)

wherein a wavy line indicates a point of bonding, n=0, 1, or 2; $R^5$ is H, straight chain ($C_1$-$C_6$)alkyl, branched chain ($C_3$-$C_6$)alkyl, ($C_3$-$C_7$)cycloalkyl, or ($C_1$-$C_6$)fluoroalkyl; $R^6$ is H, methyl, or OH;

or, $R^4$ is a group of formula (IIB)

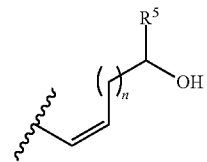

(IIB)

wherein a wavy line indicates a point of bonding, n=0, 1, or 2; $R^5$ is H, straight chain ($C_1$-$C_6$)alkyl, branched chain ($C_3$-$C_6$)alkyl, ($C_3$-$C_7$)cycloalkyl, or ($C_1$-$C_6$)fluoroalkyl;

or, $R^4$ is a group of formula (IIC)

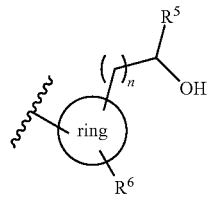

(IIC)

wherein a wavy line indicates a point of bonding, n=0, 1, or 2; $R^5$ is H, straight chain ($C_1$-$C_6$)alkyl, branched chain ($C_3$-$C_6$)alkyl, ($C_3$-$C_7$)cycloalkyl, ($C_1$-$C_6$)fluoroalkyl, ($C_6$-$C_{10}$)aryl, or (4- to 7-membered)heterocyclyl comprising 1 or 2 heteroatoms selected from the group consisting of NH, N(C1-C6)alkyl, O, and S; $R^6$ is halo, ($C_1$-$C_6$)alkyl, ($C_1$-$C_6$)alkoxy, ($C_1$-$C_6$)fluoroalkyl, or ($C_1$-$C_6$)fluoroalkoxy; wherein the ring is a ($C_6$-$C_{10}$)aryl or a (5- to 9-membered)

heteroaryl comprising a carbon atom at the position of bonding of group L, and 0-3 independently selected $R^6$ groups are present as substituents on the ring; or, wherein the ring is a non-aromatic cycloalkyl or heterocyclyl ring comprising a carbon atom at the position of bonding of group L, wherein the carbon atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, N($C_1$-$C_6$)alkyl, or N($C_1$-$C_6$)fluoroalkyl;

or, $R^4$ is a group of formula (IID)

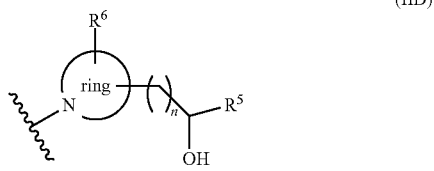

(IID)

wherein a wavy line Indicates a point of bonding; n=0, 1, or 2; $R^5$ is H, straight chain ($C_1$-$C_6$)alkyl, branched chain ($C_3$-$C_6$)alkyl, ($C_3$-$C_7$)cycloalkyl, ($C_1$-$C_6$)fluoroalkyl, ($C_6$-$C_{10}$)aryl, or (4- to 7-membered)heterocyclyl comprising 1 or 2 heteroatoms selected from the group consisting of NH, N(C1-C8)alkyl, O, and S; $R^6$ is halo, ($C_1$-$C_6$)alkyl, ($C_1$-$C_6$)alkoxy, ($C_1$-$C_6$)fluoroalkyl, or ($C_1$-$C_6$)fluoroalkoxy; wherein the ring is a (5- to 9-membered)heterocyclyl or a (5- to 9-membered)heteroaryl comprising a nitrogen atom at the position of bonding of group L, wherein the nitrogen atom of the ring bonded to L can be bonded directly to L, or can be bonded to L via a tether of an alkylene linker comprising 3 to 7 carbon atoms, wherein one of two of said 3 to 7 carbon atoms can be replaced by an independently selected heteroatom selected from the group consisting of O, NH, N($C_1$-$C_6$)alkyl, or N($C_1$-$C_6$)fluoroalkyl; and 0-3 independently selected $R^6$ groups are present as substituents on the ring;

or a pharmaceutically acceptable salt thereof.

3. The method of claim 2, wherein the compound shows an antitumor, antidiabetes, anti-inflammatory, or immunosuppressive pharmacological effect.

4. The method of claim 2, wherein the mammal is a human.

5. The method of claim 2, further comprising administering an effective amount of a biguanide to the mammal.

6. The method of claim 5, wherein the biguanide is metformin.

7. The method of claim 2, further comprising administering an effective amount of a standard-of-care therapeutic agent to the mammal.

8. The method of claim 2, wherein administration is carried out by an oral, intravenous, intranasal or transdermal method.

9. The method of claim 2, wherein the condition is characterized by the heightened activity or by the high prevalence of MCT1 and/or MCT4.

10. The method of claim 9, wherein the condition is cancer or type II diabetes.

11. The method of claim 9, wherein the condition is cancer and the treatment follows a determination of elevated MCT1 and/or MCT4 expression levels in the tumor or tumors.

* * * * *